(12) United States Patent
Hubbell et al.

(10) Patent No.: US 12,186,402 B2
(45) Date of Patent: Jan. 7, 2025

(54) POLYMER MATERIALS FOR DELIVERY OF SHORT-CHAIN FATTY ACIDS TO THE INTESTINE FOR APPLICATIONS IN HUMAN HEALTH AND TREATMENT OF DISEASE

(71) Applicant: The University of Chicago, Chicago, IL (US)

(72) Inventors: Jeffrey A. Hubbell, Chicago, IL (US); Ruyi Wang, Chicago, IL (US); D. Scott Wilson, Chicago, IL (US); Cathryn R. Nagler, Chicago, IL (US); Catherine Plunkett, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 18/303,292

(22) Filed: Apr. 19, 2023

(65) Prior Publication Data

US 2023/0293703 A1     Sep. 21, 2023

Related U.S. Application Data

(62) Division of application No. 16/605,449, filed as application No. PCT/US2018/027955 on Apr. 17, 2018, now Pat. No. 11,633,486.

(Continued)

(51) Int. Cl.
*A61K 47/58* (2017.01)
*A61K 45/06* (2006.01)
(Continued)

(52) U.S. Cl.
CPC .......... *A61K 47/58* (2017.08); *C08F 293/005* (2013.01); *A61K 45/06* (2013.01);
(Continued)

(58) Field of Classification Search
CPC ........ A61K 45/06; A61K 47/32; A61K 47/58; A61K 47/6907; A61K 47/6909;
(Continued)

(56) References Cited

U.S. PATENT DOCUMENTS 4,054,722 A   10/1977   Yoshida et al.
4,735,967 A    4/1988   Neesby
(Continued)

FOREIGN PATENT DOCUMENTS

CA   2569678    1/2014
EP   0451750   10/1991
(Continued)

OTHER PUBLICATIONS

Arbuzova et al., Synthesis and polymerization of methylolmethacrylamide esters. Polymer Science USSR, Pergamon Press, Jan. 1, 1966;8(7)1438-41.
(Continued)

*Primary Examiner* — James C Goloboy
(74) *Attorney, Agent, or Firm* — David W. Staple; Casimir Jones, S.C.

(57) ABSTRACT

Provided herein are polymer materials that find use in, for example, delivery of short-chain fatty acids. In particular, polymers are provided that form stable nanoscale structures and release their payload, for example, by cleavage of a covalent bond (e.g., via hydrolysis or enzymatic cleavage). The polymers are useful, for example, for delivery of payloads (e.g., SCFAs) to the intestine for applications in health and treatment of disease, and have broad applicability in diseases linked to changes in the human microbiota including inflammatory, autoimmune, allergic, metabolic, and central nervous system diseases, among others.

7 Claims, 37 Drawing Sheets

Related U.S. Application Data

(60) Provisional application No. 62/486,124, filed on Apr. 17, 2017.

(51) Int. Cl.
*A61K 47/69* (2017.01)
*C08F 293/00* (2006.01)

(52) U.S. Cl.
CPC ...... *A61K 47/6907* (2017.08); *A61K 47/6929* (2017.08); *C08F 2438/03* (2013.01)

(58) Field of Classification Search
CPC ............ A61K 47/6929; A61K 47/6933; A61P 37/08; C08F 2/38; C08F 293/005; C08F 2438/03
See application file for complete search history.

(56) References Cited

U.S. PATENT DOCUMENTS

| | | |
|---|---|---|
| 4,865,946 A | 9/1989 | Bowman et al. |
| 5,037,883 A | 8/1991 | Kopecek et al. |
| 5,039,703 A | 8/1991 | Breuer |
| 5,258,453 A | 11/1993 | Kopecek et al. |
| 5,569,680 A | 10/1996 | Wu |
| 5,698,611 A | 12/1997 | Okada et al. |
| 5,840,860 A | 11/1998 | Balschmidt |
| 6,197,743 B1 | 3/2001 | Faller |
| 6,203,797 B1 | 3/2001 | Perry |
| 7,399,787 B2 | 7/2008 | Chiao et al. |
| 7,718,824 B2 | 5/2010 | Girsh |
| 8,217,077 B2 | 7/2012 | Baxter et al. |
| 8,846,029 B2 | 9/2014 | Israelsen |
| 8,889,633 B2 | 11/2014 | Hondmann et al. |
| 9,078,864 B2 | 7/2015 | Gudmundsson et al. |
| 9,301,938 B2 | 4/2016 | Szewczyk |
| 9,301,966 B2 | 4/2016 | Berg |
| 9,345,727 B2 | 5/2016 | Hondmann et al. |
| 9,352,020 B2 | 5/2016 | Hondmann et al. |
| 9,598,390 B2 | 3/2017 | Shi et al. |
| 9,919,013 B2 | 3/2018 | Vuorenmaa et al. |
| 2003/0017202 A1 | 1/2003 | Bunick et al. |
| 2005/0004007 A1 | 1/2005 | Grant et al. |
| 2005/0063903 A1 | 3/2005 | Zeligs |
| 2005/0070607 A1 | 3/2005 | Andrus et al. |
| 2005/0245439 A1 | 11/2005 | Chung |
| 2005/0272644 A1 | 12/2005 | Chung |
| 2006/0068039 A1 | 3/2006 | Agger |
| 2006/0275370 A1 | 12/2006 | Chung et al. |
| 2007/0004639 A1 | 1/2007 | Kane et al. |
| 2007/0021508 A1 | 1/2007 | Yen et al. |
| 2007/0078083 A1 | 4/2007 | Barlow et al. |
| 2007/0117815 A1 | 5/2007 | Pluda et al. |
| 2007/0128266 A1 | 6/2007 | Ajani et al. |
| 2007/0207950 A1 | 9/2007 | Yao et al. |
| 2007/0208075 A1 | 9/2007 | Cottens et al. |
| 2008/0015166 A1 | 1/2008 | Van Tol et al. |
| 2008/0045445 A1 | 2/2008 | Chen et al. |
| 2008/0103165 A1 | 5/2008 | Barlow et al. |
| 2008/0113003 A1 | 5/2008 | Classen et al. |
| 2009/0123388 A1 | 5/2009 | Ganapathy et al. |
| 2009/0149533 A1 | 6/2009 | Almarsson et al. |
| 2010/0008923 A1 | 1/2010 | Shultz |
| 2010/0022444 A1 | 1/2010 | Kane et al. |
| 2010/0048595 A1 | 2/2010 | Gordon et al. |
| 2010/0112088 A1 | 5/2010 | Pravda |
| 2010/0113392 A1 | 5/2010 | Badros |
| 2010/0197758 A1 | 8/2010 | Andrews et al. |
| 2010/0222271 A1 | 9/2010 | Neu |
| 2011/0077300 A1 | 3/2011 | Ye et al. |
| 2011/0251149 A1 | 10/2011 | Perrine et al. |
| 2011/0293784 A1 | 12/2011 | Wittke |
| 2011/0294767 A1 | 12/2011 | Gedulin et al. |
| 2013/0115280 A1 | 5/2013 | Moro |
| 2014/0179782 A1 | 6/2014 | Kuang et al. |
| 2014/0349923 A1 | 11/2014 | Paulik et al. |
| 2014/0370080 A1 | 12/2014 | Stucchi et al. |
| 2015/0023922 A1 | 1/2015 | Kuang et al. |
| 2015/0023923 A1 | 1/2015 | Kuang et al. |
| 2015/0037455 A1 | 2/2015 | Chichlowski et al. |
| 2015/0119322 A1 | 4/2015 | Chichlowski et al. |
| 2015/0132396 A1 | 5/2015 | Coulter et al. |
| 2015/0157048 A1 | 6/2015 | Gaygadzhiev |
| 2015/0164833 A1 | 6/2015 | Kuang et al. |
| 2015/0224054 A1 | 8/2015 | Bell et al. |
| 2015/0231213 A1 | 8/2015 | Chichlowski et al. |
| 2015/0293123 A1 | 10/2015 | Koon et al. |
| 2016/0038447 A1 | 2/2016 | Garrett et al. |
| 2016/0129071 A1 | 5/2016 | Van Tol et al. |
| 2016/0136122 A1 | 5/2016 | Scher et al. |
| 2016/0158174 A1 | 6/2016 | Hayashi et al. |
| 2016/0206666 A1 | 7/2016 | Falb et al. |
| 2016/0220520 A1 | 8/2016 | Beaudin et al. |
| 2016/0250269 A1 | 9/2016 | Rintola et al. |
| 2016/0271086 A1 | 9/2016 | Rudensky et al. |

FOREIGN PATENT DOCUMENTS

| | | |
|---|---|---|
| EP | 1574213 | 9/2005 |
| EP | 1719508 | 11/2006 |
| EP | 1723951 | 11/2006 |
| EP | 1790333 | 5/2007 |
| EP | 2030616 | 3/2009 |
| EP | 2338476 | 6/2012 |
| EP | 1868454 | 3/2013 |
| EP | 1699449 | 1/2014 |
| EP | 2323638 | 5/2014 |
| EP | 2444082 | 9/2018 |
| FI | 124918 | 3/2015 |
| JP | 522431 | 10/1977 |
| JP | 08-292611 | 11/1996 |
| JP | 62-178502 | 1/1999 |
| WO | WO 1995/010271 | 4/1995 |
| WO | WO 1995/011699 | 5/1995 |
| WO | WO 1995/013801 | 5/1995 |
| WO | WO 1996/035440 | 11/1996 |
| WO | WO 2002/002102 | 1/2002 |
| WO | WO 2003/057730 | 7/2003 |
| WO | WO 2003/075839 | 9/2003 |
| WO | WO 2003/090557 | 11/2003 |
| WO | WO 2005/000040 | 1/2005 |
| WO | WO 2005/023179 | 3/2005 |
| WO | WO 2005/122790 | 12/2005 |
| WO | WO 2006/017692 | 2/2006 |
| WO | WO 2006/099396 | 9/2006 |
| WO | WO 2006/115412 | 11/2006 |
| WO | WO 2007/036230 | 4/2007 |
| WO | WO 2007/049262 | 5/2007 |
| WO | WO 2007/053596 | 5/2007 |
| WO | WO 2007/056243 | 5/2007 |
| WO | WO 2007/134077 | 11/2007 |
| WO | WO 2007/146730 | 12/2007 |
| WO | WO 2008/090534 | 7/2008 |
| WO | WO 2008/091170 | 7/2008 |
| WO | WO 2009/072097 | 6/2009 |
| WO | WO 2009/087474 | 7/2009 |
| WO | WO 2009/108755 | 9/2009 |
| WO | WO 2009/154463 | 12/2009 |
| WO | WO 2010/142456 | 12/2010 |
| WO | WO 2010/148572 | 12/2010 |
| WO | WO 2011/038014 | 3/2011 |
| WO | WO 2011/038224 | 3/2011 |
| WO | WO 2011/060492 | 5/2011 |
| WO | WO 2011/082111 | 7/2011 |
| WO | WO 2011/113013 | 9/2011 |
| WO | WO 2011/119228 | 9/2011 |
| WO | WO 2011/135107 | 11/2011 |
| WO | WO 2012/140504 | 10/2012 |
| WO | WO 2012/149472 | 11/2012 |
| WO | WO 2014/159802 | 3/2014 |
| WO | WO 2014/049363 | 4/2014 |
| WO | WO 2014/150556 | 9/2014 |
| WO | WO 2014/150558 | 9/2014 |
| WO | WO 2014/150571 | 9/2014 |

(56) References Cited

FOREIGN PATENT DOCUMENTS

| WO | WO 2015/006355 | 1/2015 | |
|---|---|---|---|
| WO | WO 2015/175388 | 11/2015 | |
| WO | WO 2016/025747 | 2/2016 | |
| WO | WO 2016/118730 | 7/2016 | |
| WO | WO 2016/154730 | 10/2016 | |
| WO | WO 2016/172658 | 10/2016 | |
| WO | WO-2016177354 A2 * | 11/2016 | ............. A61L 27/34 |

OTHER PUBLICATIONS

Arpaia et al., Metabolites produced by commensal bacteria promote peripheral regulatory T-cell generation. Nature. Dec. 19, 2013;504(7480):451-5.

Belkaid et al., Role of the Microbiota in Immunity and Inflammation. Cell. Mar. 27, 2014;157(1):121-41.

Berni Canani et al., Lactobacillus rhamnosus GG-supplemented formula expands butyrate-producing bacterial strains in food allergic infants. Isme J. Mar. 2016; 10(3):742-750.

Berni Canani et al., The role of the commensal microbiota in the regulation of tolerance to dietary allergens. Curr Opin Allergy Clin Immunol. Jun. 2015; 15(3): 243-249.

Chiefari et al. Living Free-Radical Polymerization by Reversible Addition-Fragmentation Chain Transfer: The RAFT Process, Macromolecules, 1998, 31, 5559-5562.

Duncan et al., Do HPMA Copolymer Conjugates Have a Future as Clinically Useful Nanomedicines? A Critical Overview of Current Status and Future Opportunities. Adv Drug Deliv Rev. Feb. 17, 2010;62(2):272-82.

Furusawa et al., Commensal microbe-derived butyrate induces the differentiation of colonic regulatory T cells. Nature. Dec. 19, 2013;504(7480):446-50.

Haag et al., Polymer Therapeutics: Concepts and Applications. Angew Chem Int Ed Engl. Feb. 13, 2006;45(8):1198-215.

Haghikia et al., Dietary Fatty Acids Directly Impact Central Nervous System Autoimmunity via the Small Intestine. Immunity. Oct. 20, 2015;43(4):817-29.

Kaur, Modulation of gut microbiota and its environment using starch-entrapped microspheres and cereal arabinoxylans. Ph.D. Dissertation, Purdue University, Apr. 23, 2012, 194 pages.

Kopecek et al., HPMA Copolymer-Anticancer Drug Conjugates: Design, Activity, and Mechanism of Action. Eur J Pharm Biopharm. Jul. 2000;50(1):61-81.

Kopecek et al., HPMA Copolymers: Origins, Early Developments, Present, and Future. Adv Drug Deliv Rev. Feb. 17, 2010;62(2):122-49.

Lub et al., A Static-Secondary-Ion-Mass-Spectrometry study of the surfaces of poly(hydroxyalkyl methacrylates) before and after chemical modificatoin. Recuil Des Travaux Chimiques Des Pays-Bas. Sep. 2, 1990;109(9):367-74.

Macfabe, Enteric short-chain fatty acids: microbial messengers of metabolism, mitochondria, and mind: implications in autism spectrum disorders. Microb Ecol Health Dis. May 29, 2015;26:28177.

Maiti et al., RAFT polymerization of fatty acid containing monomers: controlled synthesis of polymers from renewable resources. RSC Adv. 2013;3:24983.

Meijer et al., Butyrate and other short-chain fatty acids as modulators of immunity: what relevance for health? Curr Opin Clin Nutr Metab Care. Nov. 2010;13(6):715-21.

Nylund et al., Severity of atopic disease inversely correlates with intestinal microbiota diversity and butyrate-producing bacteria. Allergy. Feb. 2015;70(2):241-4.

Sandin et al., Faecal short chain fatty acid pattern and allergy in early childhood. Acta Paediatr. May 2009;98(5):823-7.

Smith et al., The microbial metabolites, short chain fatty acids, regulate colonic Treg cell homeostasis. Science. Aug. 2, 2013;341(6145):569-73.

International Search Report and Written Opinion for PCT/US2018/027955, mailed Sep. 18, 2018, 12 pages.

Extended EP Search Report for EP18788367.3, mailed Dec. 15, 2020, 8 pages.

Japanese Office Action for JP2019-556663, mailed Apr. 5, 2022.

\* cited by examiner

FIG. 20

| | | Formulation 1 | Formulation 3 | Formulation 4 |
|---|---|---|---|---|
| Molecular weight | GPC | 38,487 g/mol | 57,412 g/mol | 37,895 g/mol |
| | NMR | 40,782 g/mol | 52,101 g/mol | 38,888 g/mol |
| Ratio of active:inactive | # inactive unit | 100 | 123 | 97 |
| | # active unit | 133 | 173 | 126 |
| | total units | 233 | 296 | 225 |
| | active:inactive ratio | 0.75 | 0.71 | 0.77 |
| Particle size | | 60-70 nm | 120-130 nm | 75-82 nm |
| Appearance | | Light pink solution | Cloudy, opaque, white solution | Light pink solution |

From left to right:
1. Formulation 4 (lot 1): light pink solution
2. Formulation 4 (lot 2): light pink solution
3. Formulation 1: light pink solution
4. Formulation 3: opaque, cloudy, white suspension

POLYMER MATERIALS FOR DELIVERY OF SHORT-CHAIN FATTY ACIDS TO THE INTESTINE FOR APPLICATIONS IN HUMAN HEALTH AND TREATMENT OF DISEASE

CROSS-REFERENCE TO RELATED APPLICATIONS

The present invention is a divisional of U.S. patent application Ser. No. 16/605,449, filed Oct. 15, 2019, now allowed, which is a § 371 National Entry of PCT/US2018/027955, filed Apr. 17, 2018, which claims priority to U.S. Provisional Patent Application Ser. No. 62/486,124, filed Apr. 17, 2017, which is incorporated by reference in its entirety.

FIELD

Provided herein are polymer materials that find use in, for example, delivery of short-chain fatty acids. In particular, polymers are provided that form stable nanoscale structures and release their payload, for example, by cleavage of a covalent bond (e.g., via hydrolysis or enzymatic cleavage). The polymers are useful, for example, for delivery of payloads (e.g., short-chain fatty acids (SCFAs)) to the intestine for applications in health and treatment of disease, and have broad applicability in diseases linked to changes in the human microbiota including inflammatory, autoimmune, allergic, metabolic, and central nervous system diseases, among others.

BACKGROUND OF THE INVENTION

Host-microbiota interactions are essential for establishing appropriate immune homeostasis, and perturbations of naturally-selected bacterial populations, a condition called dysbiosis, have been linked to many different pathologies. Dysbiosis can lead to reduced concentrations of bacterial metabolites crucial for maintaining gut homeostasis, in particular short-chain fatty acids that are produced by bacterial fermentation of carbohydrates in the gut. Shortages of these acids have been correlated to a variety of conditions, including inflammatory, autoimmune, and allergic disease (Sandin et al., 2009, Nylund et al., 2015, Berni-Canani et al., 2016, incorporated by reference in their entireties), metabolic disease (Meijer et al., 2010, incorporated by reference in its entirety), and central nervous system disorders (Haghikia et al., 2015, MacFabe, 2015, incorporated by reference in their entireties), among others. Short-chain fatty acids derived from gut bacteria fermentation regulate both the proportions and functional capabilities of intestinal Treg cells (Arpaia et al., 2013; Furusawa et al., 2013; Smith et al., 2013, incorporated by reference in their entireties). As the primary fuel source of intestinal epithelial cells, they also promote barrier function and reduce permeability by increasing proliferation and mucus production (Berni-Canani et al. 2015, incorporated by reference in its entirety). Supplementing diets with short-chain fatty acids has demonstrated therapeutic effects in animal models of allergy, obesity, and others.

Translating short-chain fatty acid treatments to clinical use has been challenging because degradation occurs rapidly during transit through the gut and the molecules themselves, both as free base and acid salts, are unpalatable, malodorous, and upsetting to the stomach. Enterically-coated short-chain fatty acid products are commercially available but not widely used, partly due to the aforementioned drawbacks, as well as their inability to densely pack the pharmaceutically-active short-chain fatty acid in sufficient quantities to demonstrate therapeutic effects. None of the products have been specifically evaluated for the treatment or prevention of any specific disease.

Delivery systems that overcome the above limitations would be useful for all the known clinical applications of short-chain fatty acids enumerated above.

SUMMARY OF THE INVENTION

Provided herein are copolymers (e.g., random or block) that are delivery vehicles for short- to medium-chain hydrophobic or amphiphilic carboxylic acids (e.g., 3-12 carbon atoms in the chain, collectively referred to herein are short-chain fatty acids ["SCFA" s]) and functionalized derivatives of those acids. The polymers provide delivery of the SCFAs to the gut, including the mucosal lining of the small and large intestine, and in particular embodiments, the ileum. The SCFAs and/or their derivatives are attached to the copolymer backbone with a covalent bond, which is cleavable by hydrolysis or enzyme, thereby releasing the SCFA to have a desired therapeutic effect on human disease. The therapeutic effect is targeted at the barrier function of the intestine and the mucus layer of the gut and all diseases in which mucus layer thickness or barrier function are implicated may be treated. Exemplary human diseases that are treatable with the polymers described herein include, but are not limited to, autoimmune diseases (e.g. rheumatoid arthritis, celiac disease), allergic and atopic diseases (e.g., food allergies of all types, eosinophilic esophagitis, allergic rhinitis, allergic asthma, pet allergies, drug allergies), inflammatory conditions (e.g. inflammatory bowel disease, ulcerative colitis, Crohn's disease), infectious diseases, metabolic disorders, diseases of the central nervous system (e.g. multiple sclerosis, Alzheimer's disease, Parkinson's disease), blood disorders (e.g. beta-thalassemia) colorectal cancer, diseases effecting gut motility (e.g. diarrhea), Type I diabetes, and autism spectrum disorders, among others. The copolymers are administered by any suitable route of administration (e.g., orally, rectally, etc.), and overcome the known limitations associated with the administration of short-chain fatty acids on their own.

Embodiments herein relate to copolymers (e.g., random or block) of (i) a polymer of hydrophilic monomers and (ii) a monomer that displays an SCFA moiety and is attached to the copolymer by a methacrylate or methacrylamide group, supramolecular assemblies thereof, nanoparticles comprising such copolymers, and methods of use thereof. In some embodiments, the copolymers comprise a random, or pseudo-random distribution of the two types of monomers. In other embodiments, the copolymer is a block copolymer comprising a hydrophilic block and a block comprising monomers that display an SCFA moiety and are attached to the copolymer by a methacrylate or methacrylamide group (e.g., SFCA-displaying poly(N-oxyethyl methacrylate) block, SFCA-displaying poly(N-oxyethyl methacrylamide) block, SFCA-displaying poly(N-(4-hydroxybenzoyloxy)alkyl methacrylamide) block, SFCA-displaying poly(N-(4-hydroxybenzoyloxy)alkyl methacrylate) block, etc.).

Advantages of the polymer drug delivery systems described herein, in which the pharmaceutically-active SCFAs are covalently attached to the polymer chain, include: masking odor of SCFAs, enhancing palatability of SCFAs, and increasing the bioavailability of SCFAs, especially in the distal gut, which are otherwise ill-suited for therapeutic use. In some embodiments, polymer nanoparticles carrying SCFAs can further pack more densely, delivering therapeutically relevant doses of the bioactive molecule. In some embodiments, the delivery systems described herein can survive stomach transit and deliver a therapeutic payload of SCFAs targeted at the intestinal barrier upon hydrolysis, triggered by pH change, or by enzymatic cleavage, e.g. by bacterial or host esterases, and therefore represent attractive options for short-chain fatty acid delivery.

In some embodiments, provided herein are copolymers (e.g., block or random) of: (i) a polymer of hydrophilic monomers (or a poly-hydrophilic block) and (ii) a N-oxyalkyl methacrylamide monomer (or poly(N-oxyalkyl methacrylamide) block) with a SCFA moiety or other pharmaceutically-relevant small molecule attached to this block via a covalent bond.

In some embodiments, the N-oxyalkyl methacrylamide monomer (or poly(N-oxyalkyl methacrylamide) block) comprises monomers selected from the group consisting of oxymethyl methacrylamide, 2-oxyethyl methacrylamide, 3-oxypropyl methacrylamide, N-oxyisopropyl methacrylamide, 4-oxybutyl methacrylamide, N-oxyisobutyl methacrylamide, or N-oxyalkyl methacrylamide with longer or otherwise branched or substituted alkyl chains. In some embodiments, the N-oxyalkyl methacrylamide (or poly(N-oxyalkyl methacrylamide) block) comprises a linear alkyl chain of 1-20 carbons (e.g., 1, 2, 3, 4, 5, 6, 7, 8, 9, 10, 11, 12, 13, 14, 15, 16, 17, 18, 19, 20, or ranges therebetween (e.g., 2-8)). In some embodiments, the N-oxyalkyl methacrylamide (or poly(N-oxyalkyl methacrylamide) block) comprises a branched alkyl group of 1-20 carbons (e.g., 1, 2, 3, 4, 5, 6, 7, 8, 9, 10, 11, 12, 13, 14, 15, 16, 17, 18, 19, 20, or ranges therebetween (e.g., 2-8)), such as 2-methylpentyl, 3-ethylpentyl, 3,3-dimethylhexyl, 2,3-dimethylhexyl, 4-ethyl-2-methylhexyl, or any other suitable branched alkyl groups. In some embodiments, the N-oxyalkyl methacrylamide (or poly(N-oxyalkyl methacrylamide) block) comprises one or more double or triple carbon-carbon bonds (e.g., alkenyl or alkynyl instead of alkanyl). In some embodiments, the N-oxyalkyl methacrylamide (or poly(N-oxyalkyl methacrylamide) block) comprises a hetero alkyl group comprising one of the aforementioned alkyl groups (e.g., linear or branched) with one or more heteroatoms (e.g., O, S, NH, etc.) substituted for one of the carbons in the alkyl group (e.g., $(CH_2)_nX(CH_2)_m$, wherein m and n are independently 1-10 and X is O, S, or NH). In some embodiments, the N-oxyalkyl methacrylamide (or poly(N-oxyalkyl methacrylamide) block) comprises a substituted alkyl group comprising one of the aforementioned alkyl groups (e.g., linear or branched) with one or more pendant substituent groups (e.g., OH, NH2, =O, halogen, (e.g., Cl, F, Br, I), CN, CF3, etc.). In some embodiments, the poly(N-oxyalkyl methacrylamide) comprises a linear or branched alkyl group comprising any suitable combination of heteroatoms, pendant substituents, double bonds, etc. In particular embodiments, the N-oxyalkyl methacrylamide (or poly(N-oxyalkyl methacrylamide) block) is 2-oxyalkyl methacrylamide (or poly(2-oxyalkyl methacrylamide) block).

In some embodiments, provided herein are copolymers (e.g., block or random) of: (i) a polymer of hydrophilic monomers (or a poly-hydrophilic block) and (ii) a N-oxyalkyl phenol ester methacrylamide (or poly(N-oxyalkyl phenol ester methacrylamide) block) with a SCFA moiety or other pharmaceutically-relevant small molecule attached to this block via a covalent bond.

In some embodiments, the N-oxyalkyl 4-phenol ester methacrylamide monomer (or poly(N-oxyalkyl 4-phenol ester methacrylamide) block) comprises monomers selected from the group consisting of oxymethyl 4-phenol methacrylamide, 2-oxyethyl 4-phenol methacrylamide, 3-oxypropyl 4-phenol methacrylamide, 4-oxybutyl 4-phenol methacrylamide, or N-oxyalkyl 4-phenol methacrylamide with longer or otherwise branched or substituted alkyl chains. In some embodiments, the N-oxyalkyl 4-phenol ester methacrylamide monomer (or poly(N-oxyalkyl 4-phenol ester methacrylamide) block) comprises a linear alkyl chain of 1-20 carbons (e.g., 1, 2, 3, 4, 5, 6, 7, 8, 9, 10, 11, 12, 13, 14, 15, 16, 17, 18, 19, 20, or ranges therebetween (e.g., 2-8)). In some embodiments, the N-oxyalkyl 4-phenol ester methacrylamide monomer (or poly(N-oxyalkyl 4-phenol ester methacrylamide) block) comprises a branched alkyl group of 1-20 carbons (e.g., 1, 2, 3, 4, 5, 6, 7, 8, 9, 10, 11, 12, 13, 14, 15, 16, 17, 18, 19, 20, or ranges therebetween (e.g., 2-8)), such as 2-methylpentyl, 3-ethylpentyl, 3,3-dimethylhexyl, 2,3-dimethylhexyl, 4-ethyl-2-methylhexyl, or any other suitable branched alkyl groups. In some embodiments, the N-oxyalkyl 4-phenol ester methacrylamide monomer (or poly(N-oxyalkyl 4-phenol ester methacrylamide) block) comprises one or more double or triple carbon-carbon bonds (e.g., alkenyl or alkynyl instead of alkanyl). In some embodiments, the N-oxyalkyl 4-phenol ester methacrylamide monomer (or poly(N-oxyalkyl 4-phenol ester methacrylamide) block) comprises a hetero alkyl group comprising one of the aforementioned alkyl groups (e.g., linear or branched) with one or more heteroatoms (e.g., O, S, NH, etc.) substituted for one of the carbons in the alkyl group (e.g., $(CH_2)_nX(CH_2)_m$, wherein m and n are independently 1-10 and X is O, S, or NH). In some embodiments, the N-oxyalkyl 4-phenol ester methacrylamide monomer (or poly(N-oxyalkyl 4-phenol ester methacrylamide) block) comprises a substituted alkyl group comprising one of the aforementioned alkyl groups (e.g., linear or branched) with one or more pendant substituent groups (e.g., OH, NH2, =O, halogen, (e.g., Cl, F, Br, I), CN, CF3, etc.). In some embodiments, the poly(N-oxyalkyl methacrylamide) comprises a linear or branched alkyl group comprising any suitable combination of heteroatoms, pendant substituents, double bonds, etc. In particular embodiments, the N-oxyalkyl 4-phenol methacrylamide is poly(2-oxyethyl 4-phenol methacrylamide).

In some embodiments, poly(N-oxyalkyl 4-phenol methacrylamide), with or without any alkyl modifications described above, is substituted at any position on the phenol ring with moieties selected from the groups including, but not limited to, alkyl, hydroxyl, alkoxyl, amine, N-alkyl amine, carboxyl, halogen, nitro, and derivatives thereof.

In some embodiments, provided herein are copolymers (e.g., block or random) of: (i) a polymer of hydrophilic monomers (or a poly-hydrophilic block) and (ii) a N-oxyalkyl methacrylate monomer (or poly(N-oxyalkyl methacrylate) block) with a SCFA moiety or other pharmaceutically-relevant small molecule attached to this block via a covalent bond.

In some embodiments, the N-oxyalkyl methacrylate monomer (or poly(N-oxyalkyl methacrylate) block) comprises monomers selected from the group consisting of oxymethyl methacrylate, 2-oxyethyl methacrylate, 3-oxypropyl methacrylate, N-oxyisopropyl methacrylate, 4-oxybutyl methacrylate, N-oxyisobutyl methacrylate, or N-oxyalkyl methacrylate with longer or otherwise branched or substituted alkyl chains. In some embodiments, the N-oxyalkyl methacrylate (or poly(N-oxyalkyl methacrylate) block) comprises a linear alkyl chain of 1-20 carbons (e.g., 1, 2, 3, 4, 5, 6, 7, 8, 9, 10, 11, 12, 13, 14, 15, 16, 17, 18, 19, 20, or ranges therebetween (e.g., 2-8)). In some embodiments, the N-oxyalkyl methacrylate (or poly(N-oxyalkyl methacrylate) block) comprises a branched alkyl group of 1-20 carbons (e.g., 1, 2, 3, 4, 5, 6, 7, 8, 9, 10, 11, 12, 13, 14, 15, 16, 17, 18, 19, 20, or ranges therebetween (e.g., 2-8)), such as 2-methylpentyl, 3-ethylpentyl, 3,3-dimethylhexyl, 2,3-dimethylhexyl, 4-ethyl-2-methylhexyl, or any other suitable branched alkyl groups. In some embodiments, the N-oxyalkyl methacrylate (or poly(N-oxyalkyl methacrylate) block) comprises one or more double or triple carbon-carbon bonds (e.g., alkenyl or alkynyl instead of alkanyl). In some embodiments, the N-oxyalkyl methacrylate (or poly(N-oxyalkyl methacrylate) block) comprises a hetero alkyl group comprising one of the aforementioned alkyl groups (e.g., linear or branched) with one or more heteroatoms (e.g., O, S, NH, etc.) substituted for one of the carbons in the alkyl group (e.g., $(CH_2)_nX(CH_2)_m$, wherein m and n are independently 1-10 and X is O, S, or NH). In some embodiments, the N-oxyalkyl methacrylate (or poly(N-oxyalkyl methacrylate) block) comprises a substituted alkyl group comprising one of the aforementioned alkyl groups (e.g., linear or branched) with one or more pendant substituent groups (e.g., OH, NH2, =O, halogen, (e.g., Cl, F, Br, I), CN, CF3, etc.). In some embodiments, the poly(N-oxyalkyl methacrylate) comprises a linear or branched alkyl group comprising any suitable combination of heteroatoms, pendant substituents, double bonds, etc. In particular embodiments, the N-oxyalkyl methacrylate (or poly(N-oxyalkyl methacrylate) block) is 2-oxyalkyl methacrylate (or poly(2-oxyalkyl methacrylate) block).

In some embodiments, provided herein are copolymers (e.g., block or random) of: (i) a polymer of hydrophilic monomers (or a poly-hydrophilic block) and (ii) a N-oxyalkyl phenol ester methacrylate (or poly(N-oxyalkyl phenol ester methacrylate) block) with a SCFA moiety or other pharmaceutically-relevant small molecule attached to this block via a covalent bond.

In some embodiments, the N-oxyalkyl 4-phenol ester methacrylate monomer (or poly(N-oxyalkyl 4-phenol ester methacrylate) block) comprises monomers selected from the group consisting of oxymethyl 4-phenol methacrylate, 2-oxyethyl 4-phenol methacrylate, 3-oxypropyl 4-phenol methacrylate, 4-oxybutyl 4-phenol methacrylate, or N-oxyalkyl 4-phenol methacrylate with longer or otherwise branched or substituted alkyl chains. In some embodiments, the N-oxyalkyl 4-phenol ester methacrylate monomer (or poly(N-oxyalkyl 4-phenol ester methacrylate) block) comprises a linear alkyl chain of 1-20 carbons (e.g., 1, 2, 3, 4, 5, 6, 7, 8, 9, 10, 11, 12, 13, 14, 15, 16, 17, 18, 19, 20, or ranges therebetween (e.g., 2-8)). In some embodiments, the N-oxyalkyl 4-phenol ester methacrylate monomer (or poly(N-oxyalkyl 4-phenol ester methacrylate) block) comprises a branched alkyl group of 1-20 carbons (e.g., 1, 2, 3, 4, 5, 6, 7, 8, 9, 10, 11, 12, 13, 14, 15, 16, 17, 18, 19, 20, or ranges therebetween (e.g., 2-8)), such as 2-methylpentyl, 3-ethylpentyl, 3,3-dimethylhexyl, 2,3-dimethylhexyl, 4-ethyl-2-methylhexyl, or any other suitable branched alkyl groups. In some embodiments, the N-oxyalkyl 4-phenol ester methacrylate monomer (or poly(N-oxyalkyl 4-phenol ester methacrylate) block) comprises one or more double or triple carbon-carbon bonds (e.g., alkenyl or alkynyl instead of alkanyl). In some embodiments, the N-oxyalkyl 4-phenol ester methacrylate monomer (or poly(N-oxyalkyl 4-phenol ester methacrylate) block) comprises a hetero alkyl group comprising one of the aforementioned alkyl groups (e.g., linear or branched) with one or more heteroatoms (e.g., O, S, NH, etc.) substituted for one of the carbons in the alkyl group (e.g., $(CH_2)_nX(CH_2)_m$, wherein m and n are independently 1-10 and X is O, S, or NH). In some embodiments, the N-oxyalkyl 4-phenol ester methacrylate monomer (or poly(N-oxyalkyl 4-phenol ester methacrylate) block) comprises a substituted alkyl group comprising one of the aforementioned alkyl groups (e.g., linear or branched) with one or more pendant substituent groups (e.g., OH, NH2, =O, halogen, (e.g., Cl, F, Br, I), CN, CF3, etc.). In some embodiments, the poly(N-oxyalkyl methacrylate) comprises a linear or branched alkyl group comprising any suitable combination of heteroatoms, pendant substituents, double bonds, etc. In particular embodiments, the N-oxyalkyl 4-phenol methacrylate is poly(2-oxyethyl 4-phenol methacrylate).

In some embodiments, poly(N-oxyalkyl 4-phenol methacrylate), with or without any alkyl modifications described above, is substituted at any position on the phenol ring with moieties selected from the groups including, but not limited to, alkyl, hydroxyl, alkoxyl, amine, N-alkyl amine, carboxyl, halogen, nitro, and derivatives thereof.

In some embodiments, the polymer of hydrophilic monomers is selected from the group consisting of poly(ethylene oxide) ("PEG"), poly(ethylene oxide)-co-poly(propylene oxide) random, di- or multiblock copolymers, poly(vinyl alcohol), poly(ethylene-co-vinyl alcohol), poly(N-vinyl pyrrolidone), poly(acrylic acid), poly(methyloxazoline) ("PMOXA"), poly(ethyloxazoline), poly(alkylacrylates), poly(acrylamide), poly(N-alkylacrylamides), hydrophilic polypeptide, polysaccharide, poly(N,N-dialkylacrylamides), hyaluronic acid, alginate, cyclodextrin, or poly(N-acryloylmorpholine). In some embodiments, polymer of hydrophilic monomers (whether in a block or random copolymer) are attached to the copolymer by a methacrylate or methacrylamide group. In particular embodiments, the hydrophilic block is poly(N-(2-hydroxypropyl)methacrylamide) ("pHPMA" or "polyHPMA"). In certain embodiments, the molecular weight of the polyHPMA block is 7000-15,000 Da (e.g., 7000 Da, 8000 Da, 9000 Da, 10000 Da, 11000 Da, 12000 Da, 13000 Da, 14000 Da, 15000 Da, or ranges therebetween (e.g., 9000-14000 Da)).

In particular embodiments, the copolymer comprises a covalently-attached SCFA moiety or other pharmaceutically-relevant small molecule. In some embodiments, the SCFA moiety is selected from the group consisting of acetic acid, propionic acid, isopropionic acid, butyric acid, isobutyric acid, valeric acid, isovaleric acid, caproic acid, caprylic acid, capric acid, lauric acid, and derivatives thereof. In some embodiments, any fatty acids with an aliphatic tail of 12 or fewer carbons (e.g., 1, 2, 3, 4, 5, 6, 7, 8, 9, 10, 11, 12, or any ranges therein (e.g., 3-10) may find use in embodiments herein. In certain embodiments, the SCFA moiety is butyrate (butyric acid) or iso-butyrate (iso-butyric acid).

In some embodiments, the ratio of the hydrophilic block to the SCFA-displaying (or other pharmaceutically-relevant-small-molecule-displaying) block is between 0.25 and 3.5 (e.g., 0.25, 0.3, 0.35, 0.4, 0.45, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, or ranges therebetween (e.g., 0.7-1.8)). In some embodiments, the ratio of the hydrophilic monomer to the SCFA-displaying (or other pharmaceutically-relevant-small-molecule-displaying) monomer is between 0.5 and 2.0 (e.g., 0.5, 0.6, 0.7, 0.8, 0.9, 1.0, 1.1, 1.2, 1.3, 1.4, 1.5, 1.6, 1.7, 1.8, 1.9, 2.0, or ranges therebetween (e.g., 0.7-1.8)).

In some embodiments, a polymer comprises hydrophilic monomer to hydrophobic monomer incorporation ratio of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20 (or any ranges therebetween).

In some embodiments, a polymer comprises 20-80 percent by weight (e.g., 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, or ranges therebetween) hydrophilic monomer. In some embodiments, a polymer comprises 20-80 percent by weight (e.g., 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, or ranges therebetween) hydrophobic monomer.

In some embodiments, provided herein are copolymers comprising HPMA monomers (or a polyHPMA block), and SCFA moieties (e.g., butyrate or iso-butyrate) or other pharmaceutically-relevant small molecule covalently attached, via a linker group, to the copolymer by a methacrylate or methacrylamide group.

In some embodiments, provided herein are supramolecular assemblies comprising a plurality of the copolymers (e.g., comprising SCFAs or other small molecular cargo) described herein (e.g. dispersed in a liquid). In some embodiments, an assembly is a nanoparticle between 10-1000 nm in diameter (e.g., 10, 20, 50, 100, 200, 500, 1000 nm, or ranges therebetween (e.g., 50-500 nm)). In certain embodiments, the plurality of block copolymers comprises linear and branched copolymers self-assembled or covalently linked to form the nanoparticle. In other embodiments, the assembly is a micelle. In yet other embodiments, the supramolecular assemblies are isolated (e.g. as a powder) and redispersed (e.g. in a liquid).

In some embodiments, provided herein are methods of delivering a target molecule (e.g., SCFA) to a subject (e.g., a human subject, a male subject, a female subject, etc.), the method comprising providing a supramolecular assembly of the copolymers described herein, wherein the supramolecular assembly comprises the target molecule (e.g., SCFA); and contacting the subject with the supramolecular assembly, thereby delivering the target molecule to the subject. In some embodiments, a composition (e.g., pharmaceutical composition) comprising the block copolymers described herein and/or supramolecular assemblies thereof are administered to a subject by any suitable route of administration. In some embodiments, the target molecule (e.g., SCFA) is covalently attached to the supramolecular assembly. In particular embodiments, the supramolecular assembly is contacted (e.g., administered) orally when given to the subject. In some embodiments, the supramolecular assembly is dispersed in a liquid carrier when contacted with the subject. In other embodiments, the supramolecular assembly is a solid when contacted with the subject. In some embodiments the supramolecular assembly is for use as a medicament.

In some embodiments, provided herein is the use of a supramolecular assembly of the copolymers described herein in the manufacture of a medicament.

In some embodiments, provided herein are pharmaceutical compositions comprising the supramolecular assemblies described herein. In particular embodiments, a supramolecular assembly is combined with a pharmaceutically acceptable carrier (e.g., considered to be safe and effective) and is administered to a subject (e.g., without causing undesirable biological side effects or unwanted interactions).

In some embodiments, provided herein are compositions comprising a copolymer of (i) a hydrophilic monomer and (ii) a monomer of formula (I):

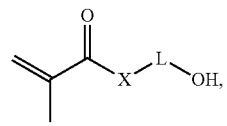

wherein X is O, NH, or S; wherein L is a linker selected from an alkyl chain, an heteroalkyl chain, a substituted alkyl chain, or a substituted heteroalkyl chain; wherein the copolymer displays one or more short-chain fatty acid (SCFA) moieties.

In some embodiments, provided herein are compositions comprising a copolymer of (i) a hydrophilic monomer and (ii) a monomer of formula (II):

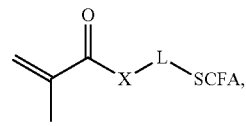

wherein X is O, NH, or S; wherein L is a linker selected from an alkyl chain, an heteroalkyl chain, a substituted alkyl chain, or a substituted heteroalkyl chain; and wherein SCFA is a short-chain fatty acid.

In some embodiments, the hydrophilic monomer forms a polymer selected from the group consisting of poly(ethylene oxide) ("PEG"), poly(ethylene oxide)-co-poly(propylene oxide) random, di- or multiblock copolymers, poly(vinyl alcohol), poly ethylene-co-vinyl alcohol), poly(N-vinyl pyrrolidone), poly(acrylic acid), poly(methyloxazoline) ("PMOXA"), poly(ethyloxazoline), poly(alkylacrylates), poly(acrylamide), poly(N-alkylacrylamides), hydrophilic polypeptide, polysaccharide, poly(N,N-dialkylacrylamides), hyaluronic acid, alginate, cyclodextrin, poly(N-acryloylmorpholine), and poly(N-(2-hydroxypropyl)methacrylamide) ("polyHPMA"). In some embodiments, the hydrophilic monomer comprises a methacrylamide or methacrylate terminus for polymerization. In some embodiments, the hydrophilic monomer comprises HPMA.

In some embodiments, L of formula (I) or formula (II) is $(CH_2)_n$, wherein n is 1-16 (e.g., 1, 2, 3, 4, 5, 6, 7, 8, 9, 10, 11, 12, 13, 14, 15, 16, or ranges therebetween). In some embodiments, L is $(CH_2)_nO(CO)$-benzene. In some embodiments, the SCFA is covalently attached to the monomer of formula (I). In some embodiments, the SCFA attached to the monomer of formula (I) comprises formula (II):

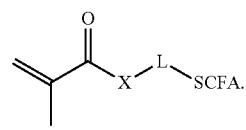

In some embodiments, the SCFA attached to the monomer of formula (I) or formula (II) comprises formula (III):

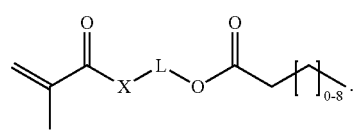

In some embodiments, the SCFA is selected from the group consisting of acetic acid, propionic acid, isopropionic acid, butyric acid, isobutyric acid, valeric acid, isovaleric acid, caproic acid, caprylic acid, capric acid, lauric acid, branched versions thereof, and derivatives thereof. In some embodiments, the SCFA is butyric acid.

In some embodiments, the copolymer is a block copolymer comprising a hydrophilic block and a block of formula (I) or formula (II). In some embodiments, the block copolymer comprises the formula (IV)

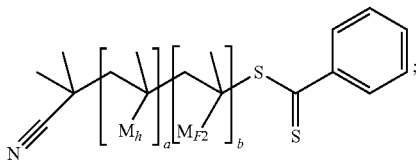

wherein $M_h$ is the side chain of the hydrophilic monomer, $M_{F2}$ is the side chain of the monomer of Formula (II):

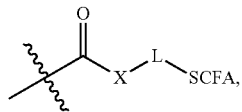

wherein a is 1-1000 (e.g., 10, 20, 30, 40, 50, 60, 70, 80, 90, 100, 125, 133, 150, 175, 200, 250, 300, 400, 500, 600, 700, 800, 900, 1000, or ranges therebetween) and b is 1-1000 (e.g., 10, 20, 30, 40, 50, 60, 70, 80, 90, 100, 125, 133, 150, 175, 200, 250, 300, 400, 500, 600, 700, 800, 900, 1000, or ranges therebetween).

In some embodiments, the copolymer is a random copolymer. In some embodiments, the random copolymer comprises formula (V):

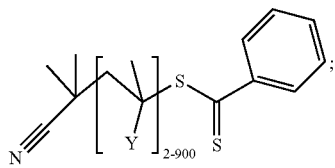

wherein each Y is independently selected from the side chain of a polymer formed from formula (II):

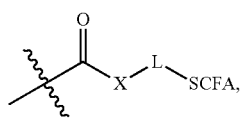

and the side chain of polyHPMA:

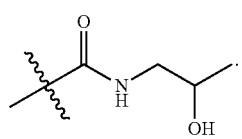 [SMILES: *C(=O)NCC(C)O]

In some embodiments, there are 2, 5, 10, 20, 30, 40, 50, 75, 100, 125, 150, 175, 200, 250, 300, 350, 400, 450, 500, 550, 600, 650, 700, 750, 800, 850, 900, or ranges therebetween of the repeated Y-displaying groups.

In some embodiments, the monomer of formula (II) comprises N-butanoyloxyalkyl methacrylamide. In some embodiments, the N-butanoyloxyalkyl methacrylamide monomer is 2-butanoyloxyethyl methacrylamide. In some embodiments, the copolymer is a block copolymer and comprises formula (VI):

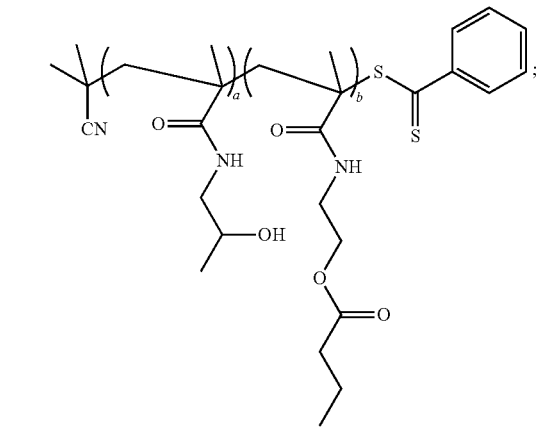

wherein a and b are independently 1-1000 (e.g., 10, 20, 30, 40, 50, 60, 70, 80, 90, 100, 125, 133, 150, 175, 200, 250, 300, 400, 500, 600, 700, 800, 900, 1000, or ranges therebetween). In some embodiments, the copolymer is a random copolymer and comprises formula (V):

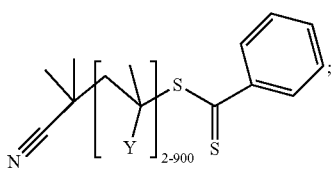

wherein each Y is independently selected from (i) the side chain of polyHPMA:

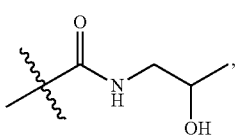 [SMILES: *C(=O)NCC(C)O]

and (ii) the side chain of poly(2-butanoyloxyethyl methacrylamide). In some embodiments, there are 2, 5, 10, 20, 30, 40, 50, 75, 100, 125, 150, 175 200, 250, 300, 350, 400, 450, 500, 550, 600, 650, 700, 750, 800, 850, 900, or ranges therebetween of the repeated Y-displaying groups.

In some embodiments, the monomer of formula (II) comprises an N-butanoyloxyalkyl methacrylate. In some embodiments, the N-butanoyloxyalkyl methacrylate monomer is an 2-butanoyloxyethyl methacrylate. In some embodiments, the copolymer is a block copolymer and comprises formula (VII):

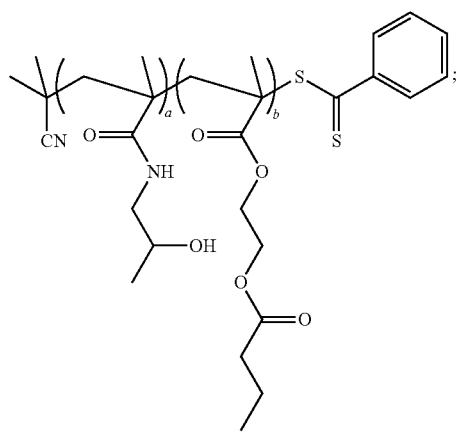

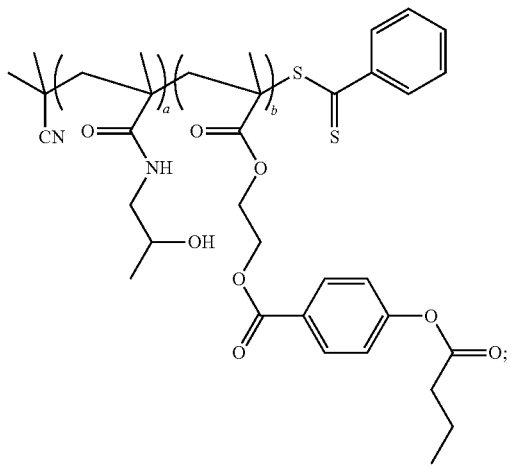

wherein a and b are independently 1-1000 (e.g., 10, 20, 30, 40, 50, 60, 70, 80, 90, 100, 125, 133, 150, 175, 200, 250, 300, 400, 500, 600, 700, 800, 900, 1000, or ranges therebetween). In some embodiments, the copolymer is a random copolymer and comprises formula (V):

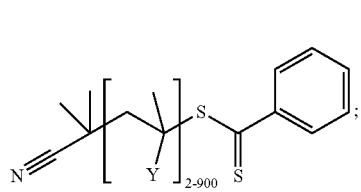

wherein a and b are independently 1-1000 (e.g., 10, 20, 30, 40, 50, 60, 70, 80, 90, 100, 125, 133, 150, 175, 200, 250, 300, 400, 500, 600, 700, 800, 900, 1000, or ranges therebetween). In some embodiments, the copolymer is a random copolymer and comprises formula (V):

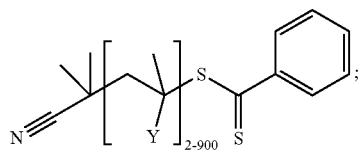

wherein each Y is independently selected from (i) the side chain of polyHPMA:

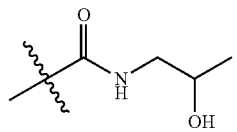

wherein each Y is independently selected from (i) the side chain of polyHPMA:

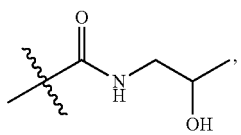 [SMILES: *C(=O)NCC(C)O]

and (ii) the side chain of poly(2-(4-butanoyloxybenzoyloxy) ethyl methacrylate):

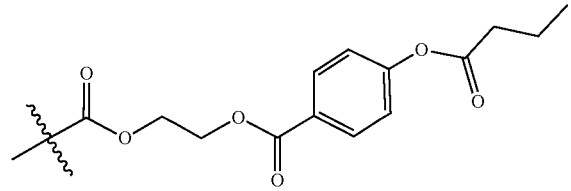

and (ii) the side chain of poly(2-butanoyloxyethyl methacrylate). In some embodiments, there are 2, 5, 10, 20, 30, 40, 50, 75, 100, 125, 150, 175, 200, 250, 300, 350, 400, 450, 500, 550, 600, 650, 700, 750, 800, 850, 900, or ranges therebetween of the repeated Y-displaying groups.

In some embodiments, the monomer of formula (II) comprises an N-(4-butanoyloxybenzoyloxy)alkyl methacrylate. In some embodiments, the N-(4-butanoyloxybenzoyloxy)alkyl methacrylate monomer is 2-(4-butanoyloxybenzoyloxy)ethyl methacrylate. In some embodiments, the copolymer is a block copolymer and comprises formula (VIII):

In some embodiments, there are 2, 5, 10, 20, 30, 40, 50, 75, 100, 125, 150, 175, 200, 250, 300, 350, 400, 450, 500, 550, 600, 650, 700, 750, 800, 850, 900, or ranges therebetween of the repeated Y-displaying groups.

In some embodiments, the monomer of formula (II) comprises an N-(4-butanoyloxybenzoyloxy)alkyl methacrylamide. In some embodiments, the N-(4-butanoyloxybenzoyloxy)alkyl methacrylamide monomer is 2-(4-butanoyloxybenzoyloxy)ethyl methacrylamide. In some embodiments, the copolymer is a block copolymer and comprises formula (IX):

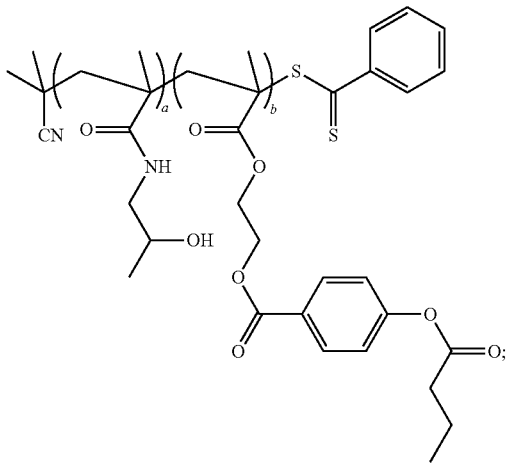

wherein a and b are independently 1-1000 (e.g., 10, 20, 30, 40, 50, 60, 70, 80, 90, 100, 125, 133, 150, 175, 200, 250, 300, 400, 500, 600, 700, 800, 900, 1000, or ranges therebetween). In some embodiments, the copolymer is a random copolymer and comprises formula (V):

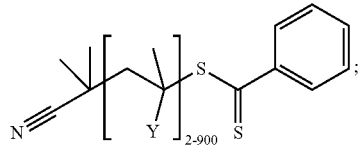

wherein each Y is independently selected from (i) the side chain of polyHPMA:

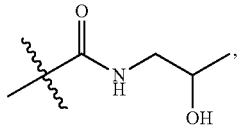 [SMILES: *C(=O)NCC(C)O]

and (ii) the side chain of poly(2-(4-butanoyloxybenzoyloxy) ethyl methacrylamide):

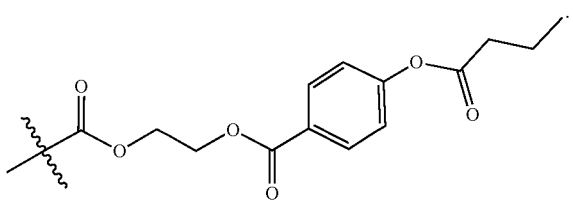 [SMILES: *C(=O)OCCCOC(=O)C1=CCC=C(OC(=O)CCC)C=C1]

In some embodiments, there are 2, 5, 10, 20, 30, 40, 50, 75, 100, 125, 150, 175, 200, 250, 300, 350, 400, 450, 500, 550, 600, 650, 700, 750, 800, 850, 900, or ranges therebetween of the repeated Y-displaying groups.

In some embodiments, provided herein are supramolecular assemblies of the copolymers described herein. In some embodiments, the supramolecular assembly is a micelle or nanoparticle.

In some embodiments, provided herein are pharmaceutical compositions comprising the supramolecular assemblies or copolymers described herein and a pharmaceutically-acceptable carrier.

In some embodiments, provided herein are foods or nutraceutical compositions comprising the supramolecular assemblies or copolymers described herein.

In some embodiments, provided herein are methods comprising administering to a subject a pharmaceutical composition, food, or nutraceutical composition described herein. In some embodiments, the method is performed to treat or prevent a disease or condition. In some embodiments, the disease or condition is selected from the group consisting of autoimmune diseases, allergies, inflammatory conditions, infections, metabolic disorders, diseases of the central nervous system, colon cancer, diabetes, autism spectrum disorders.

In some embodiments, provided herein are methods of synthesizing or manufacturing a copolymer, supramolecular assembly, pharmaceutical composition, food, and/or nutraceutical composition described herein.

In some embodiments, provided herein is the use of a copolymer, supramolecular assembly, pharmaceutical composition, food, and/or nutraceutical composition described herein for the treatment or prevention of a disease or condition.

BRIEF DESCRIPTION OF THE DRAWINGS

FIG. 20: Comparison of pHPMA-b-pBMA formulations as characterized by GPC, NMR, and DLS.

DEFINITIONS

Figure 1:
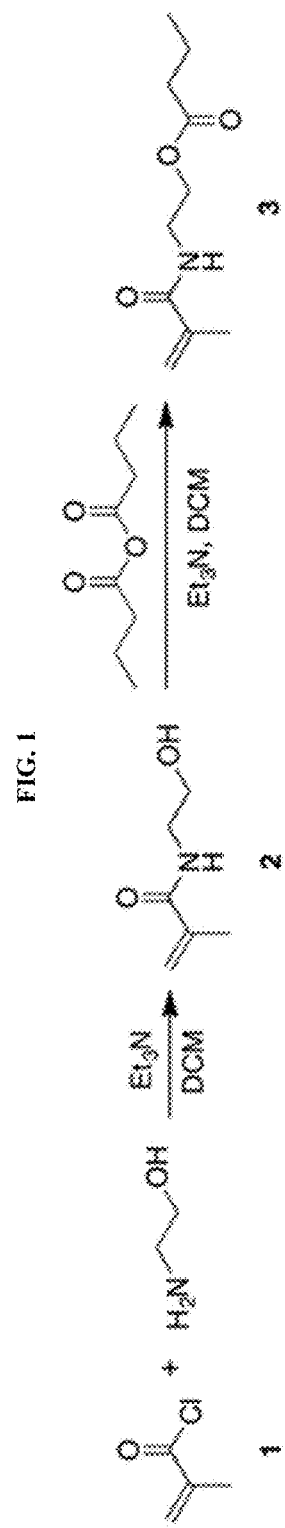
FIG. 1: Synthesis of N-oxyalkyl methacrylamide monomer with pharmaceutically-active small molecule
Figure 2A:
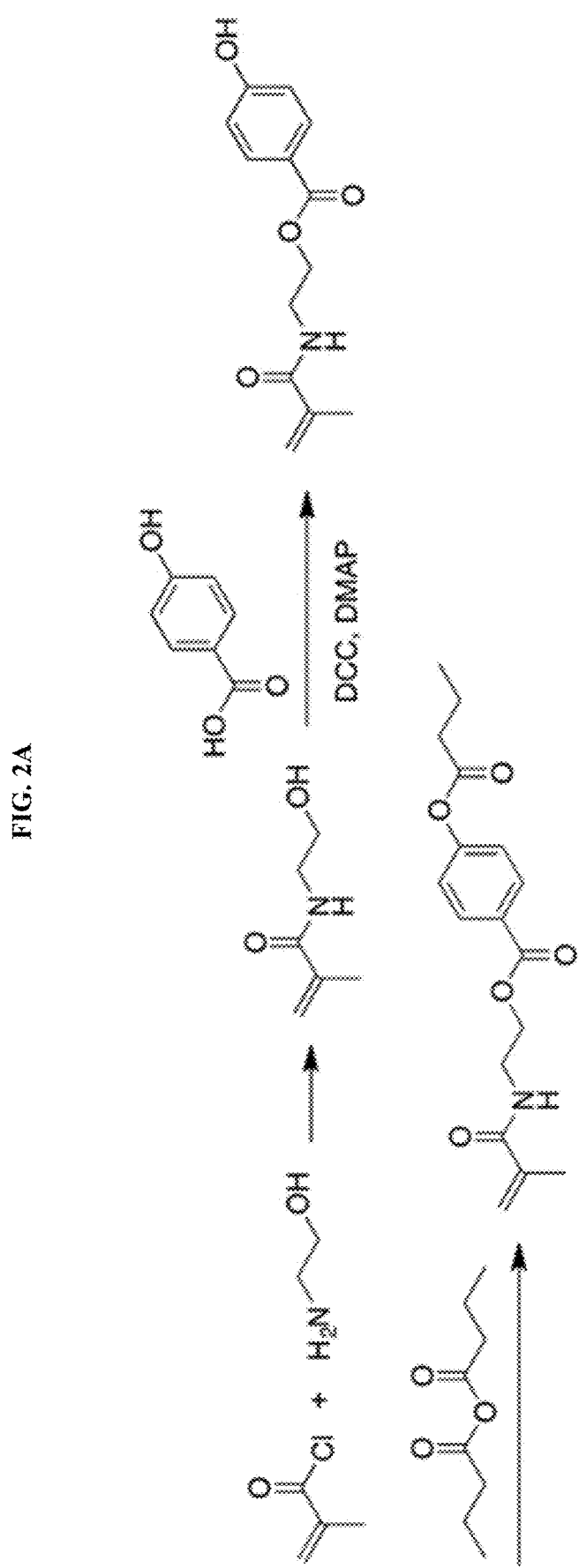
FIG. 2A-B: Synthesis of (A) 2-(4-hydroxybenzoyloxy) alkyl methacrylamide) and (B) 2-(4-hydroxybenzoyloxy) alkyl methacrylate monomers with pharmaceutically-active small molecule.
Figure 2B:
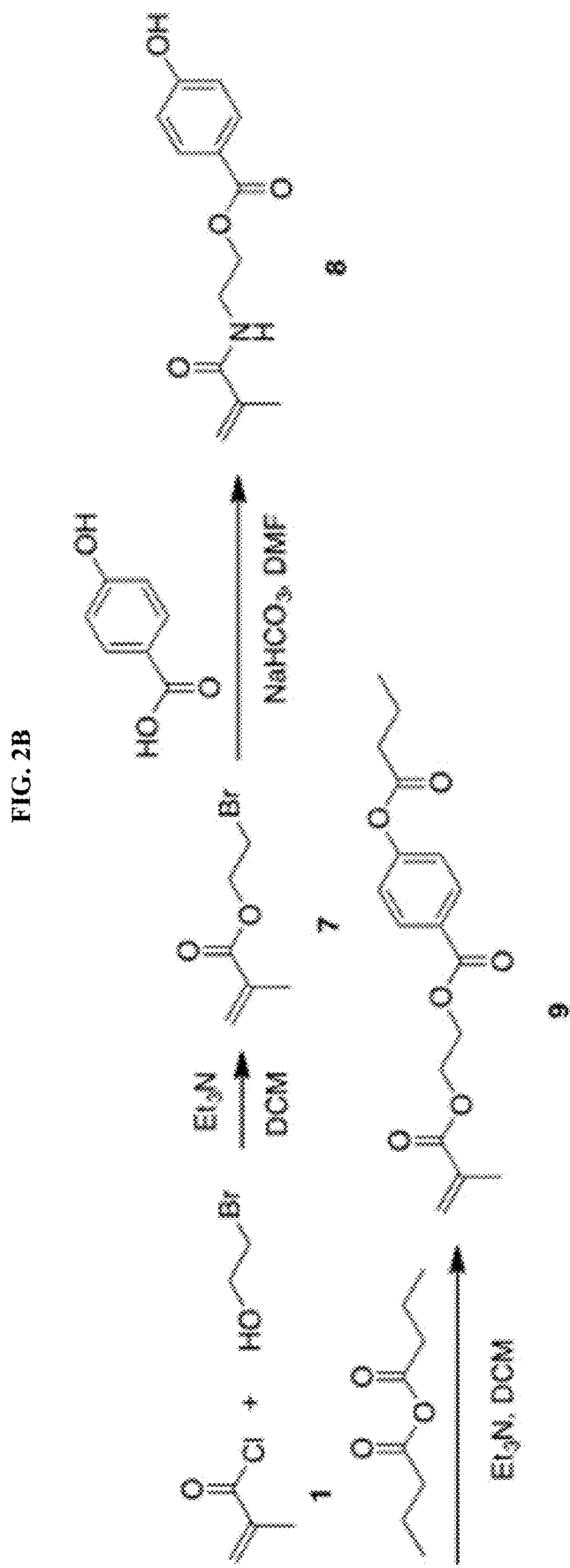
Figure 3:
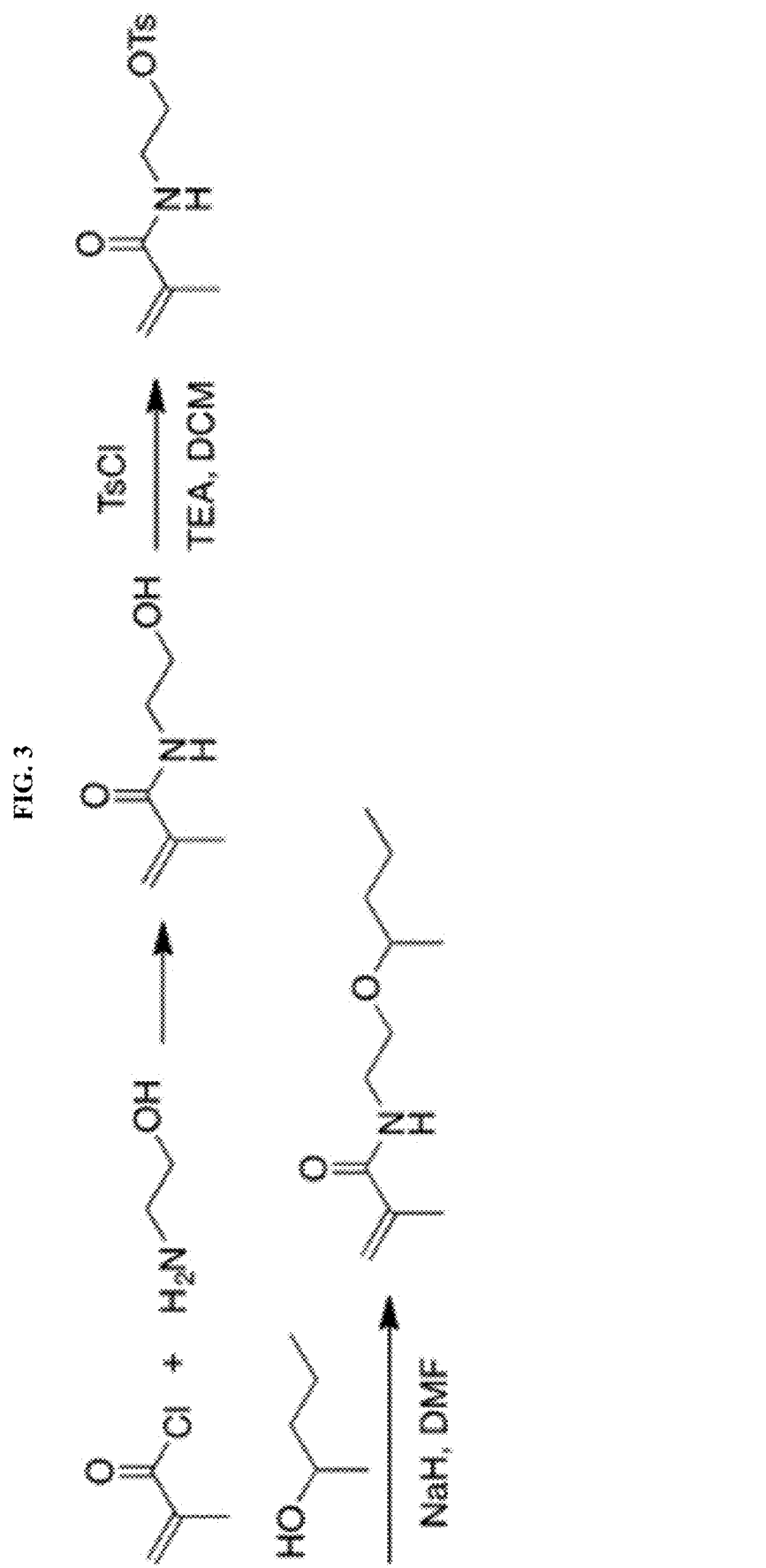
FIG. 3: Synthesis of the monomer for the control vehicle.
Figure 4:
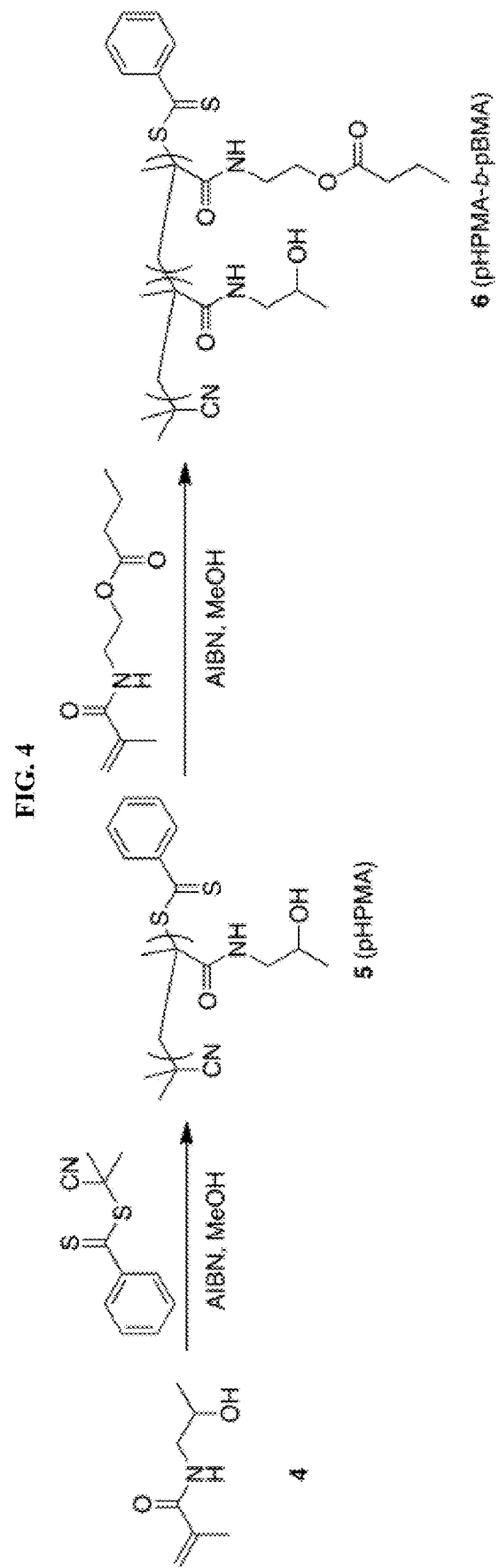
FIG. 4: Synthesis of the block copolymer pHPMA-b-pBMA.
Figure 5:
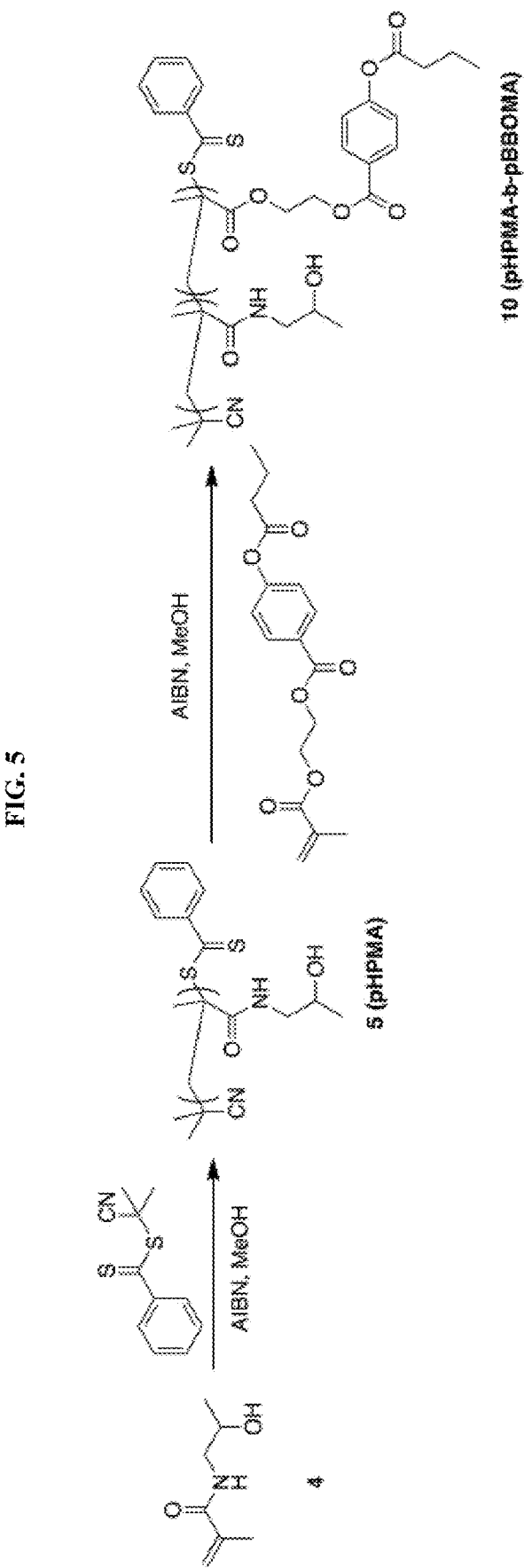
FIG. 5: Synthesis of the block copolymer pHIPMA-b-pBBOMA.
Figure 6:
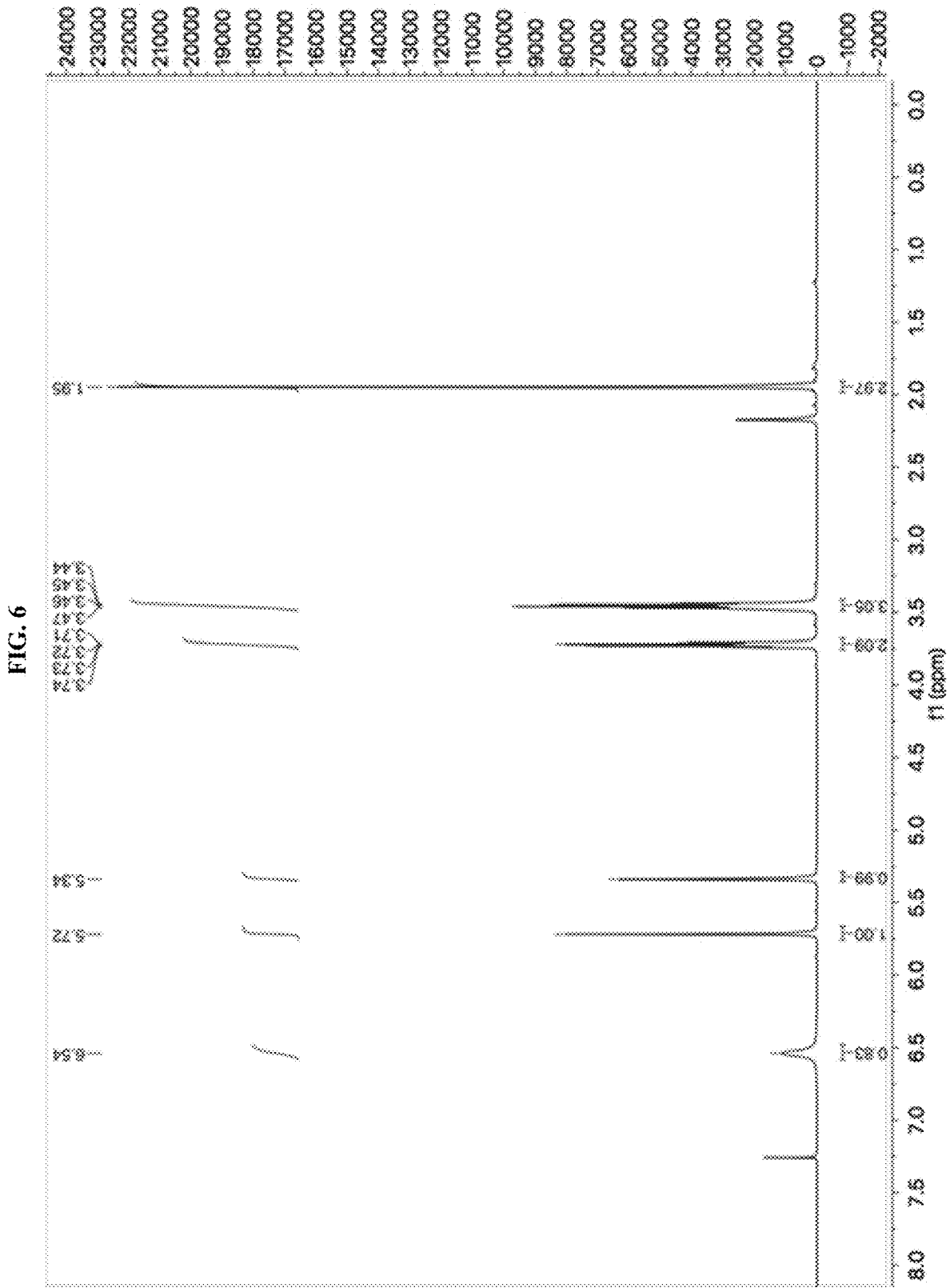
FIG. 6: $^1$H-NMR of N-(2-hydroxyethyl) methacrylamide (2) (500 MHz, CDCl$_3$).
Figure 7:
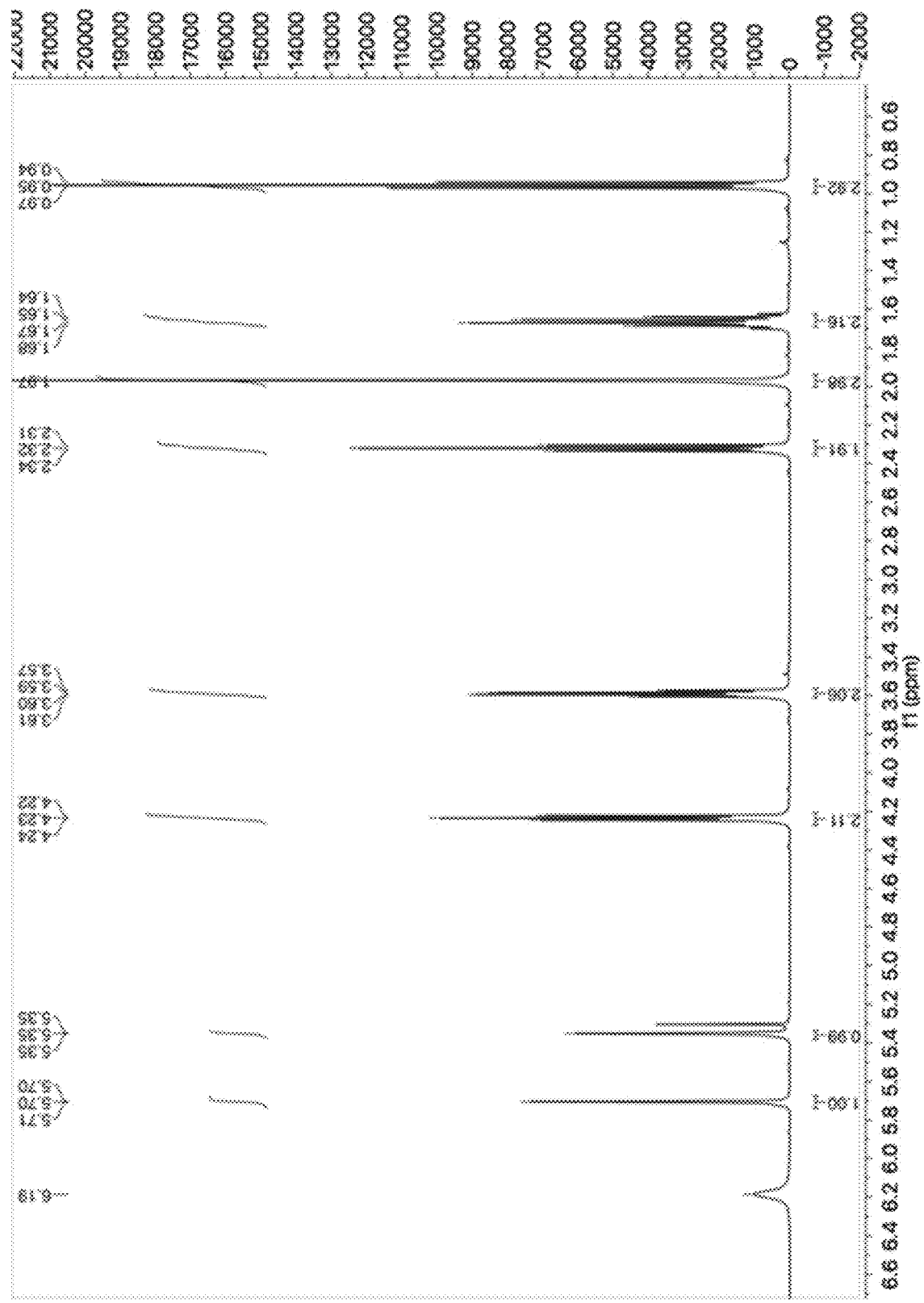
FIG. 7: $^1$H-NMR of N-butanoyloxyethyl methacrylamide (3) (500 MHz, CDCl$_3$).
Figure 8:
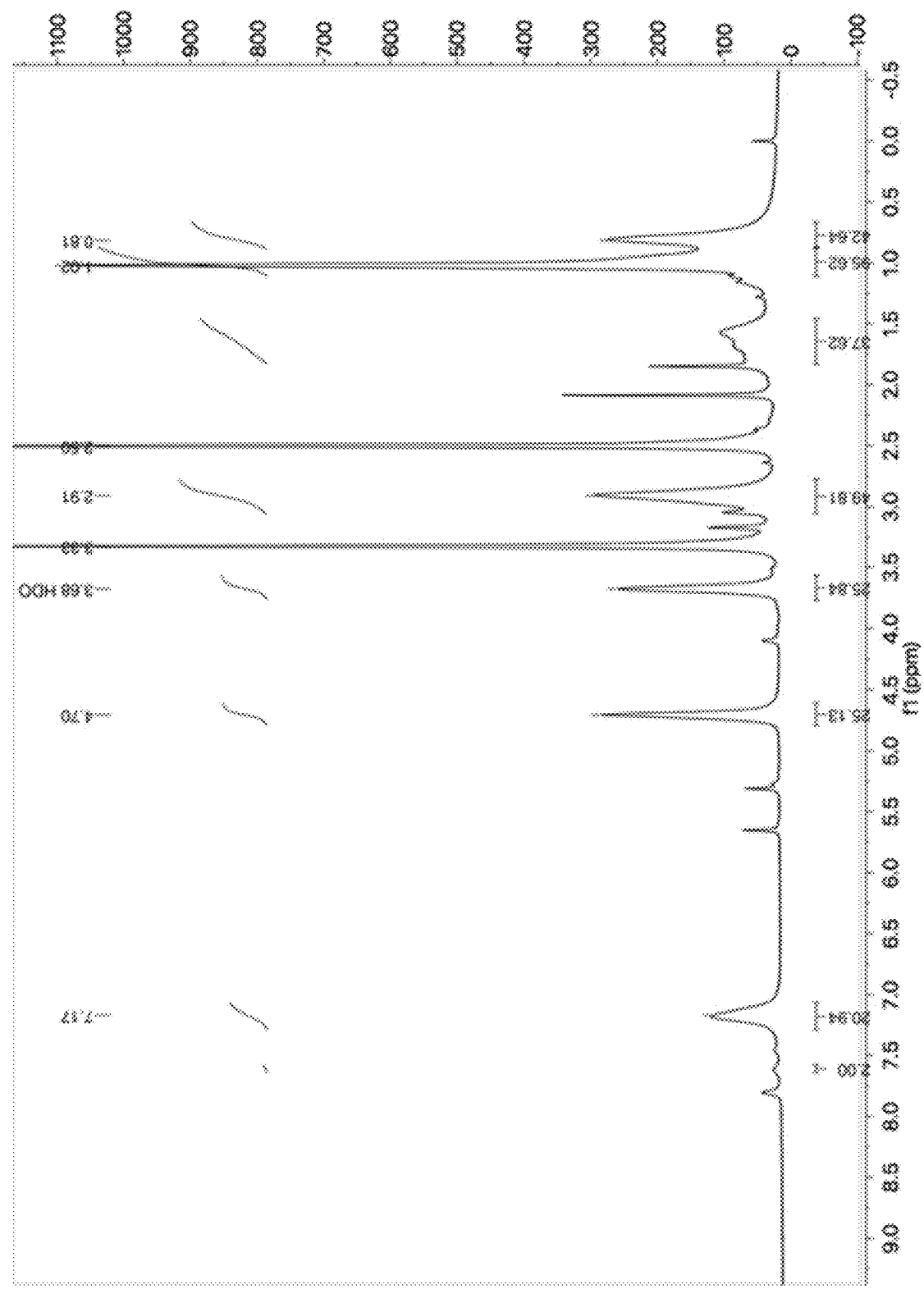
FIG. 8: $^1$H-NMR of pHPMA (5) (500 MHz, DMSO-d6).
Figure 9:
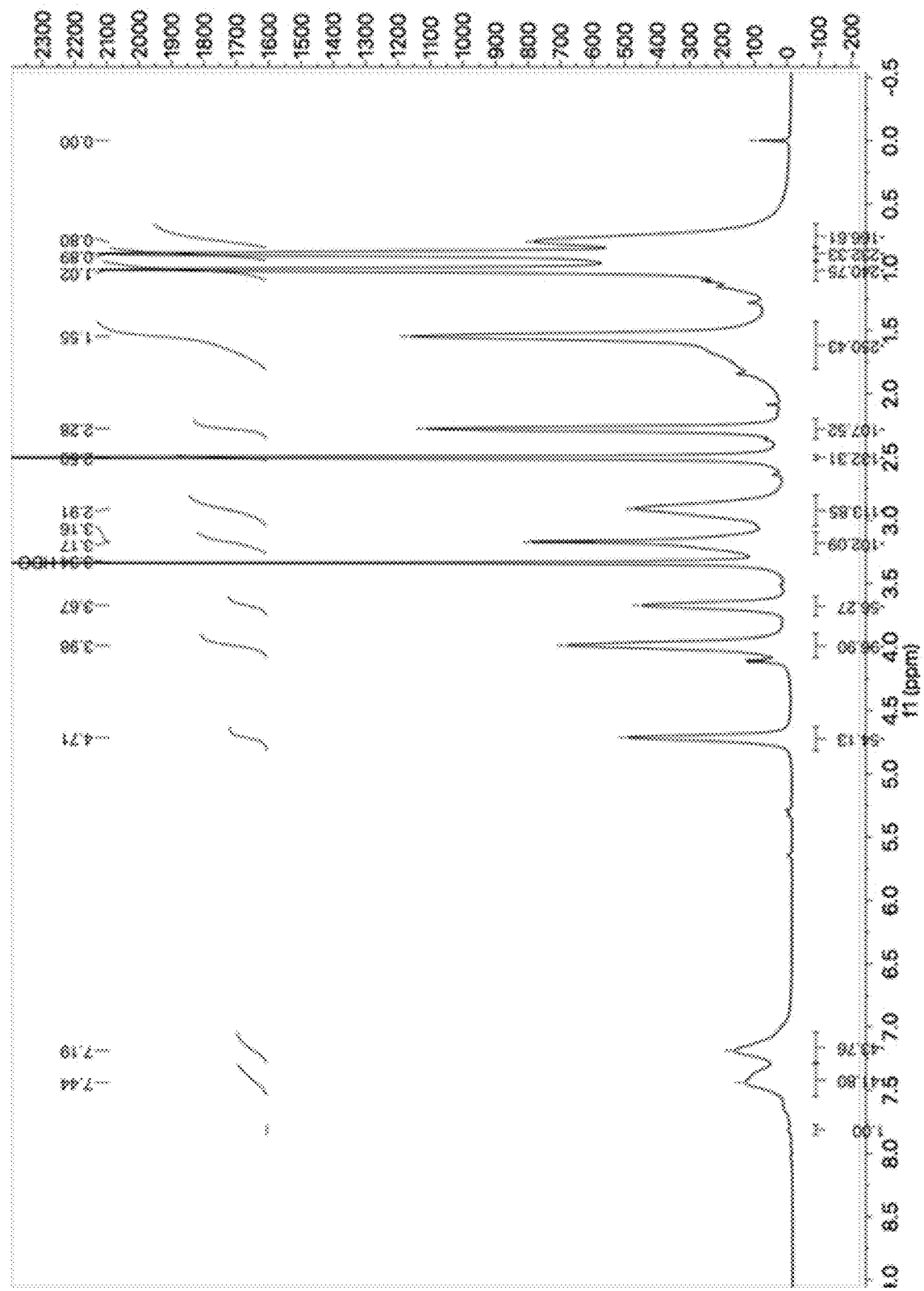
FIG. 9: $^1$H-NMR of pHPMA-b-pBMA (6) (500 MHz, DMSO-d6).
Figure 10:
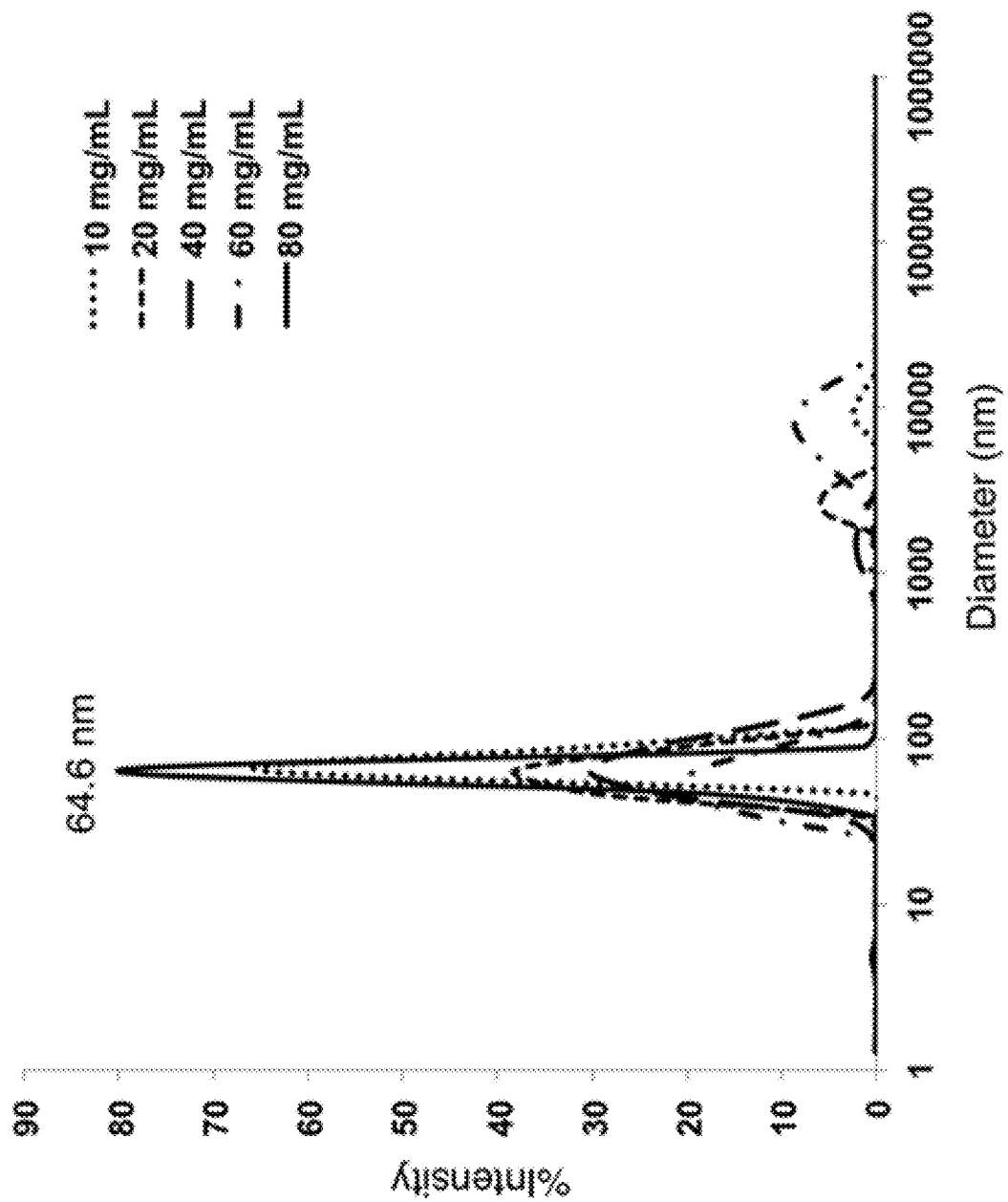
FIG. 10: Dynamic light scattering data of copolymer pHPMA-b-pBMA (HPMA/BMA=0.71) solutions at different concentrations. At 80 mg/mL, the solution showed a sharp peak with the diameter of 64.6 nm.
Figure 11:
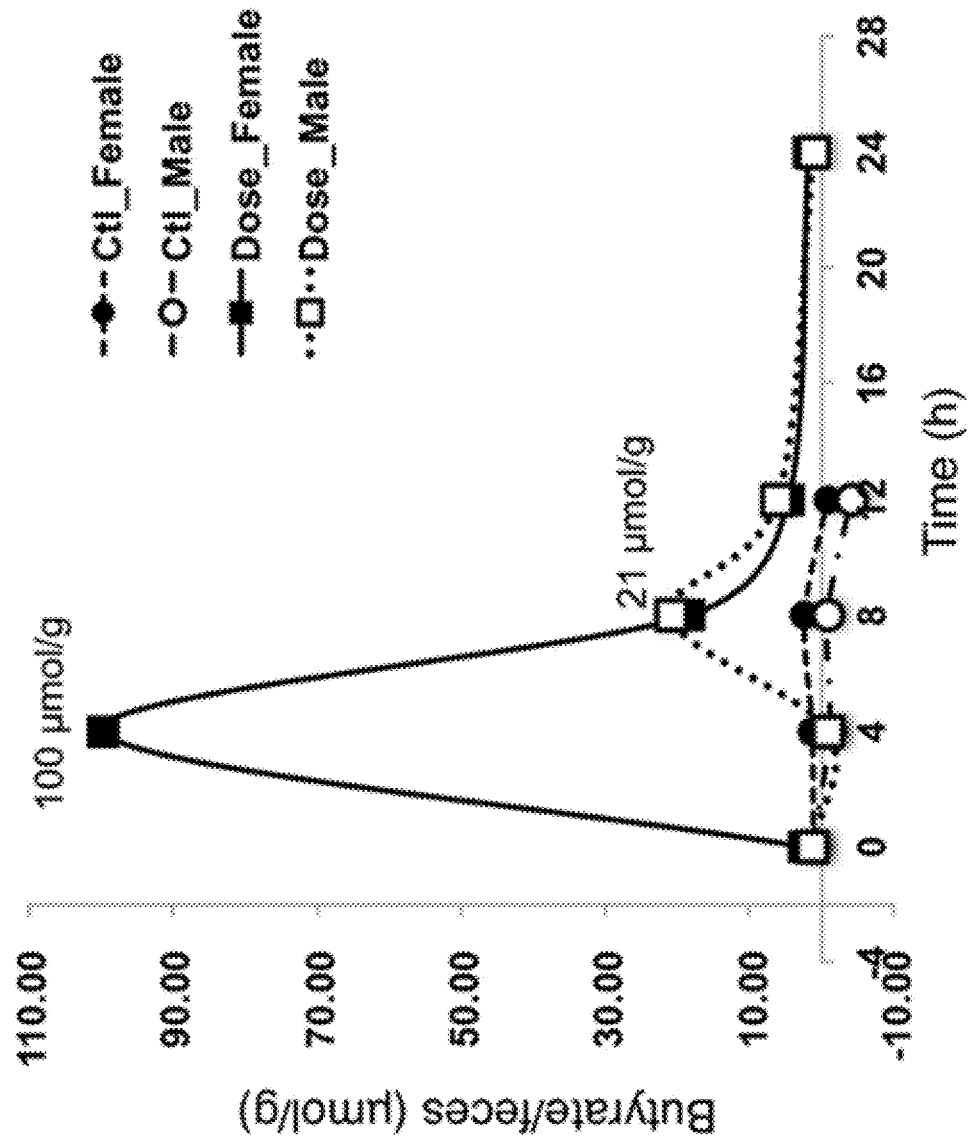
FIG. 11: Concentration of butyrate in feces for one day after oral administration of block copolymer at time 0.
Figure 12:
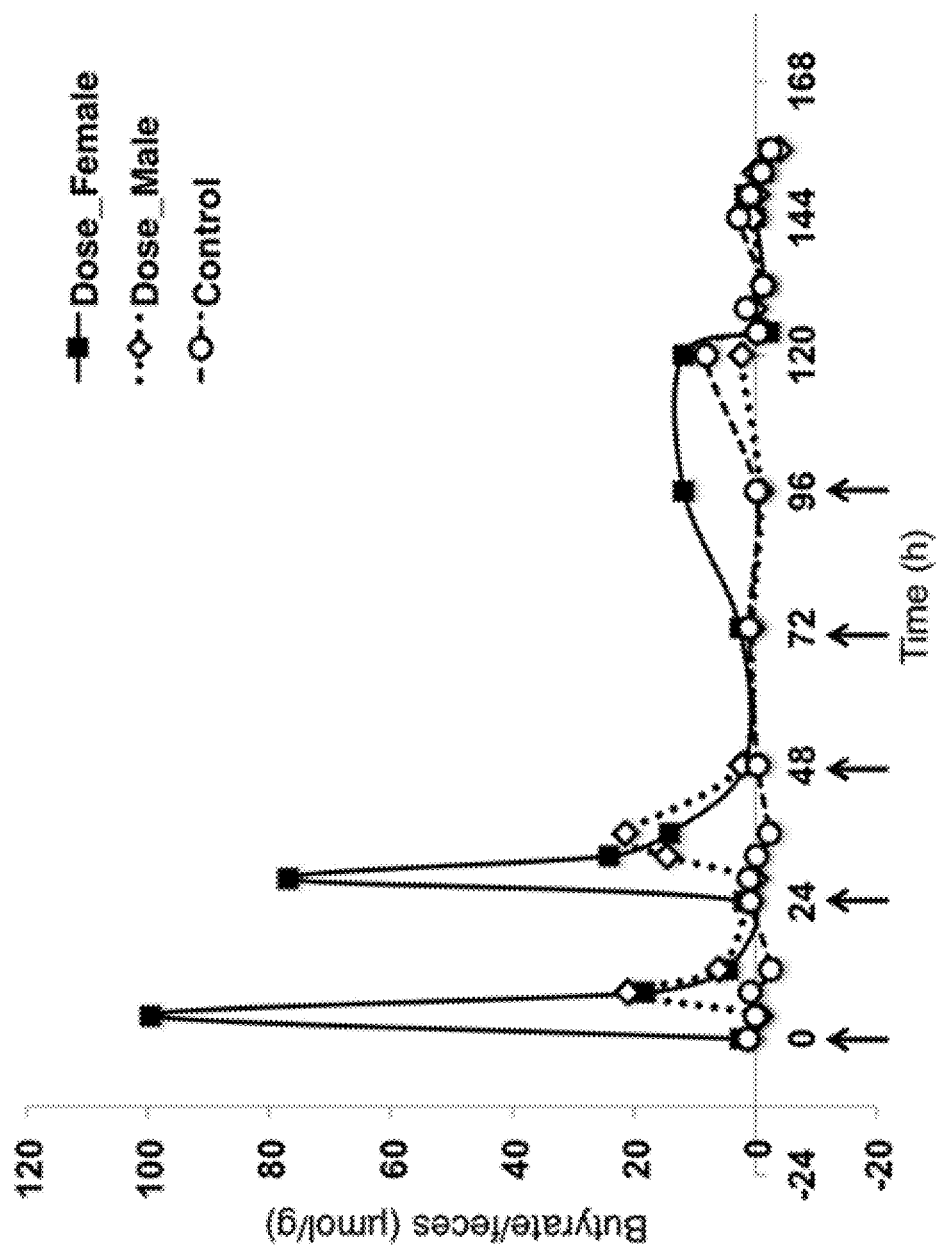
FIG. 12: Concentration of butyrate in feces after daily oral administration of block copolymer for five days, followed by block copolymer withdrawal for two days.
Figure 13:
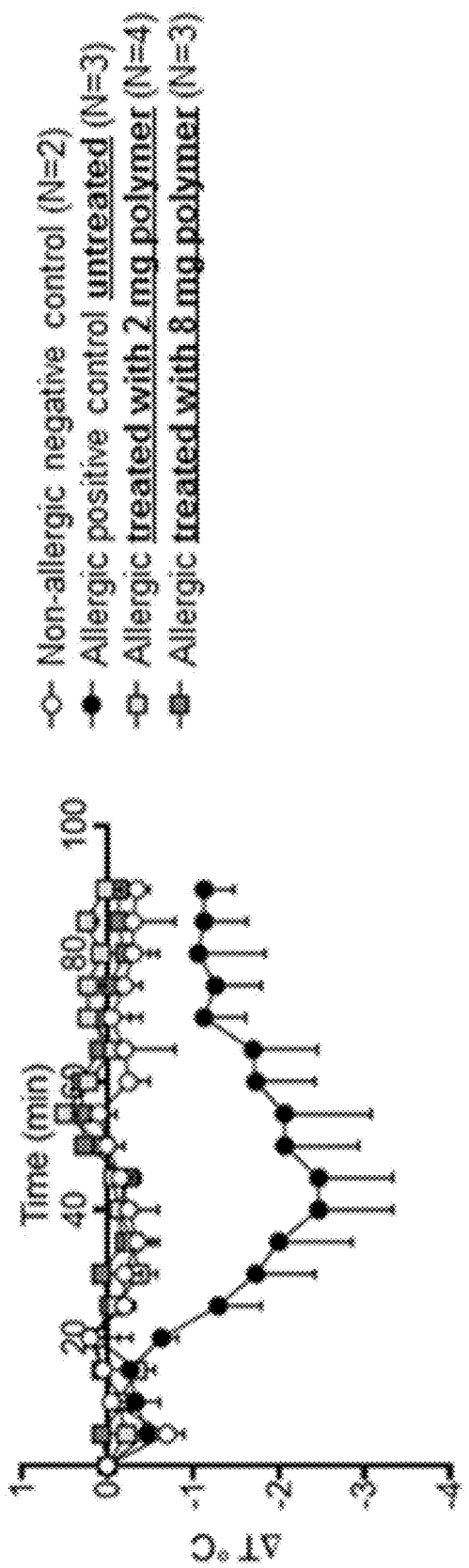
FIG. 13: Core body temperature over time after challenge with peanut protein with and without polymer treatment. "Allergic positive control" or "allergic" means an allergy to peanuts was induced in mice by sensitization via intragastric gavage with 5 mg peanut protein+10 µg cholera toxin as adjuvant. "Non-allergic negative control" means 10 μg cholera toxin adjuvant only was used and did not induce an allergy.
Figure 14:
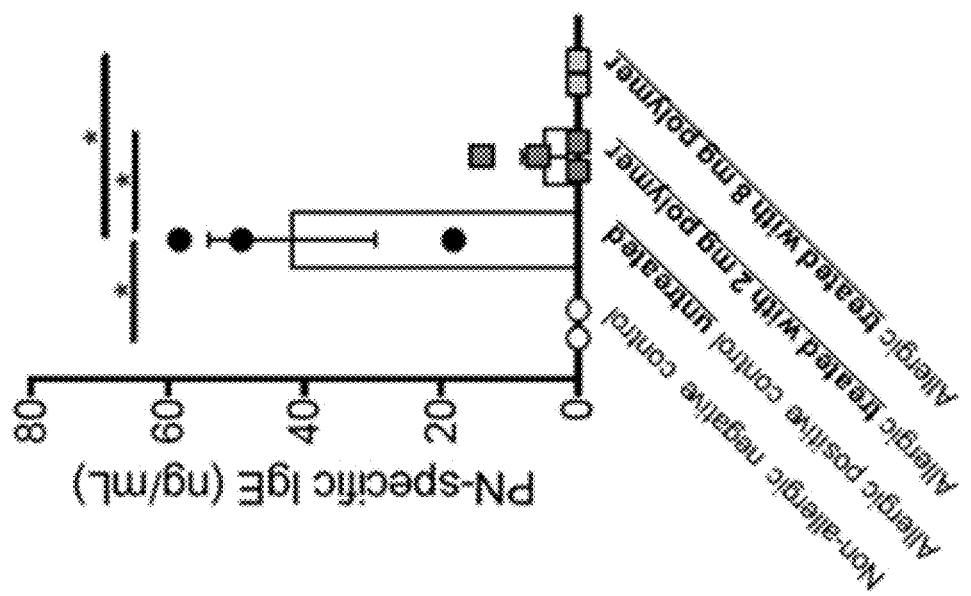
FIG. 14: Concentration of peanut-specific IgE in serum 24 hours after challenge with peanut protein with and without polymer treatment. "Allergic positive control" or "allergic" means an allergy to peanuts was induced in mice by sensitization via intragastric gavage with 5 mg peanut protein+10 μg cholera toxin as adjuvant. "Non-allergic negative control" means 10 μg cholera toxin adjuvant only was used and did not induce an allergy.
Figure 15:
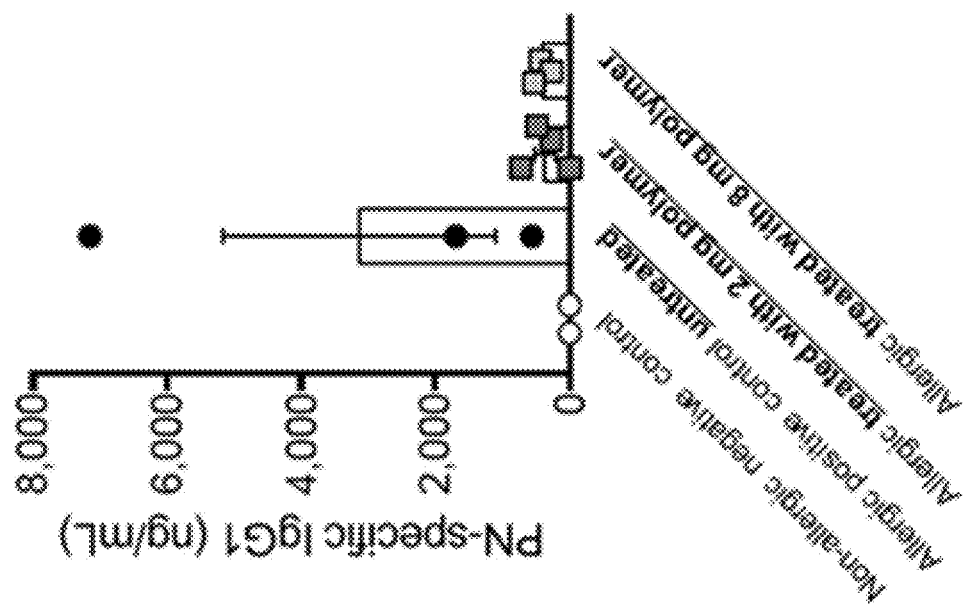
FIG. 15: Concentration of peanut-specific IgG1 in serum 24 hours after challenge with peanut protein with and without polymer treatment. "Allergic positive control" or "allergic" means an allergy to peanuts was induced in mice by sensitization via intragastric gavage with 5 mg peanut protein+10 μg cholera toxin as adjuvant. "Non-allergic negative control" means 10 μg cholera toxin adjuvant only was used and did not induce an allergy.
Figure 16:
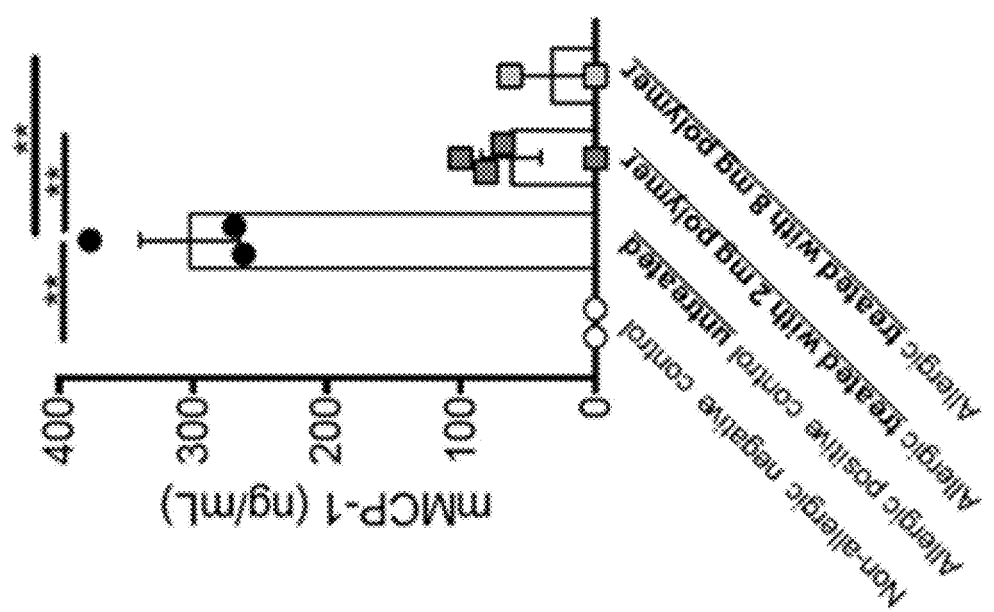
FIG. 16: Concentration of mouse mast cell protease-1 in serum 90 minutes after challenge with peanut protein with and without polymer treatment. "Allergic positive control" or "allergic" means an allergy to peanuts was induced in mice by sensitization via intragastric gavage with 5 mg peanut protein+10 μg cholera toxin as adjuvant. "Non-allergic negative control" means 10 μg cholera toxin adjuvant only was used and did not induce an allergy.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a block copolymer" is a reference to one or more block copolymers and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "short-chain fatty acid" ("SCFA") refers to a carboxylic acid attached to an aliphatic chain, which is either saturated or unsaturated, the aliphatic chain being 12 carbons or less in length.

As used herein the term "fatty acid derivative" (specifically "SCFA derivative") refers to a small molecular compounds that are obtained by making simple modifications (e.g., amidation, methylation, halogenation, etc.) to fatty acid molecules (e.g., SCFA molecules). For example, butyramide, D- or L-amino-n-butyric acid, alpha- or beta-amino-n-butyric acid, arginine butyrate, butyrin, phenyl butyrates (e.g., 4-, 3-, 2-), dimethylbutyrate, 4-halobutyrates (e.g., fluoro-, chloro-, bromo-, iodo-), 3-halobutyrates (e.g., fluoro-, chloro-, bromo-, iodo-), 2-halobutyrates (e.g., fluoro-, chloro-, bromo-, iodo-), oxybutyrate, and methyl-butyrates are exemplary butyrate derivatives. Other butyrate derivatives and similar derivatives of other SCFAs are within the scope of the SCFA derivatives described herein.

As used herein, the term "copolymer" refers to a polymer formed from two or more different monomer subunits. Exemplary copolymers include alternating copolymers, random copolymers, block copolymers, etc.

As used herein, the term "block copolymer" refers to copolymers wherein the repeating subunits are polymeric blocks, i.e. a polymer of polymers. In a copolymer of blocks A and B, A and B each represent polymeric entities themselves, obtained by the polymerization of monomers. Exemplary configurations of such block copolymers include branched, star, di-block, tri-block and so on.

As used herein, the term "supramolecular" (e.g., "supramolecular assembly") refers to the non-covalent interactions between molecules and/or solution (e.g., polymers, macromolecules, etc.) and the multicomponent assemblies, complexes, systems, and/or fibers that form as a result.

As used herein, the term "pharmaceutically acceptable carrier" refers to non-toxic solid, semisolid, or liquid filler, diluent, encapsulating material, formulation auxiliary, excipient, or carrier conventional in the art for use with a therapeutic agent for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. A "pharmaceutical composition" typically comprises at least one active agent (e.g., the copolymers described herein) and a pharmaceutically acceptable carrier.

As used herein, the term "effective amount" refers to the amount of a composition (e.g., pharmaceutical composition) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., pharmaceutical compositions of the present invention) to a subject or in vivo, in vitro, or ex vivo cells, tissues, and organs. Exemplary routes of administration to the human body can be through the eyes (e.g., intraocularly, intravitreally, periocularly, ophthalmic, etc.), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the terms "co-administration" and "co-administer" refer to the administration of at least two agent(s) or therapies to a subject. In some embodiments, the co-administration of two or more agents or therapies is concurrent (e.g., in the same or separate formulations). In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "nanoparticles" refers to particles having mean dimensions (e.g., diameter, width, length, etc.) of less than 1 μm (e.g., <500 nm ("sub-500-nm nanoparticles"), <100 nm ("sub-100-nm nanoparticles"), <50 nm ("sub-50-nm nanoparticles").

As used herein, the term "biocompatible" refers to materials, compounds, or compositions means that do not cause or elicit significant adverse effects when administered to a subject. Examples of possible adverse effects that limit biocompatibility include, but are not limited to, excessive inflammation, excessive or adverse immune response, and toxicity.

As used herein, the term "biostable" refers to compositions or materials that do not readily break-down or degrade in a physiological or similar aqueous environment. Conversely, the term "biodegradable" refers herein to compositions or materials that readily decompose (e.g., depolymerize, hydrolyze, are enzymatically degraded, disassociate, etc.) in a physiological or other environment.

As used herein, the term "substituted" refers to a group (e.g., alkyl, etc.) that is modified with one or more additional group(s). Non-limiting examples of substituents include, for example: halogen, hydroxy, oxo ($=O$), thioxo ($=S$), cyano (—CN), nitro (—$NO_2$), imino ($=N$—H), oximo ($=N$—OH), hydrazino ($=N$—$NH_2$), $NH_2$)—$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$_tR^a$ (where t is 1 or 2), —$R^b$—S(O)$_tR^a$ (where t is 1 or 2), —$R^b$—S(O)$_tOR^a$ (where t is 1 or 2), and —$R^b$—S(O)$_tN(R^a)_2$ (where t is 1 or 2); and alkyl, alkenyl, alkynyl, each of which may be optionally substituted by halogen, oxo ($=O$), thioxo ($=S$), cyano (—CN), nitro (—$NO_2$), imino ($=N$—H), oximo ($=N$—OH), hydrazine ($=N$—$NH_2$), —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$_tR^a$ (where t is 1 or 2), —$R^b$—S(O)$_tR^a$ (where t is 1 or 2), —$R^b$—S(O)$_tOR^a$ (where t is 1 or 2), —$R^b$—S(O)$_tN(R^a)_2$ (where t is 1 or 2), carbocycle and heterocycle; wherein each $R^a$ is independently selected from hydrogen, alkyl, alkenyl, alkynyl, carbocycle and heterocycle, wherein each $R^a$, valence permitting, may be optionally substituted with halogen, oxo ($=O$), thioxo ($=S$), cyano (—CN), nitro (—$NO_2$), imino ($=N$—H), oximo ($=N$—OH), hydrazine ($=N$—$NH_2$), —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$_tR^a$ (where t is 1 or 2), —$R^b$—S(O)$_tR^a$ (where t is 1 or 2), —$R^b$—S(O)$_tOR^a$ (where t is 1 or 2) and —$R^b$—S(O)$_tN(R^a)_2$ (where t is 1 or 2); and wherein each $R^b$ is independently selected from a direct bond or a straight or branched alkylene, alkenylene, or alkynylene chain, and each $R^c$ is a straight or branched alkylene, alkenylene or alkynylene chain. Substituent groups may be selected from, but are not limited to: alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. A "substituted alkyl" encompasses alkynes and alkenes, in addition to alkanes displaying substituent moieties.

As used herein, the term "pseudo-random" refers to sequences or structures generated by processes in which no steps or measures have been taken to control the order of addition of monomers or components.

As used herein, the term "display" refers to the presentation of solvent-exposed functional group by a molecule, monomer, polymer, nanostructure or other chemical entity.

DETAILED DESCRIPTION OF THE INVENTION

Provided herein are polymer materials that find use in, for example, delivery of short-chain fatty acids. In particular, polymers are provided that form stable nanoscale structures and release their payload, for example, by cleavage of a covalent bond (e.g., via hydrolysis or enzymatic cleavage). The polymers are useful, for example, for delivery of payloads (e.g., SCFAs) to the intestine for applications in health and treatment of disease, and have broad applicability in diseases linked to changes in the human microbiota including inflammatory, autoimmune, allergic, metabolic, and central nervous system diseases, among others.

In some embodiments, provided herein are copolymers (e.g., block or random) of: hydrophilic monomers (or a block thereof) pendant-displaying methacrylamide or methacrylate monomers (or a block thereof). In some embodiments, methods are provided for the assembly of these copolymers into nanoparticles, micelles, or other delivery systems. In some embodiments, methods are provided for the administration of the copolymers, and delivery systems comprising such copolymers, for the treatment or prevention of various diseases and conditions. In particular, polymers are functionalized to deliver a pharmaceutically-relevant small molecule moiety (e.g., SCFA) relevant for treating human disease with a covalent bond that is broken (e.g., by hydrolysis or enzyme activity). In some embodiments, copolymers are obtained using reversible addition-fragmentation chain-transfer ("RAFT") polymerization of an appropriate monomer with an initiator.

In some embodiments, polymers are random copolymers comprising N-hydroxypropyl methacrylamide (HPMA) monomers. Other synthetic natural molecules or polymers may be used as hydrophilic monomers.

In some embodiments, an HPMA-(N-hydroxyethyl methacrylamide) copolymer is a copolymer (e.g., random copolymer) of HPMA monomers and N-hydroxyethyl methacrylamide monomers. A free HPMA terminus (e.g., not connected to the N-hydroxyethyl acrylamide block) may be one of a number of chemical groups, including but not limited to hydroxyl, methoxy, thiol, amine, maleimide, halogen, polymer chain transfer agents, protecting groups, drug, biomolecule, or tissue targeting moiety. Some or all N-hydroxyethyl methacrylamide monomers display a pharmaceutically-relevant small molecule covalently attached to the hydroxyethyl functional group. A preferred embodiment of the pharmaceutically-relevant small molecule is short- and medium-chain fatty acids ("SCFA" s) and their derivatives containing up to 12 carbon atoms in the chain, for example, between 3 and 10 carbon atoms in the chain. The chain may be linear or branched. Example SCFAs include, but are not limited to, acetate, propionate, iso-propionate, butyrate, iso-butyrate, and other SCFAs described herein, as well as derivatives thereof. A free SCFA terminus may be one of a number of chemical groups including but not limited to methyl, hydroxyl, methoxy, thiol, amine, N-alkyl amine, and others.

In some embodiments, an HPMA-(N-hydroxyethyl methacrylate) copolymer is a copolymer (e.g., random copolymer) of HPMA monomers and N-hydroxyethyl methacrylate monomers. A free HPMA terminus may be one of a number of chemical groups, including but not limited to hydroxyl, methoxy, thiol, amine, maleimide, halogen, polymer chain transfer agents, protecting groups, drug, biomolecule, or tissue targeting moiety. Some or all N-hydroxyethyl methacrylate monomers display a pharmaceutically-relevant small molecule covalently attached to the hydroxyethyl functional group. A preferred embodiment of the pharmaceutically-relevant small molecule is short- and medium-chain fatty acids ("SCFA" s) and their derivatives containing, for example, between 3 and 12 (e.g., 3, 4, 5, 6, 7, 8, 9, 10, 11, 12, or ranges therebetween) carbon atoms in the chain. The chain may be linear or branched. Example SCFAs include, but are not limited to, acetate, propionate, iso-propionate, butyrate, iso-butyrate, and other SCFAs described herein, as well as derivatives thereof. A free SCFA terminus may be one of a number of chemical groups including but not limited to methyl, hydroxyl, methoxy, thiol, amine, N-alkyl amine, and others.

In some embodiments, an HPMA-(N-(4-hydroxybenzoyloxy)alkyl methacrylate) copolymer is a copolymer (e.g., random copolymer) of HPMA monomers and N-(4-hydroxybenzoyloxy)alkyl methacrylate monomers. A free HPMA terminus may be one of a number of chemical groups, including but not limited to hydroxyl, methoxy, thiol, amine, maleimide, halogen, polymer chain transfer agents, protecting groups, drug, biomolecule, or tissue targeting moiety. Some or all N-(4-hydroxybenzoyloxy)alkyl methacrylate monomers display a pharmaceutically-relevant small molecule covalently attached to the hydroxyethyl functional group. A preferred embodiment of the pharmaceutically-relevant small molecule is short- and medium-chain fatty acids ("SCFA" s) and their derivatives containing, for example, between 3 and 12 (e.g., 3, 4, 5, 6, 7, 8, 9, 10, 11, 12, or ranges therebetween) carbon atoms in the chain. The chain may be linear or branched. Example SCFAs include, but are not limited to, acetate, propionate, iso-propionate, butyrate, iso-butyrate, and other SCFAs described herein, as well as derivatives thereof. A free SCFA terminus may be one of a number of chemical groups including but not limited to methyl, hydroxyl, methoxy, thiol, amine, N-alkyl amine, and others.

In some embodiments, an HPMA-(N-(4-hydroxybenzoyloxy)alkyl methacrylamide) copolymer is copolymer (e.g., random copolymer) of HPMA monomers and N-(4-hydroxybenzoyloxy)alkyl methacrylamide monomers. A free HPMA terminus may be one of a number of chemical groups, including but not limited to hydroxyl, methoxy, thiol, amine, maleimide, halogen, polymer chain transfer agents, protecting groups, drug, biomolecule, or tissue targeting moiety. Some or all N-(4-hydroxybenzoyloxy)alkyl methacrylamide monomers display a pharmaceutically-relevant small molecule covalently attached to the hydroxyethyl functional group. A preferred embodiment of the pharmaceutically-relevant small molecule is short- and medium-chain fatty acids ("SCFA" s) and their derivatives containing, for example, between 3 and 12 (e.g., 3, 4, 5, 6, 7, 8, 9 10, 11, 12, or ranges therebetween) carbon atoms in the chain. The chain may be linear or branched. Example SCFAs include, but are not limited to, acetate, propionate, iso-propionate, butyrate, iso-butyrate, and other SCFAs described herein, as well as derivatives thereof. A free SCFA terminus may be one of a number of chemical groups including but not limited to methyl, hydroxyl, methoxy, thiol, amine, N-alkyl amine, and others.

In some embodiments, polymers are block copolymers comprising poly(N-hydroxypropyl methacrylamide) as a hydrophilic block. Other synthetic natural molecules or polymers may be used as hydrophilic blocks.

In some embodiments, an HPMA-(N-hydroxyethyl methacrylamide) copolymer is composed of the hydrophilic polyHPMA block covalently attached to the N-hydroxyethyl methacrylamide block. The free HPMA terminus not connected to the N-hydroxyethyl methacrylamide block may be one of a number of chemical groups, including but not limited to hydroxyl, methoxy, thiol, amine, maleimide, halogen, polymer chain transfer agents, protecting groups, drug, biomolecule, or tissue targeting moiety. The N-hydroxyethyl methacrylamide block displays a pharmaceutically-relevant small molecule covalently attached to the hydroxyethyl functional group. A preferred embodiment of the pharmaceutically-relevant small molecule is short- and medium-chain fatty acids ("SCFA" s) and their derivatives containing, for example, between 3 and 12 (e.g., 3, 4, 5, 6, 7, 8, 9 10, 11, 12, or ranges therebetween) carbon atoms in the chain. The chain may be linear or branched. Example SCFAs include, but are not limited to, acetate, propionate, iso-propionate, butyrate, iso-butyrate, and other SCFAs described herein, as well as derivatives thereof. The free SCFA terminus not connect to the N-hydroxyethyl methacrylamide block may be one of a number of chemical groups including but not limited to methyl, hydroxyl, methoxy, thiol, amine, N-alkyl amine, and others.

In some embodiments, an HPMA-(N-hydroxyethyl methacrylate) copolymer is composed of the hydrophilic polyHPMA block covalently attached to the N-hydroxyethyl methacrylate block. The free HPMA terminus not connected to the N-hydroxyethyl methacrylate block may be one of a number of chemical groups, including but not limited to hydroxyl, methoxy, thiol, amine, maleimide, halogen, polymer chain transfer agents, protecting groups, drug, biomolecule, or tissue targeting moiety. The N-hydroxyethyl methacrylate block displays a pharmaceutically-relevant small molecule covalently attached to the hydroxyethyl functional group. A preferred embodiment of the pharmaceutically-relevant small molecule is short- and medium-chain fatty acids ("SCFA" s) and their derivatives containing, for example, between 3 and 12 (e.g., 3, 4, 5, 6, 7, 8, 9 10, 11, 12, or ranges therebetween)carbon atoms in the chain. The chain may be linear or branched. Example SCFAs include, but are not limited to, acetate, propionate, iso-propionate, butyrate, iso-butyrate, and other SCFAs described herein, as well as derivatives thereof. The free SCFA terminus not connect to the N-hydroxyethyl methacrylate block may be one of a number of chemical groups including but not limited to methyl, hydroxyl, methoxy, thiol, amine, N-alkyl amine, and others.

In some embodiments, an HPMA-(N-(4-hydroxybenzoyloxy)alkyl methacrylate) copolymer is composed of the hydrophilic polyHPMA block covalently attached to the N-(4-hydroxybenzoyloxy)alkyl methacrylate block. The free HPMA terminus not connected to the N-(4-hydroxybenzoyloxy)alkyl methacrylate block may be one of a number of chemical groups, including but not limited to hydroxyl, methoxy, thiol, amine, maleimide, halogen, polymer chain transfer agents, protecting groups, drug, biomolecule, or tissue targeting moiety. The N-(4-hydroxybenzoyloxy)alkyl methacrylate block displays a pharmaceutically-relevant small molecule covalently attached to the hydroxyethyl functional group. A preferred embodiment of the pharmaceutically-relevant small molecule is short- and medium-chain fatty acids ("SCFA" s) and their derivatives containing, for example, between 3 and 12 (e.g., 3, 4, 5, 6, 7, 8, 9 10, 11, 12, or ranges therebetween)carbon atoms in the chain. The chain may be linear or branched. Example SCFAs include, but are not limited to, acetate, propionate, iso-propionate, butyrate, iso-butyrate, and other SCFAs described herein, as well as derivatives thereof. The free SCFA terminus not connect to the N-(4-hydroxybenzoyloxy)alkyl methacrylate block may be one of a number of chemical groups including but not limited to methyl, hydroxyl, methoxy, thiol, amine, N-alkyl amine, and others.

In some embodiments, an HPMA-(N-(4-hydroxybenzoyloxy)alkyl methacrylamide) copolymer is composed of the hydrophilic polyHPMA block covalently attached to the N-(4-hydroxybenzoyloxy)alkyl methacrylamide block. The free HPMA terminus not connected to the N-(4-hydroxybenzoyloxy)alkyl methacrylamide block may be one of a number of chemical groups, including but not limited to hydroxyl, methoxy, thiol, amine, maleimide, halogen, polymer chain transfer agents, protecting groups, drug, biomolecule, or tissue targeting moiety. The N-(4-hydroxybenzoyloxy)alkyl methacrylamide block displays a pharmaceutically-relevant small molecule covalently attached to the hydroxyethyl functional group. A preferred embodiment of the pharmaceutically-relevant small molecule is short- and medium-chain fatty acids ("SCFA"s) and their derivatives containing, for example, between 3 and 12 (e.g., 3, 4, 5, 6, 7, 8, 9 10, 11, 12, or ranges therebetween) carbon atoms in the chain. The chain may be linear or branched. Example SCFAs include, but are not limited to, acetate, propionate, iso-propionate, butyrate, iso-butyrate, and other SCFAs described herein, as well as derivatives thereof. The free SCFA terminus not connect to the N-(4-hydroxybenzoyloxy)alkyl methacrylamide block may be one of a number of chemical groups including but not limited to methyl, hydroxyl, methoxy, thiol, amine, N-alkyl amine, and others.

Blocks may vary in molecular weight and therefore size, the adjustment of which alters the ratio of inert, unfunctionalized, pharmaceutically inactive material and active, functionalized pharmaceutically-active material. Some embodiments are a linear HPMA-(N-oxyethyl methacrylamide) block copolymer whose relative block sizes are between 0.25 and 3.5 (e.g., 0.25, 0.3, 0.35, 0.4, 0.45, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, and ranges therebetween (e.g., 0.7-1.8)). Other embodiments are a linear HPMA-(2-(4-hydroxybenzoyloxy)ethyl methacrylate) block copolymer whose relative block sizes are between 0.25 and 3.5 (e.g., 0.25, 0.3, 0.35, 0.4, 0.45, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, and ranges therebetween (e.g., 0.7-1.8)). A "relative block size" of 0.25-3.5 means that for every 1 mole of HPMA weight, the N-oxyethyl methacrylamide block (or a SCFA functionalized derivative) is 0.25 mole-3.5 mole). In some embodiments, block copolymers described herein form nanoparticles or micelles of diameter 10-1000 nm (e.g., 10, 20, 50, 100, 200, 500, 1000 nm, or ranges therebetween (e.g., 50-500 nm) when dispersed (e.g. in a liquid). The nanoparticles or micelles thus formed can then be isolated as a solid (e.g. in a powder, by lyophilization, etc.) with or without stabilizers (e.g. surfactants).

Although specific embodiments herein refer to polyHPMA as the hydrophilic block, other hydrophilic polymers may be used in place of polyHPMA including poly(ethylene oxide)-co-poly(propylene oxide) random, di- or multiblock copolymers, poly(vinyl alcohol), poly ethylene-co-vinyl alcohol), poly(N-vinyl pyrrolidone), poly(acrylic acid), poly(methyloxazoline) ("PMOXA"), poly(ethyloxazoline), poly(alkylacrylates), poly(acrylamide), poly(N-alkylacrylamides), hydrophilic polypeptide, polysaccharide, poly(N,N-dialkylacrylamides), hyaluronic acid, alginate, cyclodextrin, or poly(N-acryloylmorpholine). The hydrophilic block may be present at a molecular weight of between 3000 and 50,000 Da (e.g., 3000, 4000, 5000 Da, 6000 Da, 7000 Da, 8000 Da, 9000 Da, 10000 Da, 11000 Da, 12000 Da, 13000 Da, 14000 Da, 15000 Da, 20000 Da, 25000 Da, 30000 Da, 35000 Da, 40000 Da, 45000 Da, 50000 Da, or ranges therebetween (e.g., 9000-14000 Da, 14000-30000)).

In certain embodiments, the copolymer compositions herein are administered in the form of a pharmaceutical composition, a dietary supplement, or a food or beverage. When the compositions herein are used as a food or beverage, the food or beverage can be, e.g. a health food, a functional food, a food for a specified health use, a dietary supplement, or a food for patients. The composition may be administered once or more than once. If administered more than once, it can be administered on a regular basis (e.g. two times per day, once a day, once every two days, once a week, once a month, once a year) or on as needed, or irregular basis. The frequency of administration of the composition can be determined empirically by those skilled in the art.

Release of the pharmaceutically-active small molecule (e.g., SCFA) is a necessarily important aspect of the copolymer performance for material processing or downstream biological applications. In some embodiments, the pharmaceutically-active small molecule may be cleaved from the polymer backbone under suitable biological conditions, including hydrolysis (e.g. at certain pH) and enzyme activity (e.g. an esterase). In this regard, the copolymer may be termed a prodrug. In various embodiments, the pharmaceutical composition includes about 10-80% (e.g., 10%, 11%, 12%, 13%, 14%, 15%, 20%, 25%, 30%, 35%, 40%, 45%, 50%, 60%, 70%, 80%, or ranges therebetween) of pharmaceutically-active small molecule, e.g. a SCFA or derivative thereof, by weight. Those skilled in the art of clinical pharmacology can readily arrive at dosing amounts using routine experimentation.

Release of the pharmaceutically-active small molecule necessarily has a therapeutic effect recapitulating the therapeutic effects of SCFAs, including targeting the barrier function of the intestine and the mucus layer of the gut and all diseases in which SCFAs have been implicated to have a therapeutic benefit, including increasing mucus layer thickness or barrier function are implicated may be treated. In some embodiments, the human diseases that are treatable include, but are not limited to, rheumatoid arthritis, celiac disease and other autoimmune diseases, food allergies of all types, eosinophilic esophagitis, allergic rhinitis, allergic asthma, pet allergies, drug allergies, and other allergic and atopic diseases, inflammatory bowel disease, ulcerative colitis, Crohn's diseases, and additional inflammatory conditions, infectious diseases, metabolic disorders, multiple sclerosis, Alzheimer's disease, Parkinson's disease, dementia, and other diseases of the central nervous system, thalassemia and other blood disorders, colorectal cancer, diarrhea and related diseases effecting gut motility, Type I diabetes, and autism spectrum disorders, among others. This list is not exhaustive, and those skilled in the art can readily treat additional indications that have been shown to have therapeutic effect of SCFAs.

Pharmaceutical preparations can be formulated from the composition of the invention by drug formulation methods known to those skilled in the art. Formulations are prepared using a pharmaceutically acceptable "carrier" composed of materials that are considered safe and effective, without causing undesirable biological side effects or unwanted interactions. Suitable carriers include, but are not limited to, saline, buffered saline, dextrose, water, glycerol, ethanol, and combinations thereof. The composition can be adapted for the mode of administration and can be in the form of, e.g., a pill, tablet, capsule, spray, powder, or liquid. In some embodiments, the pharmaceutical composition contains one or more pharmaceutically acceptable additives suitable for the selected route and mode of administration, such as coatings, fillers, binders, lubricant, disintegrants, stabilizers, or surfactants. These compositions may be administered by, without limitation, any parenteral route, including intravenous, intra-arterial, intramuscular, subcutaneous, intradermal, intraperitoneal, intrathecal, as well as topically, orally, and by mucosal routes of delivery such as intranasal, inhalation, rectal, vaginal, buccal, and sublingual. In some embodiments, the pharmaceutical compositions of the invention are prepared for administration to vertebrate (e.g. mammalian) subjects in the form of liquids, including sterile, non-pyrogenic liquids for injection, emulsions, powders, aerosols, tablets, capsules, enteric coated tablets, or suppositories.

EXAMPLES

Example 1: Preparation of N-(2-hydroxyethyl) methacrylamide monomers with pharmaceutically-active small molecules Ethanolamine (3.70 mL, 61.4 mmol, 2.0 eq), triethylamine (4.72 mL, 33.8 mmol, 1.1 eq) and 50 mL DCM were added into a 250 mL flask. After the system was cooled down by an ice bath, (1) methacryloyl chloride (3.00 mL, 30.7 mmol, 1.0 eq) was added dropwise under the protection of nitrogen. The reaction was allowed to warm up to room temperature and reacted overnight. Then the reaction mixture was concentrated by rotary evaporation and purified on a silica column using DCM/MeOH. The product N-(2-hydroxyethyl) methacrylamide (2) was obtained as colorless oil (3.42 g, 86.3%) and analyzed by 1H-NMR (500 MHz, CDCl$_3$) $\delta_H$ ppm 1.93 (s, 3H, C(CH$_2$)—CH$_3$), 3.43 (m, 2H, NH—CH$_2$), 3.71 (m, 2H, O—CH$_2$), 5.32 (s, 1H, CCH$_2$), 5.70 (s, 1H, CCH$_2$), 6.44 (br s, 1H, NH).

N-(2-hydroxyethyl) methacrylamide (3.30 mL, 25.6 mmol, 1.0 eq), triethylamine (7.15 mL, 51.2 mmol, 2.0 eq) and 50 mL DCM were added into a 250 mL flask. After the reaction system was cooled down by an ice bath, butyric anhydride (5.00 mL, 30.7 mmol, 1.2 eq) was added dropwise under the protection of nitrogen. The system was allowed to react overnight. The reaction mixture was filtered and washed by NH$_4$Cl solution, NaHCO$_3$ solution, and water. After dried by anhydrous MgSO$_4$, the organic layer was concentrated by rotary evaporation and purified on a silica column using DCM/MeOH. The product N-butanoyloxyethyl methacrylamide (3) was obtained as pale yellow oil (4.56 g, 89.6%) and analyzed by 1H-NMR (500 MHz, CDCl$_3$) $\delta_H$ ppm 0.95 (t, 3H, CH$_2$CH$_2$—CH$_3$), 1.66 (m, 2H, CH$_2$—CH$_2$), 1.97 (s, 3H, C(CH$_2$)—CH$_3$), 2.32 (t, 2H, CO—CH$_2$), 3.59 (dt, 2H, NH—CH$_2$), 4.23 (t, 2H, O—CH$_2$), 5.35 (s, 1H, CCH$_2$), 5.71 (s, 1H, CCH$_2$), 6.19 (br s, 1H, NH). This example demonstrates the feasibility of attaching pharmaceutically-active small molecules to a monomeric unit of the block copolymer. Additional SCFAs can be attached to the monomeric unit in a similar manner.

Example 2A: Preparation of Block Copolymers of Hydrophilic Polymers with N-(2-Hydroxyethyl Methyacrylamide pHPMA was prepared using 2-cyano-2-propyl benzodithioate as the RAFT chain transfer agent and 2,2'-Azobis(2-methylpropionitrile) (AIBN) as the initiator. Briefly, HPMA (4) (1.0 g, 7.0 mmol, 1.0 eq), 2-cyano-2-propyl benzodithioate (15 mg, 0.07 mmol, 1/100 eq), and AIBN (2.9 mg, 0.017 mmol, 1/400 eq) were dissolved in 2.0 mL MeOH in a Schlenk tube. The reaction mixture was subjected to four freeze-pump-thaw cycles. The polymerization was conducted at 70° C. for 15 h. The polymer was precipitated in petroleum ether for five times and dried in the vacuum chamber overnight. The product poly(HPMA) (5) was obtained as light pink solid (0.79 g, 79%) and analyzed by 1H-NMR (500 MHz, DMSO-d6), $\delta_H$ ppm 0.8-1.2 (m, 6H, CH(OH)—CH$_3$ and backbone CH$_3$), 1.5-1.8 (m, 2H, backbone CH$_2$), 2.91 (m, 2H, NH—CH$_2$), 3.68 (m, 1H, C(OH)—H), 4.70 (m, 1H, CH—OH), 7.18 (m, 1H, NH).

The block copolymer was prepared using pHPMA as the macro-RAFT chain transfer agent and N-butanoyloxyethyl methacrylamide (3) as the monomer of the second RAFT polymerization. Briefly, pHPMA (0.71 g, 1.0 eq), N-butanoyloxyethyl methacrylamide (2.0 g, 10.0 mmol, 100 eq), and AIBN (4.1 mg, 0.025 mmol, 0.25 eq) were dissolved in 4.0 mL MeOH in a Schlenk tube. The reaction mixture was subjected to four freeze-pump-thaw cycles. The polymerization was conducted at 70° C. for 15 h. The polymer was precipitated in petroleum ether for five times and dried in the vacuum chamber overnight. The product was obtained as light pink solid (1.54 g, 75%) and analyzed by 1H-NMR (500 MHz, DMSO-d6) $\delta_H$ ppm 0.80-1.1 (m, 9H, CH(OH)—CH$_3$ (HPMA), CH$_2$—CH$_3$ (BMA), and backbone CH$_3$), 1.55 (m, 4H, CH$_2$—CH$_2$ (BMA) and backbone CH$_2$), 2.28 (m, 2H, CO—CH$_2$ (BMA)), 2.91 (m, 2H, NH—CH$_2$ (HPMA)), 3.16 (m, 2H, NH—CH$_2$ (BMA)), 3.67 (m, 1H, CH(OH)—H), 3.98 (m, 2H, O—CH$_2$ (BMA)), 4.71 (m, 1H, CH—OH (HPMA)), 7.19 (m, 1H, NH), 7.44 (m, 1H, NH). Extending from this example, molecular weights varying from 5 kD and 14 kD for each block respectively can be readily obtained, leading to a variety of ratios of inert and active blocks in the polymer. In this way, the range of pharmaceutically-active ingredient thereby incorporated can be about 10-80% of the total polymer weight.

Example 2B: Preparation of 2-(4-Hydroxybenzoyloxy)Ethyl Methacrylate Monomers with Pharmaceutically-Active Small Molecules 2-Bromoethanol (4.36 mL, 61.5 mmol, 1.5 eq), triethylamine (9.15 mL, 65.6 mmol, 1.6 eq) and 60 mL DCM were added into a 250 mL flask. After the system was cooled down by an ice bath, (1) methacryloyl chloride (4.00 mL, 41.0 mmol, 1.0 eq) was added dropwise under the protection of nitrogen. The reaction was allowed to warm up to room temperature and reacted overnight. Then the reaction mixture was concentrated by rotary evaporation and purified on a silica column using DCM/MeOH. The product 2-bromoethyl methacrylate (7) was obtained as colorless oil (6.62 g, 84.1%) and analyzed by 1H-NMR (500 MHz, CDCl$_3$) $\delta_H$ ppm 1.95 (s, 3H, C(CH$_2$)—CH$_3$), 3.57 (m, 2H, Br—CH$_2$), 4.45 (m, 2H, O—CH$_2$), 5.62 (s, 1H, CCH$_2$), 6.18 (s, 1H, CCH$_2$).

4-Hydroxybenzoic acid (2.00 g, 14.5 mmol, 1.2 eq), sodium bicarbonate (2.94 g, 35.0 mmol, 2.9 eq) and 20 mL DMF were added into a two-armed flask. The mixture was remained at 70° C. for 1 h. Then, 2-bromoethyl methacrylate (2.32 g, 12.1 mmol, 1.0 eq) was dissolved in 10 mL DMF and added into the flask dropwise. The reaction was conducted at 70° C. overnight. The reaction mixture was cooled, poured into 100 mL water and extracted three times with 100 mL of a 50:50 hexane/ethyl acetate mixture. The organic phases were washed twice with water (100 mL), dried over Na$_2$SO$_4$ and purified on a silica column using DCM/MeOH. The product 2-(4-hydroxybenzoyloxy)ethyl methacrylate (8) was obtained as viscous oil (0.87 g, 58%) and analyzed by 1H-NMR (500 MHz, CDCl$_3$) $\delta_H$ ppm 1.95 (s, 3H, C(CH$_2$)—CH$_3$), 4.48 (m, 2H, O—CH$_2$), 4.54 (m, 2H, O—CH$_2$), 5.62 (s, 1H, CCH$_2$), 6.14 (s, 1H, CCH$_2$), 6.86 (d, 2H, ArH), 7.96 (d, 2H, ArH).

2-(4-hydroxybenzoyloxy)ethyl methacrylate (0.87 g, 3.48 mmol, 1.0 eq), triethylamine (1.46 mL, 10.44 mmol, 3.0 eq) and 30 mL DCM were added into a 100 mL flask. After the reaction system was cooled down by an ice bath, butyric anhydride (1.14 mL, 6.96 mmol, 2.0 eq) was added dropwise under the protection of nitrogen. The system was allowed to react overnight. The reaction mixture was filtered and washed by NH$_4$Cl solution, NaHCO$_3$ solution, and water. After dried by anhydrous MgSO$_4$, the organic layer was concentrated by rotary evaporation and purified on a silica column using DCM/MeOH. The product 2-(4-butanoyloxybenzoyloxy)ethyl methacrylate (9) was obtained as pale oil (1.02 g, 92%) and analyzed by 1H-NMR (500 MHz, CDCl$_3$) $\delta_H$ ppm 1.06 (t, 3H, CH$_2$CH$_2$—CH$_3$), 1.72 (m, 2H, CH$_2$—CH$_2$), 1.94 (s, 3H, C(CH$_2$)—CH$_3$), 2.54 (t, 2H, CO—CH$_2$), 4.48 (m, 2H, O—CH$_2$), 4.56 (m, 2H, O—CH$_2$), 5.59 (s, 1H, CCH$_2$), 6.14 (s, 1H, CCH$_2$), 7.16 (d, 2H, ArH), 8.06 (d, 2H, ArH).

Example 3: Preparation of Block Copolymers of Hydrophilic Polymers with N-(2-Hydroxyethyl Methyacrylamide pHPMA was prepared using 2-cyano-2-propyl benzodithioate as the RAFT chain transfer agent and 2,2'-Azobis(2-methylpropionitrile) (AIBN) as the initiator. Briefly, HPMA (4) (1.0 g, 7.0 mmol, 1.0 eq), 2-cyano-2-propyl benzodithioate (15 mg, 0.07 mmol, 1/100 eq), and AIBN (2.9 mg, 0.017 mmol, 1/400 eq) were dissolved in 2.0 mL MeOH in a Schlenk tube. The reaction mixture was subjected to four freeze-pump-thaw cycles. The polymerization was conducted at 70° C. for 15 h. The polymer was precipitated in petroleum ether for five times and dried in the vacuum chamber overnight. The product poly(HPMA) (5) was obtained as light pink solid (0.79 g, 79%) and analyzed by 1H-NMR (500 MHz, DMSO-d6), $\delta_H$ ppm 0.8-1.2 (m, 6H, CH(OH)—CH$_3$ and backbone CH$_3$), 1.5-1.8 (m, 2H, backbone CH$_2$), 2.91 (m, 2H, NH—CH$_2$), 3.68 (m, 1H, C(OH)—H), 4.70 (m, 1H, CH—OH), 7.18 (m, 1H, NH)

The block copolymer (pHPMA-b-pBMA) was prepared using pHPMA as the macro-RAFT chain transfer agent and N-butanoyloxyethyl methacrylamide (3) as the monomer of the second RAFT polymerization. Briefly, pHPMA (0.71 g, 1.0 eq), N-butanoyloxyethyl methacrylamide (2.0 g, 10.0 mmol, 100 eq), and AIBN (4.1 mg, 0.025 mmol, 0.25 eq) were dissolved in 4.0 mL MeOH in a Schlenk tube. The reaction mixture was subjected to four freeze-pump-thaw cycles. The polymerization was conducted at 70° C. for 15 h. The polymer was precipitated in petroleum ether for five times and dried in the vacuum chamber overnight. The product was obtained as light pink solid (1.54 g, 75%) and analyzed by 1H-NMR (500 MHz, DMSO-d6) $\delta_H$ ppm 0.80-1.1 (m, 9H, CH(OH)—$CH_3$ (HPMA), $CH_2$—$CH_3$ (BMA), and backbone $CH_3$), 1.55 (m, 4H, $CH_2$—$CH_2$ (BMA) and backbone $CH_2$), 2.28 (m, 2H, CO—$CH_2$ (BMA)), 2.91 (m, 2H, NH—$CH_2$ (HPMA)), 3.16 (m, 2H, NH—$CH_2$ (BMA)), 3.67 (m, 1H, CH(OH)—H), 3.98 (m, 2H, O—$CH_2$ (BMA)), 4.71 (m, 1H, CH—OH (HPMA)), 7.19 (m, 1H, NH), 7.44 (m, 1H, NH). Extending from this example, molecular weights varying from 5 kD and 14 kD for each block respectively can be readily obtained, leading to a variety of ratios of inert and active blocks in the polymer. In this way, the range of pharmaceutically-active ingredient thereby incorporated can be about 10-80% of the total polymer weight.

Example 4: Preparation of Block Copolymers of Hydrophilic Polymers with 2-(4-Hydroxybenzoyloxy)Ethyl Methacrylate The block copolymer (pHPMA-b-pBBOMA) was prepared using pHPMA as the macro-RAFT chain transfer agent and 2-(4-butanoyloxybenzoyloxy)ethyl methacrylate (10) as the monomer of the second RAFT polymerization. Briefly, pHPMA (0.50 g, 1.0 eq), 2-(4-butanoyloxybenzoyloxy)ethyl methacrylate (1.12 g, 3.5 mmol, 50 eq), and AIBN (3.0 mg, 0.018 mmol, 0.005 eq) were dissolved in 4.0 mL MeOH in a Schlenk tube. The reaction mixture was subjected to four freeze-pump-thaw cycles. The polymerization was conducted at 70° C. for 15 h. The polymer was precipitated in petroleum ether for five times and dried in the vacuum chamber overnight. The product was obtained as light pink solid (1.34 g, 83%) and analyzed by 1H-NMR (500 MHz, DMSO-d6) $\delta_H$ ppm 0.80-1.1 (m, 9H, CH(OH)—$CH_3$ (HPMA), $CH_2$—$CH_3$ (BBOMA), and backbone $CH_3$), 1.57 (m, 4H, $CH_2$—$CH_2$ (BBOMA) and backbone $CH_2$), 2.46 (m, 2H, CO—$CH_2$ (BBOMA)), 2.90 (m, 2H, NH—$CH_2$ (HPMA)), 3.67 (m, 1H, CH(OH)—H), 4.00-4.40 (m, 4H, O—$CH_2$ (BBOMA)), 4.71 (m, 1H, CH—OH (HPMA)), 7.17 (m, 2H, ArH (BBOMA)), 7.92 (m, 2H, ArH (BBOMA)).

Example 5: Preparation of Polymer Solutions

The polymer solutions were prepared using cosolvent evaporation method. 80 mg pHPMA-b-pBMA was dissolved in 1.0 mL ethanol in a beaker. Then, 1.0 mL 1× phosphate buffered saline (PBS) was added into the beaker. The solution was stirred vigorously for 6 hours to let ethanol evaporate. The polymeric solution was obtained at 80 mg/mL in 1×PBS and was stored at 4° C. The size of the polymeric formulation was measured by dynamic light scattering. This example demonstrates the assembly into particles in solution. Particles can be prepared using other solutions and additives in solutions as embodied in this example. Particle sizes from 10-1000 nm are attainable as embodied in this example.

Example 6: Administration of the Polymer Solutions Via Oral Gavage and Increase in Fecal SCFA Mice were orally gavaged using the polymer solutions prepared. 125 μL of a 80 mg/mL solution was administered by oral gavage into the stomach of a mouse using a needle. Mouse fecal samples were obtained every 4 hours and the fecal samples processed for gas chromatography. Gas chromatography samples were prepared as adapted from Kaur, 2012 by adding 0.4 mL of phosphate buffered saline to 0.1 g of feces and homogenizing by vortex. 0.1 mL of an internal standard mixture comprising 0.5 mM 4-methylvaleric acid, 5% meta-phosphoric acid, and 1.56 mg/mL copper sulfate was added, the sample vortexed, and then centrifuged at 13000 rpm for 10 min. 10 μL of the supernatant was injected into the gas chromatograph for analysis and concentrations of fecal SCFA were determined using a calibration curve. This example demonstrates that oral administration of the block copolymer increases the fecal concentration of the SCFA attached to the block polymer

Example 7: Administration of the Polymer Solutions Via Oral Gavage and Decrease in Physiological Markers of Allergic Reaction and Anaphylaxis An allergy to peanuts was induced in mice by sensitization via intragastric gavage with 5 mg peanut protein+10 μg cholera toxin as adjuvant ("allergic positive control" or "allergic" in this example and FIGS. 13, 14, 15, and 16) or 10 μg cholera toxin adjuvant only ("non-allergic negative control" in this example and FIGS. 13, 14, 15, and 16) at weaning and once weekly for 5 weeks total following a procedure previously reported and known to those skilled in the art. Data is reported for male mice only to control for subject weight and dosing. 80 mg/mL stock solutions of polymer were prepared, then diluted to 13.3 mg/mL (for a 2 mg daily dose of polymer) and 53.3 mg/mL (for a 8 mg daily dose of polymer) using phosphate buffered saline. 150 μL of the polymer solution was administered daily by intragastric gavage into the stomach of "allergic" mice using a needle. For "allergic" mice dosed with 2 mg daily (N=6), the 13.3 mg/mL solution was used; For "allergic" mice dosed with 8 mg daily (N=5), the 53.3 mg/mL solution was used; for "allergic" mice receiving no dose of polymer (N=6), 150 μL of 1×PBS was used as control. For "non-allergic negative control" mice (N=4), 150 μL of 1×PBS was dosed daily as control. One week after the 5th sensitization (day 35 of the experiment), the mice were given 5 mg of peanut protein via intraperitoneal injection. Core body temperature was monitored rectally for 90 minutes after injection and mouse serum was collected 90 minutes and 24 hours after injection. Serum was processed for ELISA and peanut-specific Immunoglobulin E (IgE), peanut-specific Immunoglobulin G1 (IgG1), and mouse mast cell protease-1 (mMCP-1) was determined. This example demonstrates that oral administration of the block copolymer reduces the physiological markers and symptoms of an allergic reaction when dosed daily

Figure 17:
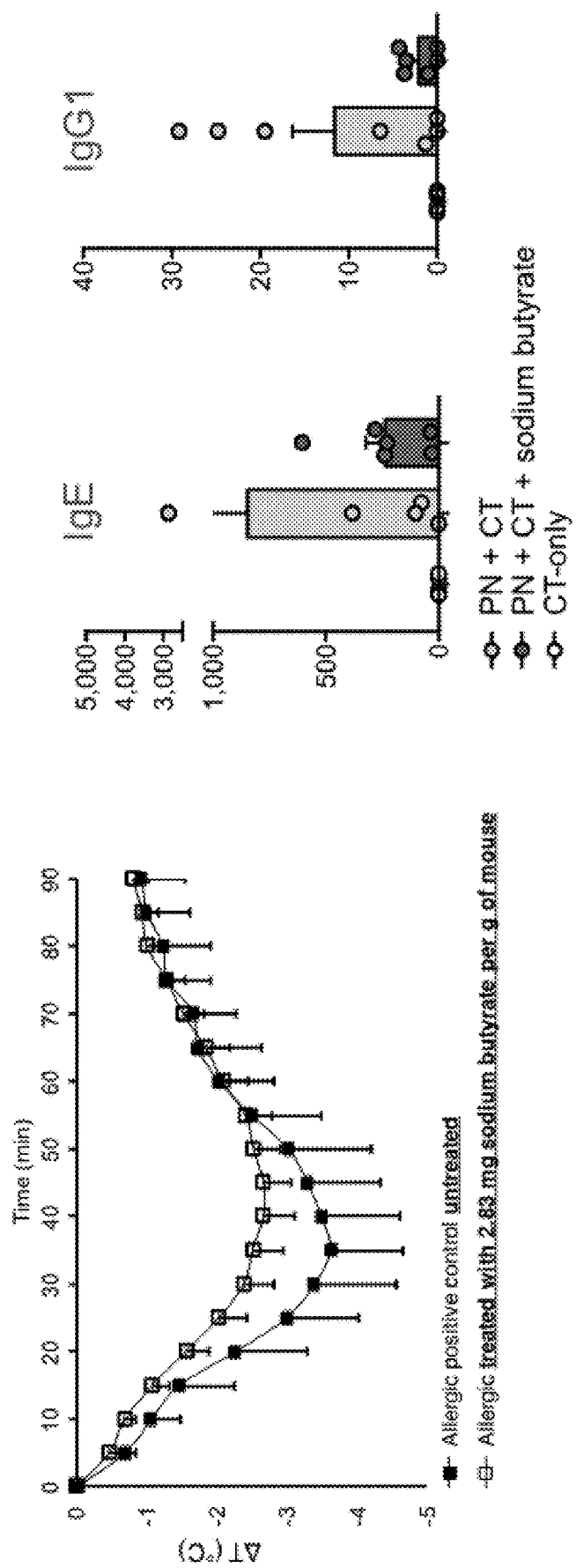
FIG. 17: Comparison of markers of allergic sensitivity in mice treated with sodium butyrate or not treated (labeled as "positive control" or "PN+CT" or "CT-only") after challenge with peanut protein. Left is the change in mouse core body temperature, middle is amount of peanut-specific IgE, and right is amount of peanut-specific IgG1.

Example 8: Administration of Sodium Butyrate Solutions Via Oral Gavage and Inferiority of Sodium Butyrate Compared to Polymer in Decreasing Physiological Markers of Allergic Reaction and Anaphylaxis An allergy to peanuts was induced in mice by sensitization via oral gavage with 6 mg peanut protein+10 μg cholera toxin ("allergic positive control" or "allergic"; N=19) at weaning and once weekly for 5 weeks total following a procedure previously reported and known to those skilled in the art. Mice received a dose of 2.83 mg sodium butyrate per g of mouse body weight daily by oral gavage of sodium butyrate dissolved in phosphate buffered saline into the stomach of a "allergic" mice using a needle. This dose is equivalent to the dose administered by polymer at 0.8 mg polymer per g of mouse body weight. Mice were weighed once weekly and the amount of solution adjusted based on the new weight. One week after the 5th sensitization (day 35 of the experiment), the mice were given 5 mg of peanut protein via intraperitoneal injection. Core body temperature was monitored rectally for 90 minutes after injection and mouse serum was collected 90 minutes and 24 hours after injection. Serum was processed for ELISA and peanut-specific Immunoglobulin E (IgE), peanut-specific Immunoglobulin G1 (IgG1), and mouse mast cell protease-1 (mMCP-1) was determined. These results demonstrate that oral administration of sodium butyrate at the same dose as an equivalent block copolymer is not effective at reducing the physiological markers and symptoms of an allergic reaction when dosed daily (FIG. 17).

Figure 18:
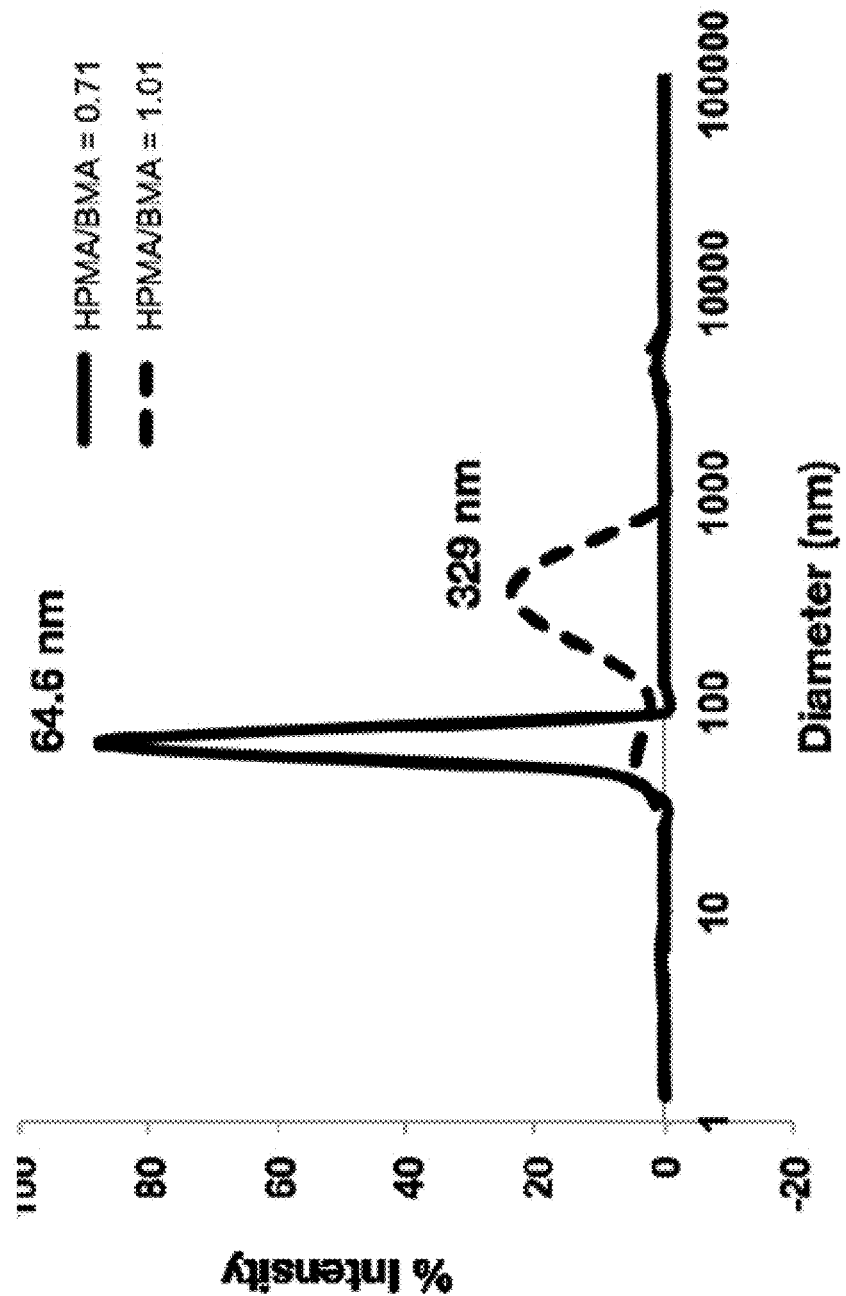
FIG. 18: DLS of polymer particles with the HPMA to BMA ratio listed in 1×PBS at 53.3 mg/mL

Example 9: Administration of Different Formulations of Polymer Via Oral Gavage do not Lead to Equivalent Effectiveness at Decreasing Physiological Markers of Allergic Reaction and Anaphylaxis Two formulations of polymer were prepared using the methods described in Examples 3 and 5. One polymer was characterized and demonstrated to have a ratio of HPMA:BMA block in the copolymer of 1.01 and a particle diameter of 329 nm by dynamic light scattering ("Formulation 2"). The other polymer was characterized and demonstrated to have a ratio of HPMA:BMA block in the copolymer of 0.75 and a particle diameter of 64.6 nm by dynamic light scattering ("Formulation 1") (FIG. 18).

Figure 19:
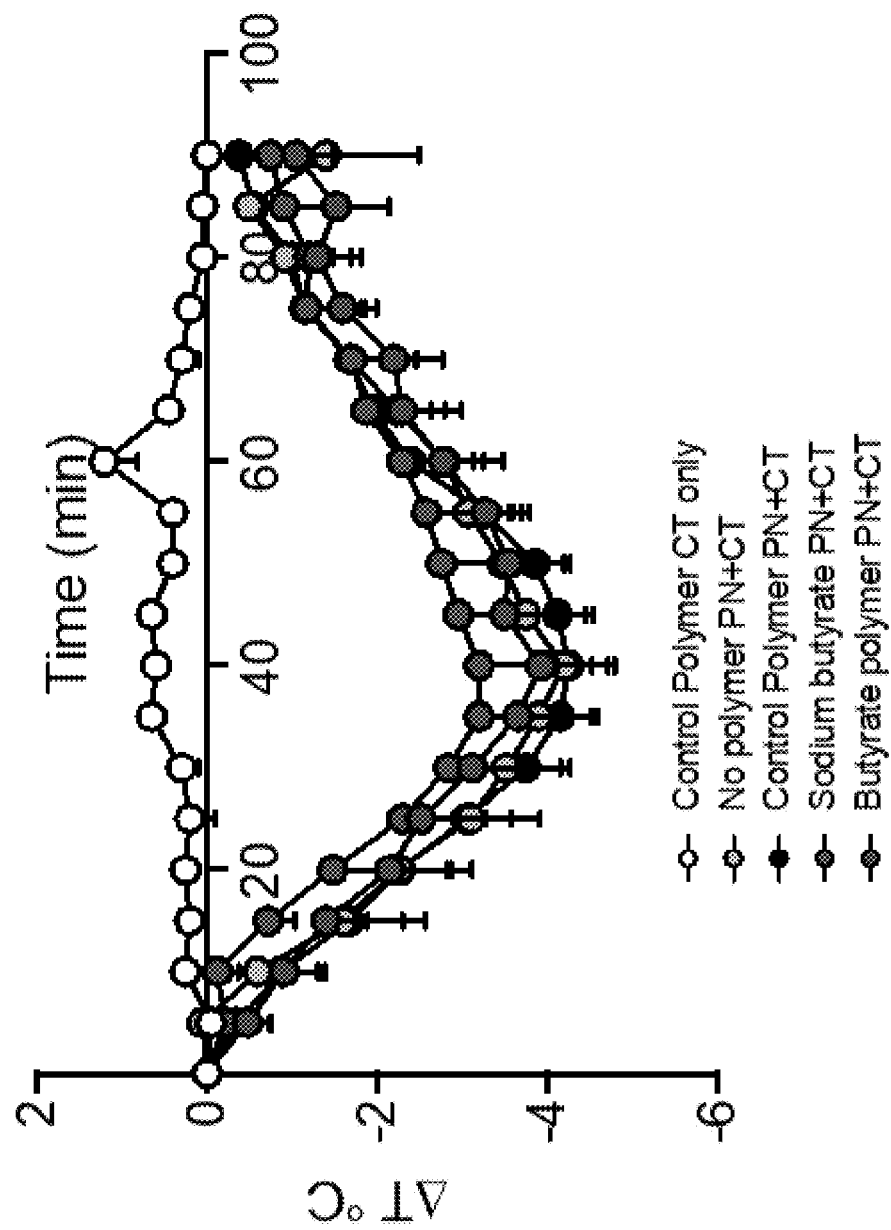
FIG. 19: Core body temperature over time after challenge with peanut protein with and without polymer and sodium butyrate treatment showing no protection with HPMA/BMA=1.01 ("butyrate polymer") or sodium butyrate without polymer.
Figure 21A:
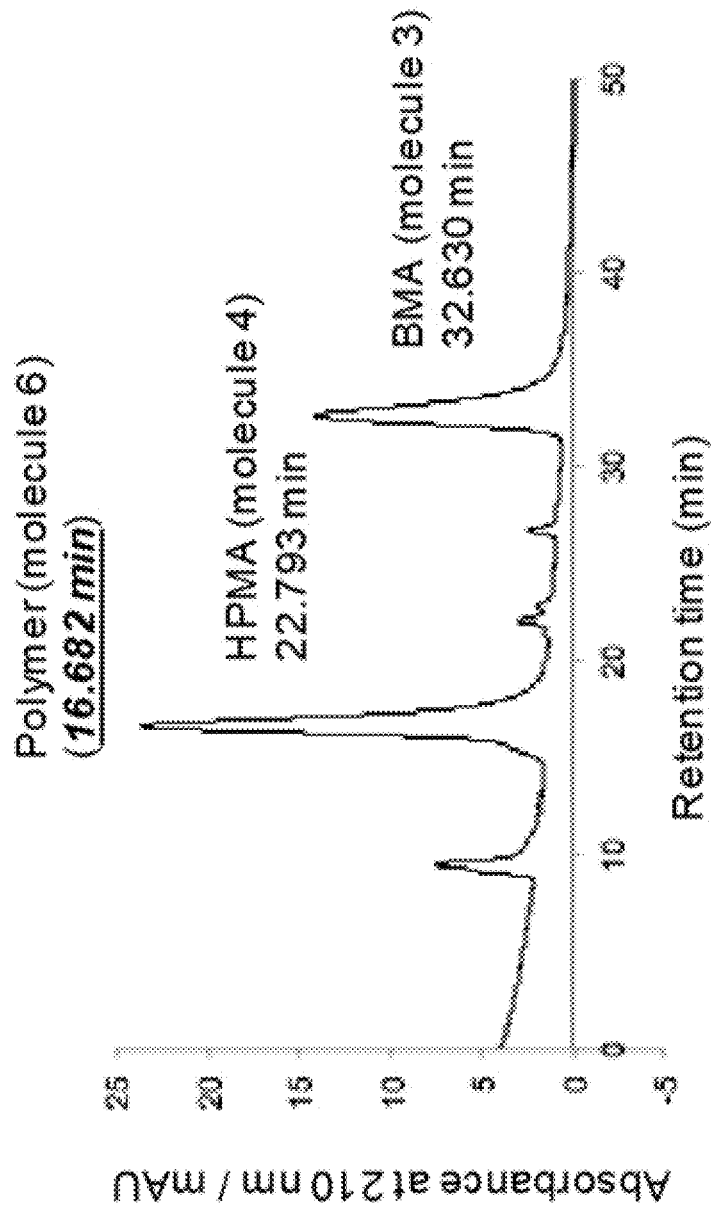
FIGS. 21A-C: A. GPC trace of pHPMA-b-pBMA Formulation 1; B. DLS trace of pHPMA-b-pBMA Formulation 1; C. NMR spectrum and integrations used to determine the molecular weight and HPMA:BMA block ratio for Formulation 1.
Figure 21B:
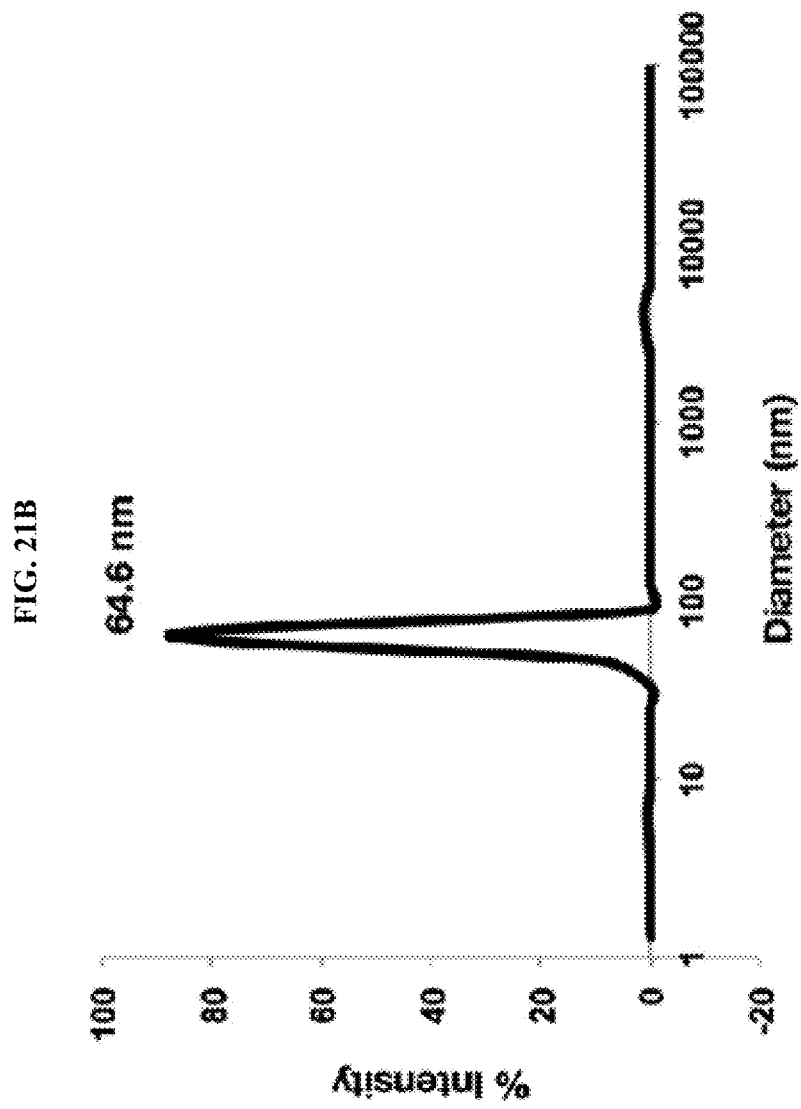
Figure 21C:
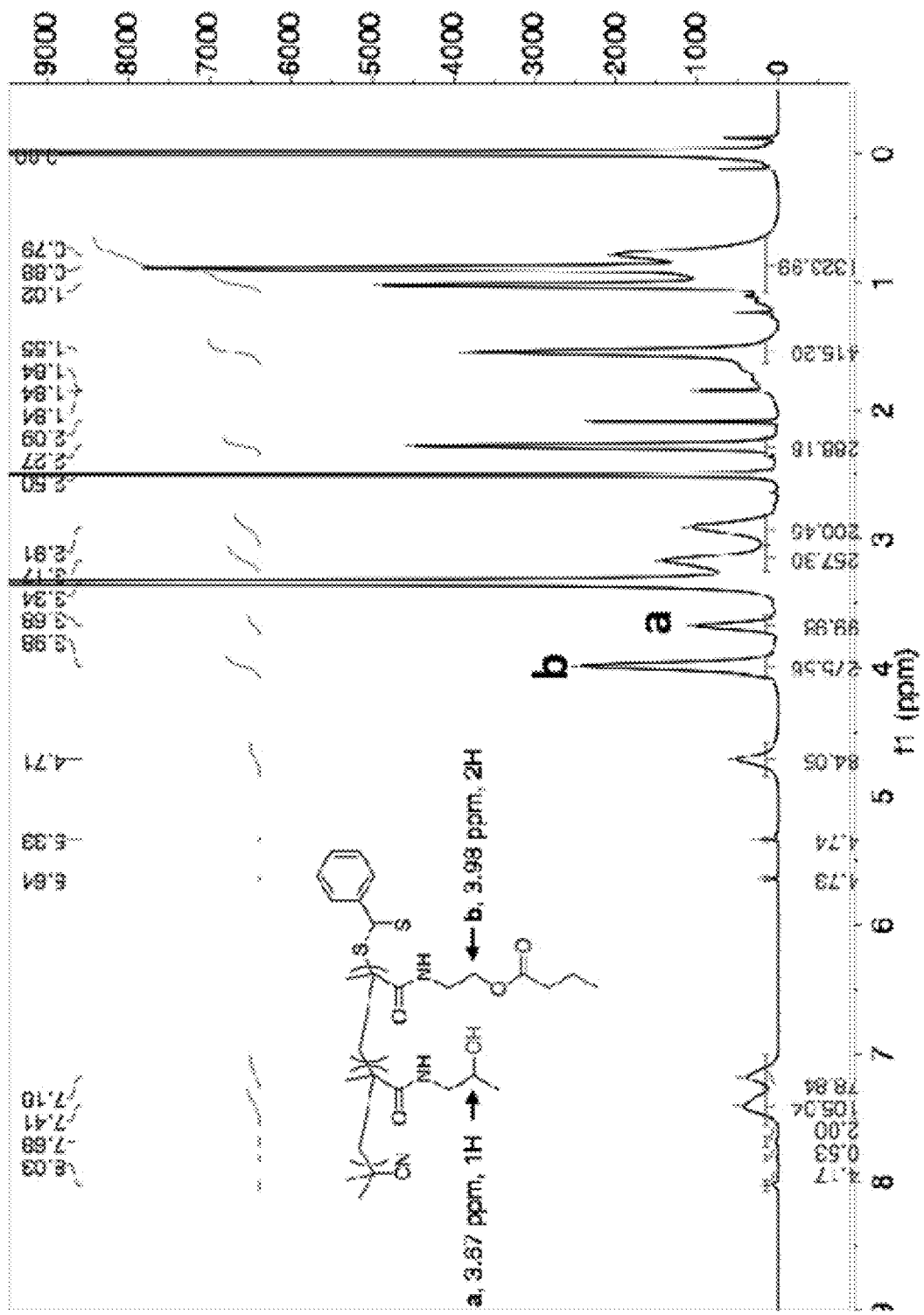
Figure 22A:
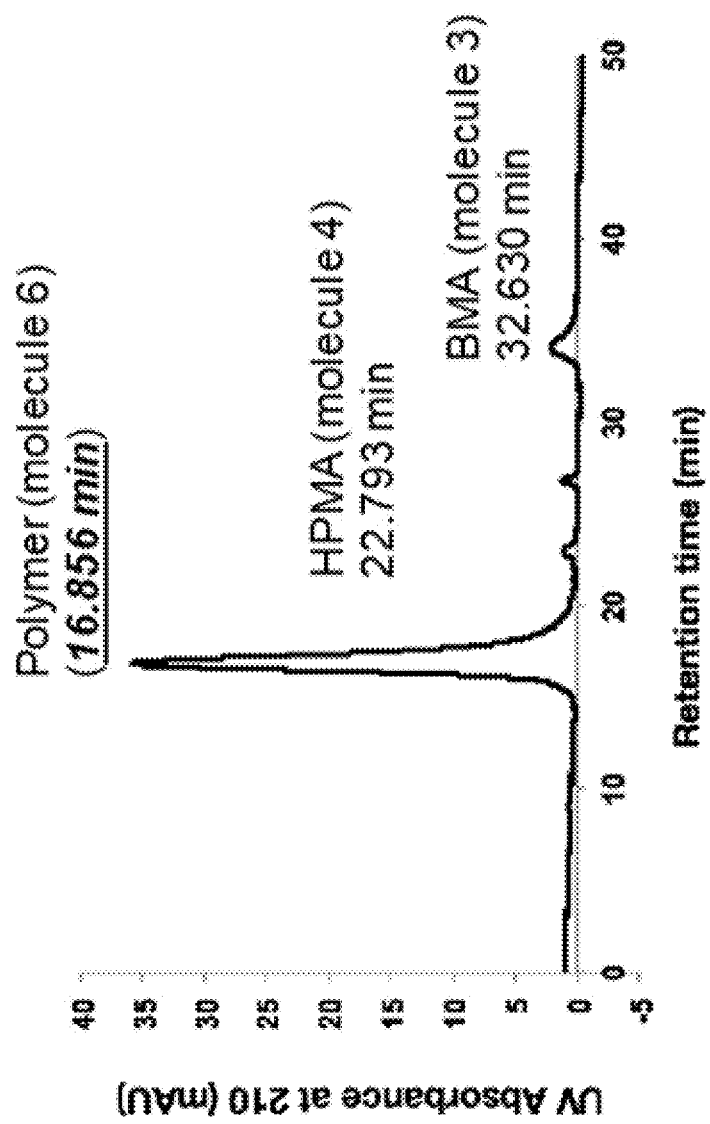
FIGS. 22A-C: A. GPC trace of pHPMA-b-pBMA Formulation 4; B. DLS trace of pHPMA-b-pBMA Formulation 4; C. NMR spectrum and integrations used to determine the molecular weight and HPMA:BMA block ratio for Formulation 4.
Figure 22B:
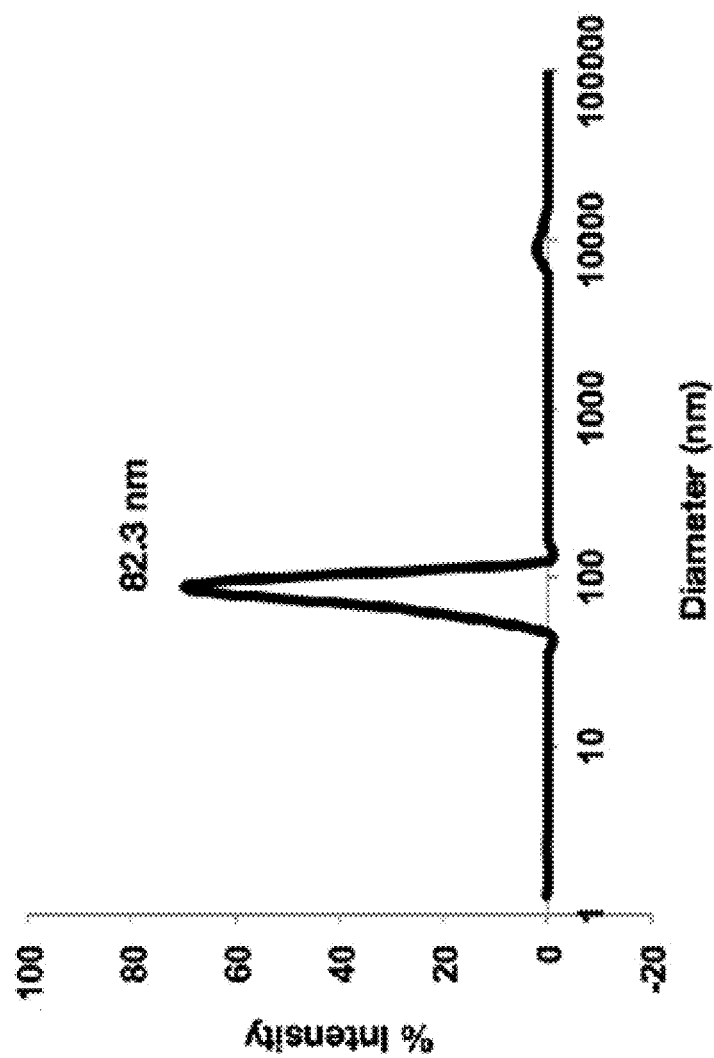
Figure 22C:
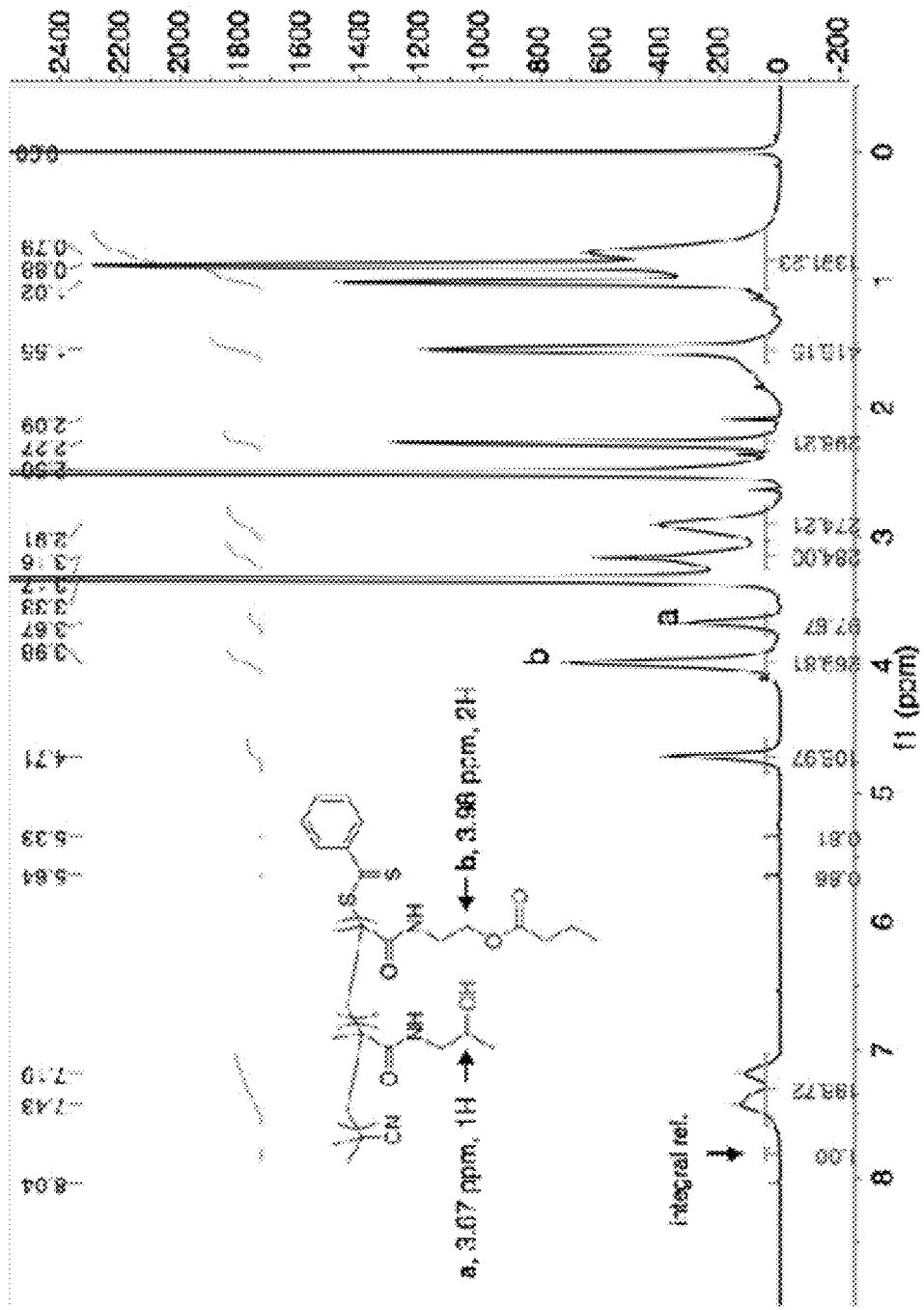
Figure 23A:
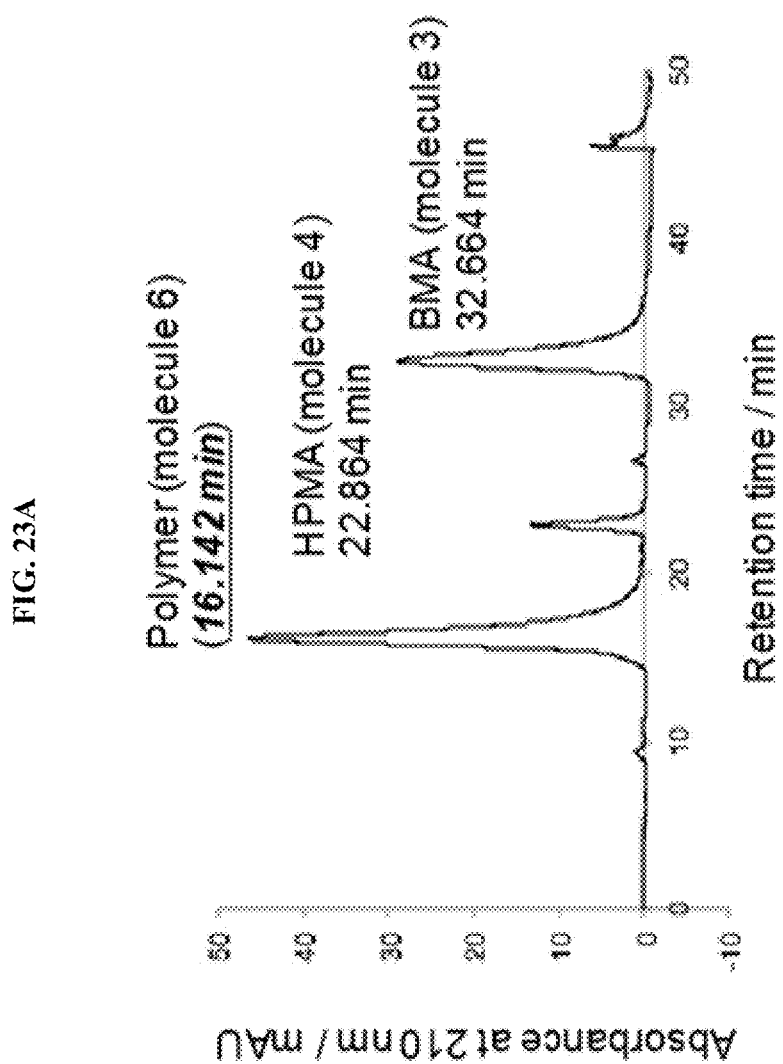
FIGS. 23A-C: A. GPC trace of pHPMA-b-pBMA Formulation 3; B. DLS trace of pHPMA-b-pBMA Formulation 3; C. NMR spectrum and integrations used to determine the molecular weight and HPMA:BMA block ratio for Formulation 3.
Figure 23B:
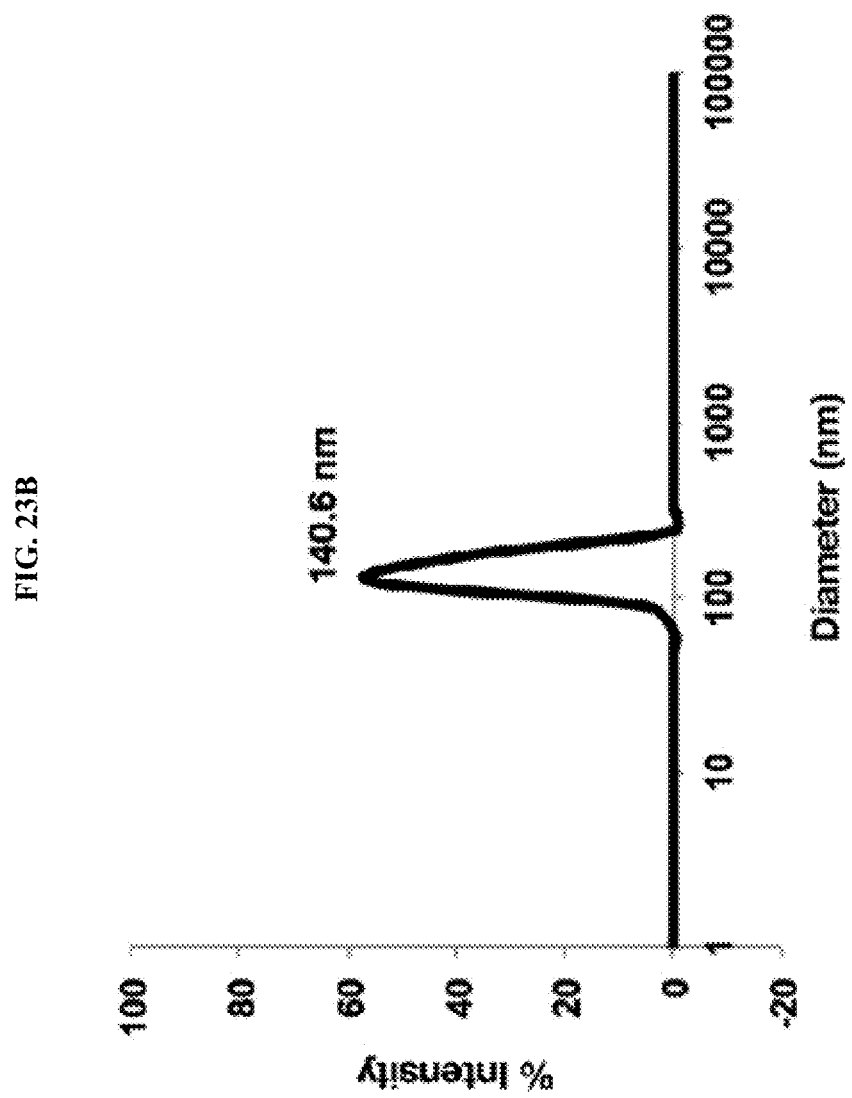
Figure 23C:
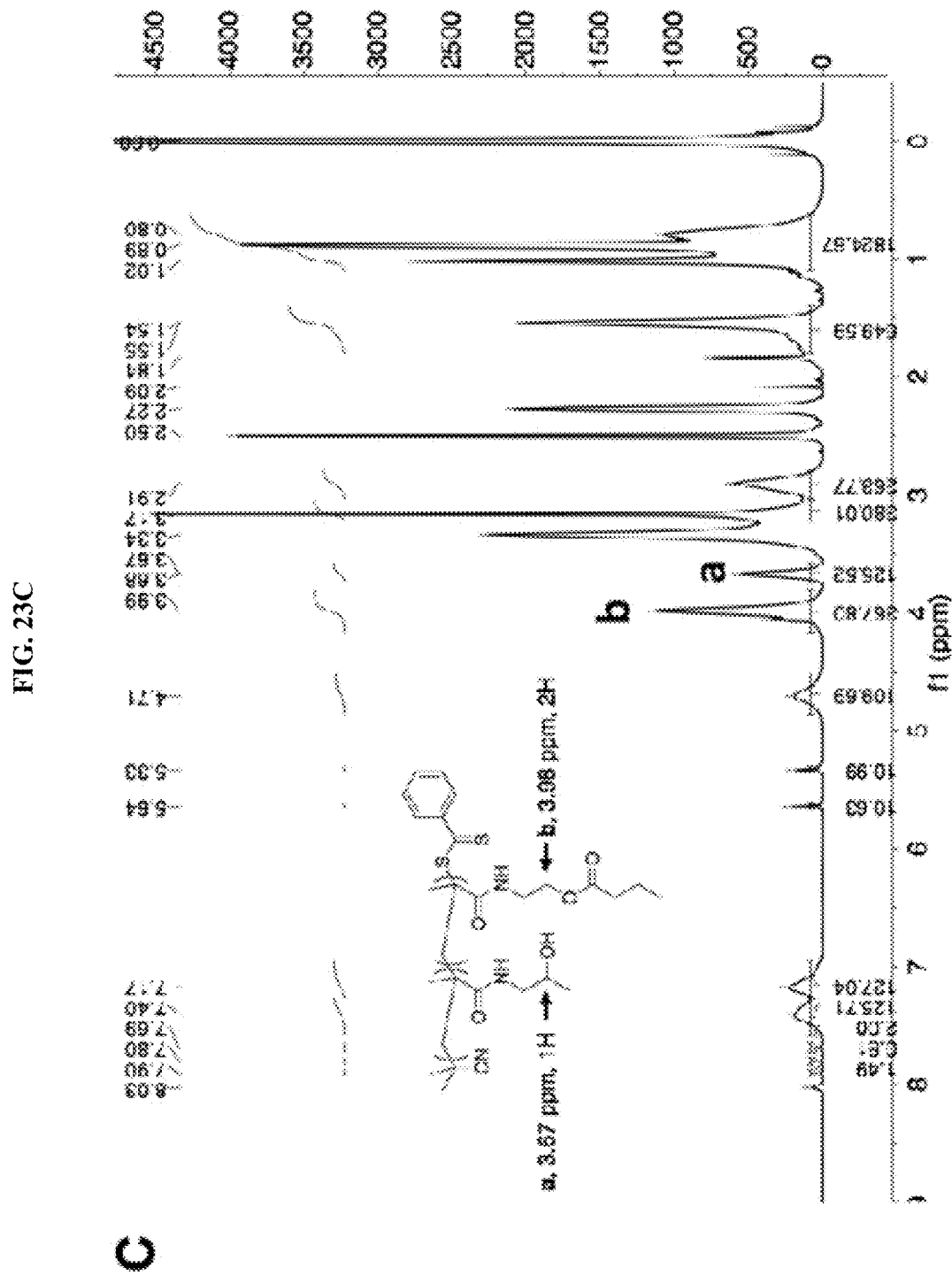
Figure 24:
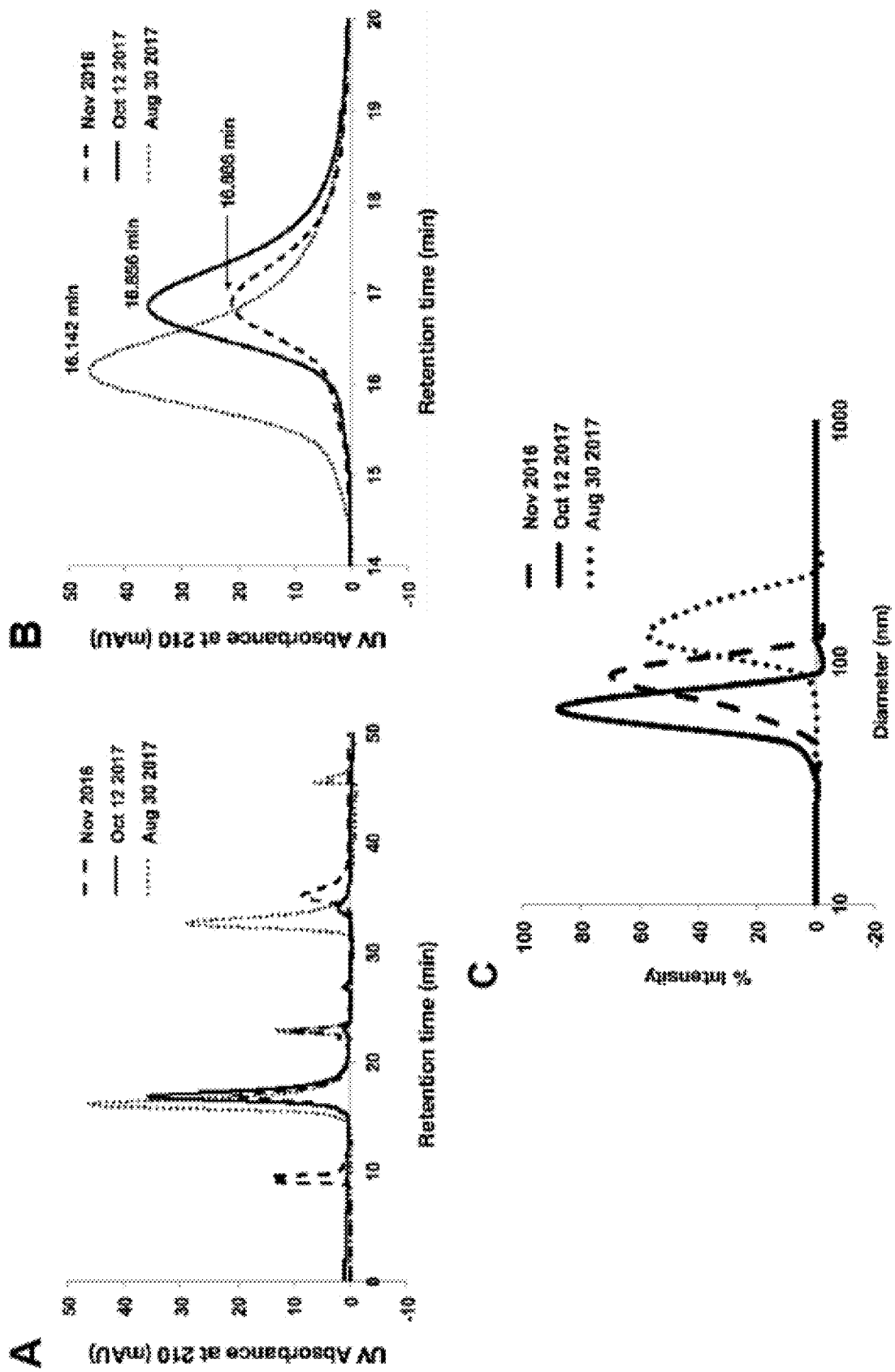
FIGS. 24A-C: A. Overlaid GPC traces of different batches of polymer pHPMA-b-pBMA; B. Overlaid detail of peak in (A.) at about 16 min corresponding to polymer pHPMA-b-pBMA demonstrating differences in molecular weight and elution time; C. Overlaid DLS traces of different batches of polymer pHPMA-b-pBMA demonstrating that different molecular weights lead to different particle sizes.
Figure 25:
FIG. 25: Photographs of different pHPMA-b-pBMA solutions showing differences in solution color and opacity depending on the particle size and molecular weight.

An allergy to peanuts was induced in mice by sensitization via oral gavage with 6 mg peanut protein+10 µg cholera toxin ("allergic positive control" or "allergic") or 10 µg cholera toxin alone ("non-allergic negative control"; N=4) at weaning and once weekly for 5 weeks total following a procedure previously reported and known to those skilled in the art. 80 mg/mL stock solutions of Formulation 2 polymer were prepared as in Example 3, then diluted to 53.3 mg/mL. 0.8 mg of polymer per g of mouse body weight was administered daily by oral gavage into the stomach of a "allergic" mice using a needle. Another group of "allergic" mice received 2.83 mg of sodium butyrate identically to Example 7. Another group of "allergic" mice received a 0.8 mg per g of mouse body weight daily dose of a control polymer that could not release butyric acid. For "allergic" mice receiving no dose of polymer, volume-matched solution of 1×PBS was used as control. For "non-allergic negative control" mice, 0.8 mg of control polymer per g of mouse body weight was dosed daily as control. One week after the 5th sensitization (day 35 of the experiment), the mice were given 5 mg of peanut protein via intraperitoneal injection. Core body temperature was monitored rectally for 90 minutes after injection and mouse serum was collected 90 minutes and 24 hours after injection (FIG. 19). Serum was processed for ELISA and peanut-specific Immunoglobulin E (IgE), peanut-specific Immunoglobulin G1 (IgG1), and mouse mast cell protease-1 (mMCP-1) was determined. These results demonstrate that increase in fecal butyrate is not sufficient to predict efficacy, and that molecular and morphological characteristics of the polymer non-obviously result in differences in therapeutic effect. Specifically, Formulation 2, which differs from Formulation 1 only by molecular weight and block ratio, does not reduce the physiological markers and symptoms of an allergic reaction when dosed daily.

Example 10: Administration of formulations of Polymer Via Oral Gavage Leads to Equivalent Changes to Fecal Butyrate Concentration, but does not Lead to Equivalent Effectiveness at Decreasing Physiological Markers of Allergic Reaction and Anaphylaxis. Equivalent Effectiveness Requires Strict Control of Certain Polymer Molecular Characteristics Three formulations of polymer were prepared using the methods described in Examples 3 and 5 (FIG. 20). One polymer was characterized and demonstrated to have a ratio of HPMA:BMA block in the copolymer of 0.75, a molecular weight of about 40,000 g/mol, and a particle diameter of 60-70 nm by dynamic light scattering ("Formulation 1"). A second polymer was characterized and demonstrated to have a ratio of HPMA:BMA block in the copolymer of 0.71, a molecular weight of about 52,000 g/mol, and a particle diameter of 120-130 nm by dynamic light scattering ("Formulation 3"). A third polymer was characterized and demonstrated to have a ratio of HPMA:BMA block in the copolymer of 0.77, a molecular weight of 39,000 g/mol, and a particle diameter of 75-82 nm by dynamic light scattering ("Formulation 4").

Analysis of the three formulations by GPC, DLS, and NMR are depicted in FIGS. 21-24.

Figure 26:
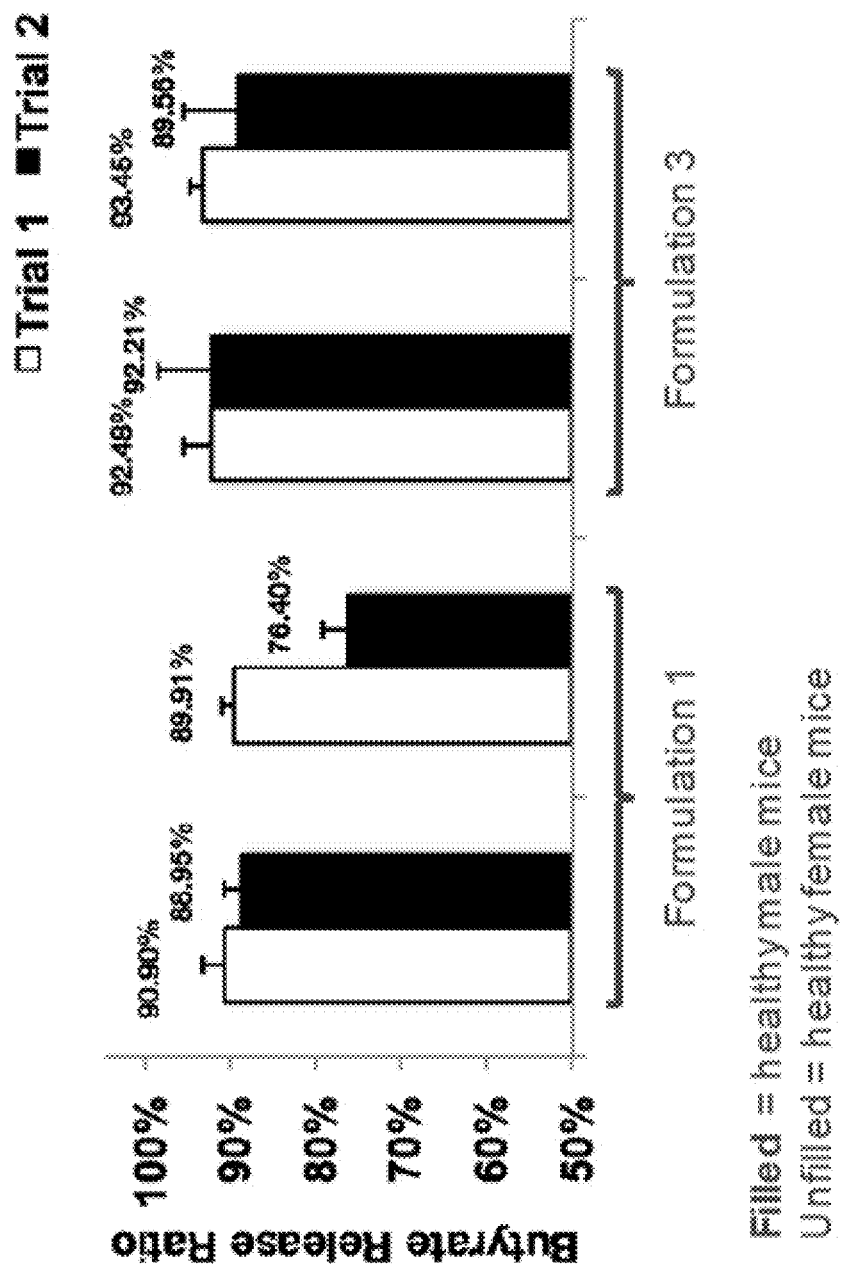
FIG. 26: Percent of butyrate released from polymer backbone, either Formulation 1 or Formulation 3, after a single dose to mice.
Figure 27A:
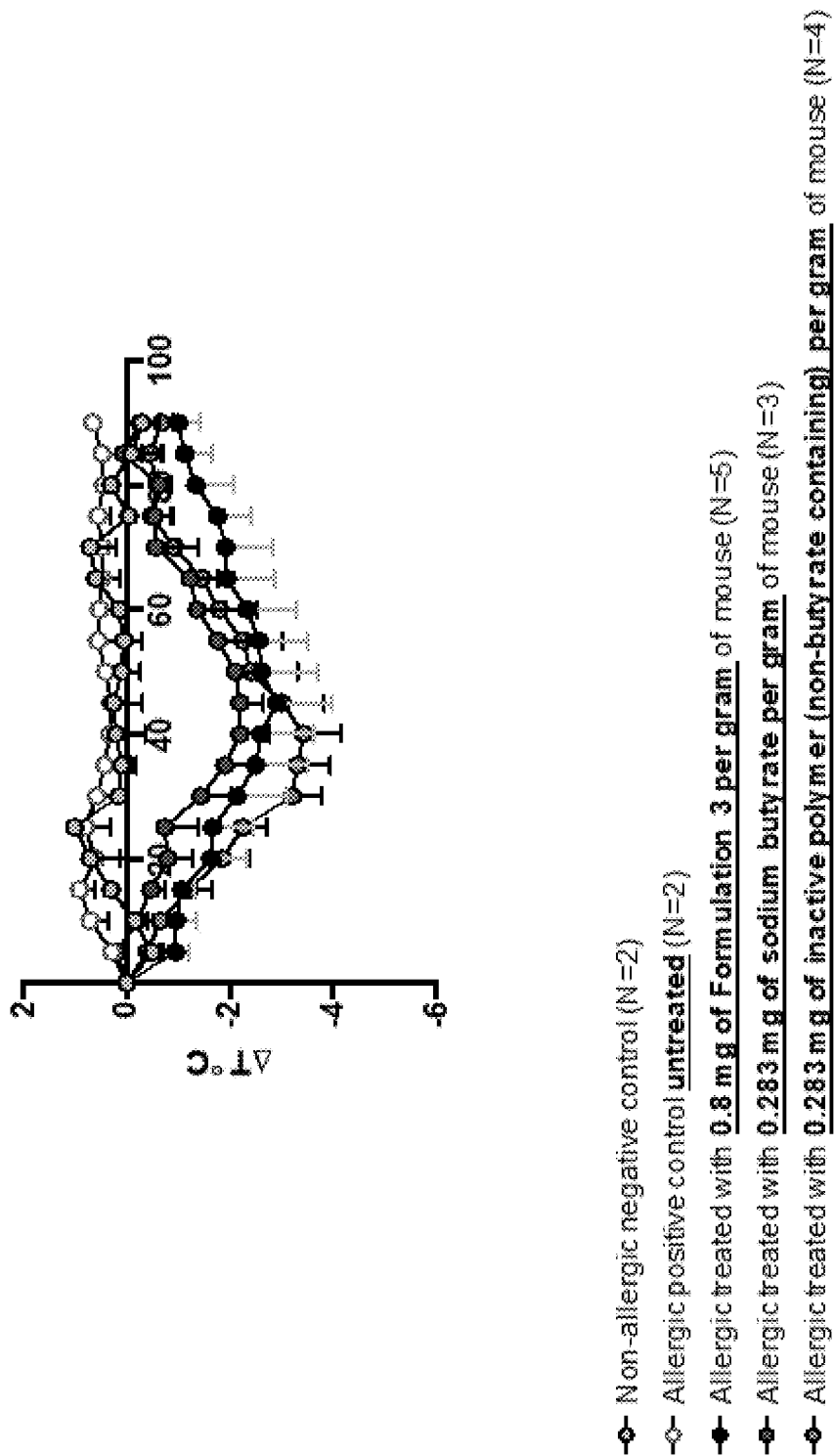
FIGS. 27A-D: Comparison of (A) core body temperature over time after challenge, (B) concentration of peanut-specific IgE in serum 24 hours before challenge, (C) concentration of peanut-specific IgG1 in serum 24 hours before challenge, and (D) concentration of mouse mast cell protease-1 in serum 90 minutes after challenge with peanut protein when mice are treated daily with Formulation 3 or sodium butyrate or are untreated.
Figure 27B:
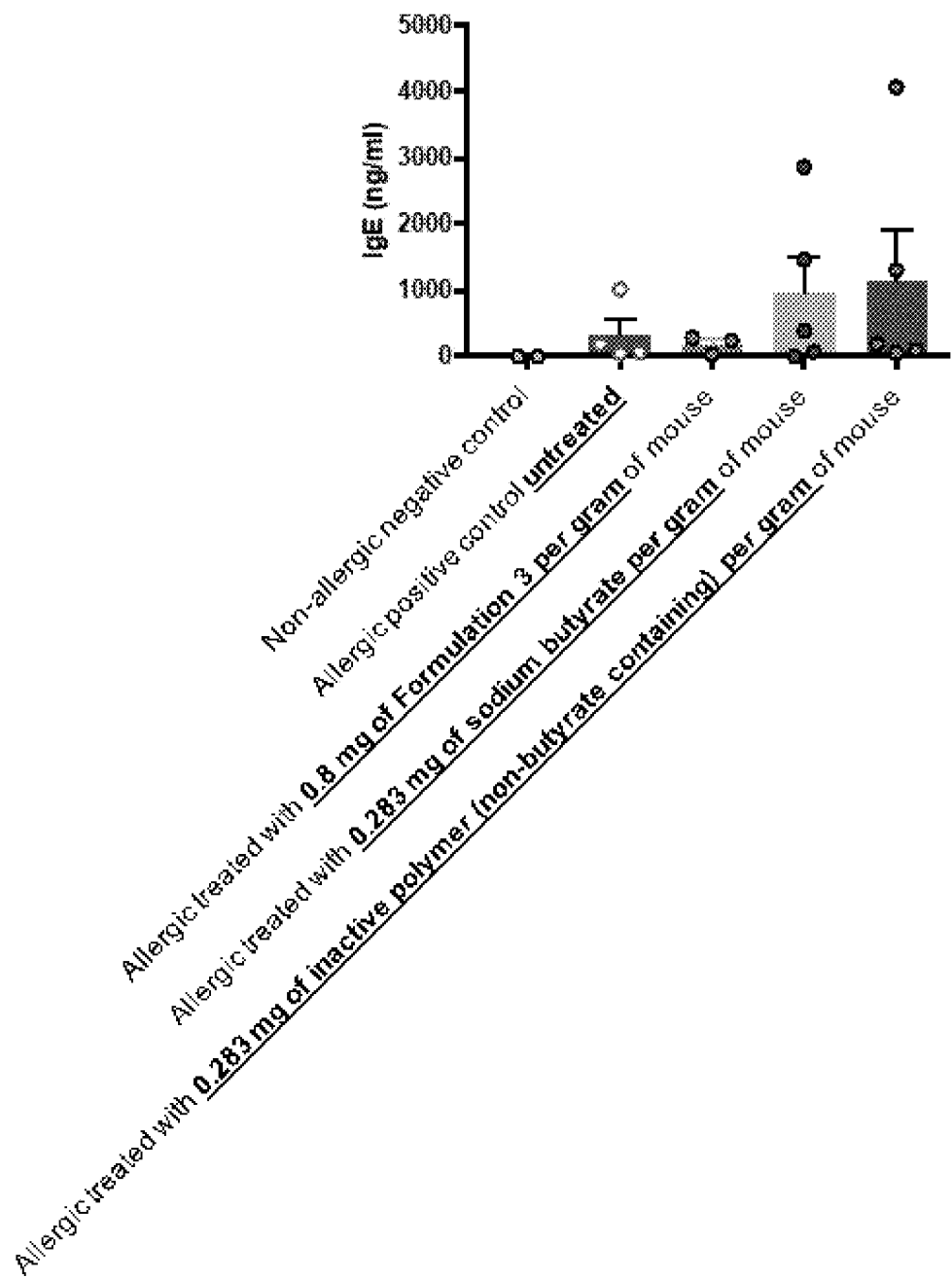
Figure 27C:
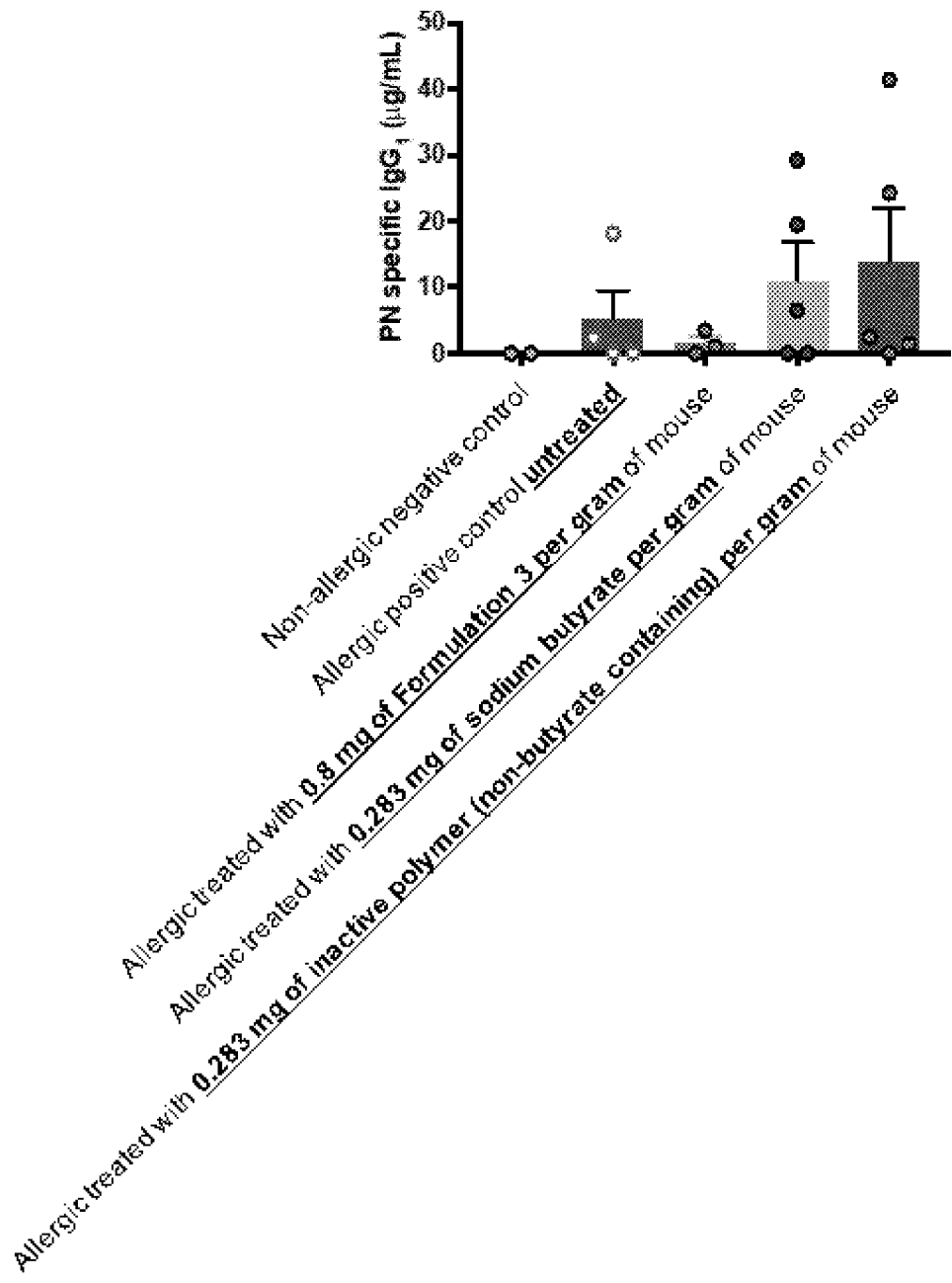
Figure 27D:
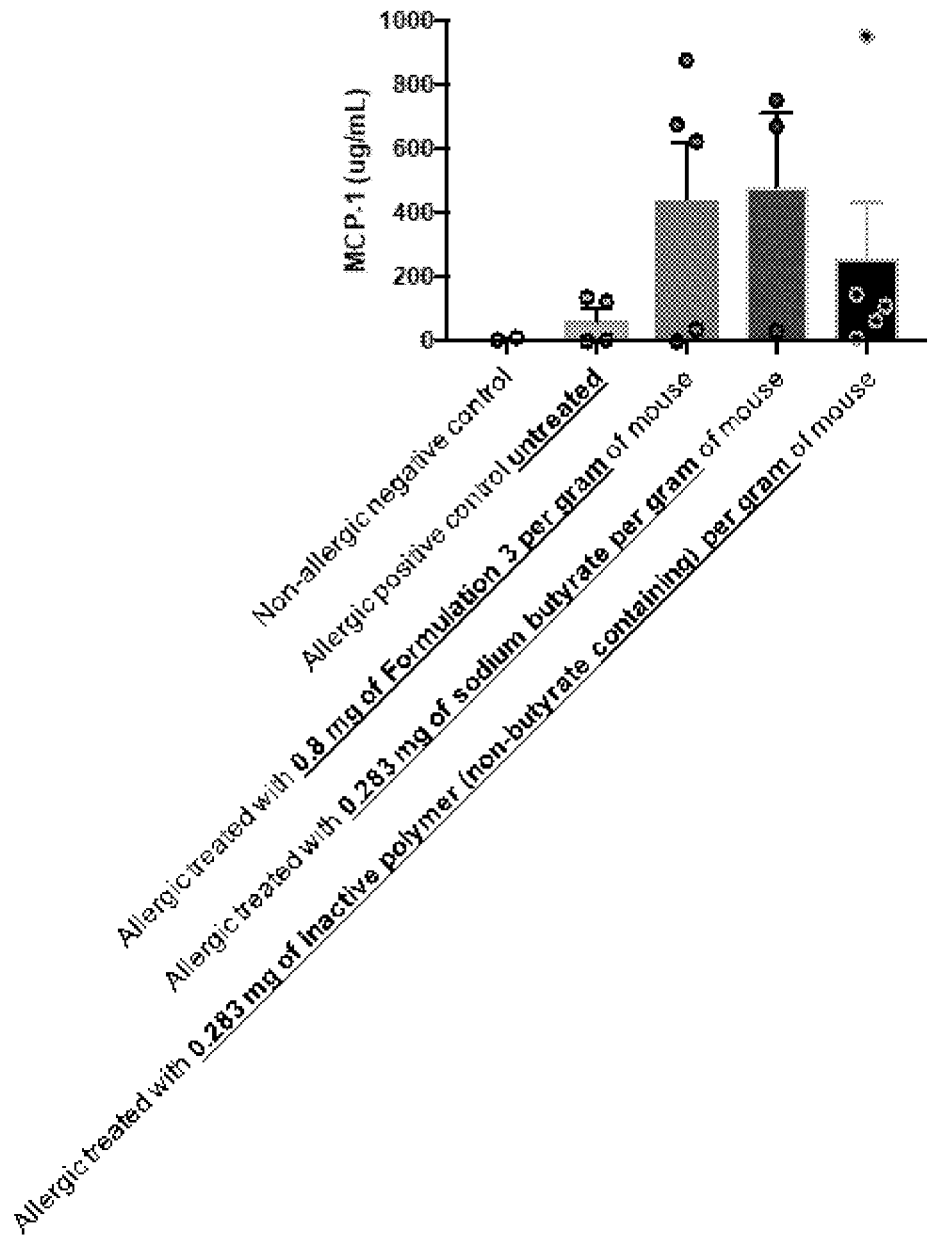

8 mg of Formulation 1 and Formulation 3 were administered to groups of mice (N=8 per group) in a single dose oral administration via intragastric gavage and the fecal material from each mouse collected and combined over a period of 24 hours. The samples were processed for gas chromatography and the concentration of free butyrate was determined using the method described in Example 6. The ratio of free butyrate to theoretically released butyrate was determined and converted to percent release (FIG. 26).

These three formulations were compared using the induced allergy model procedure described in Examples 5 and 7 (FIG. 27). After the mice were given 5 mg of peanut protein via intraperitoneal injection, core body temperature was monitored rectally for 90 minutes after injection and mouse serum was collected 90 minutes and 24 hours after injection. Serum was processed for ELISA and peanut-specific Immunoglobulin E (IgE), peanut-specific Immunoglobulin G1 (IgG1), and mouse mast cell protease-1 (mMCP-1) was determined. These results demonstrate that molecular weight differences, and not block ratio differences, lead to differences in therapeutic effect. Specifically, Formulation 2, which does not differ significantly in block ratio from Formulations 1 and 3, but does differ in molecular weight and morphology does not reduce the physiological markers and symptoms of an allergic reaction when dosed daily. Formulations 1 and 3, which differ only slightly in molecular and morphological characteristics, do reduce the physiological markers and symptoms of an allergic reaction when dosed daily.

REFERENCES

The following references, some of which are cited above, are herein incorporated by reference in their entireties.
Arpaia, N., Campbell, C., Fan, X., Dikiy, S., van der Veeken, J., deRoos, P., Liu, H., Cross, J. R., Pfeffer, K., Coffer, P. J., and Rudensky, A. Y. (2013). Metabolites produced by commensal bacteria promote peripheral regulatory T-cell generation. Nature 504, 451-455.

Berni Canani, R., Gilbert, J. A., and Nagler, C. R. (2015). The role of the commensal microbiota in the regulation of tolerance to dietary allergens. Curr Opin Allergy Clin Immunol, 15, 243-249.

Berni Canani, R., Sangwan, N., Stefka, A. T., Nocerino, R., Papro, L., Aitoro, R., Calignano, A., Kahn, A. A., Gilbert, J. A., and Nagler, C. R. (2016). *Lactobacillus rhamnosus* GG-supplemented formula expands butyrate-producing bacterial strains in food allergic infants. ISME J, 10, 742-750.

Furusawa, Y., Obata, Y., Fukuda, S., Endo, T. A., Nakato, G., Takahashi, D., Nakanishi, Y., Uetake, C., Kato, K., Kato, T., Takahashi, M., Fukuda, N. N., Murakami, S., Miyauchi, E., Hino, S., Atarashi, K., Onawa, S., Fujimura, Y., Lockett, T., Clarke, J. M., Topping, D. L., Tomita, M., Hori, S., Ohara, O., Morita, T., Koseki, H., Kikuchi, J., Honda, K., Hase, K., and Ohno, H., (2013). Commensal microbe-derived butyrate induces the differentiation of colonic regulatory T cells. Nature 504, 446-450.

Haghikia, A., Jörg, S., Duscha, A., Berg, J., Arndt, M., Waschbisch, A., Hammer, A., Lee, D.-H., May, C., Wilck, N., Balogh, A., Ostermann, A. I., Schebb, N. H., Akkad, D. A., Grohme, D. A., Kleinewietfeld, M., Kempa, S., Thone, J., Demir, S., Möller, D. N., Gold, R., and Linker, R. A. (2015). Dietary Fatty Acids Directly Impact Central Nervous System Autoimmunity via the Small Intestine. Immunity, 43, 817-829.

Kaur, A., (2012) Modulation of gut microbiota and its environment using starch-entrapped microspheres and cereal arabinoxylans. Purdue.

MacFabe, D. F. (2015) Enteric short-chain fatty acids: microbial messengers of metabolism, mitochondria, and mind: implications in autism spectrum disorders. Microb Ecol Health Dis, 26, 28177.

Meijer, K. de Vos, P., and Priebe, M. G. (2010). Butyrate and other short-chain fatty acids as modulators of immunity: what relevance for health? Curr Opin Clin Nutr Metab Care. 13, 715-721.

Nylund, L., Nermes, M., Isolauri, E., Salminen, S., de Vos, W. M., and Satokari, R. (2015). Severity of atopic disease inversely correlates with intestinal microbiota diversity and butyrate-producing bacteria. Allergy, 70, 241-244.

Sandin, A., Bråbäck, L., Norin, E., and Bengt Björkstén, B. (2009). Faecal short chain fatty acid pattern and allergy in early childhood. Acta Paediatrica, 98, 823-827.

Smith, P. M., Howitt, M. R., Panikov, N., Michaud, M., Gallini, C. A., Bohlooly-Y, M., Glickman, J. N., and Garrett, W. S. (2013). The microbial metabolites, short chain fatty acids, regulate colonic Treg cell homeostasis. Science 341, 569-573.

What is claimed is:

1. A system comprising a supramolecular assembly of polymers having the structure:

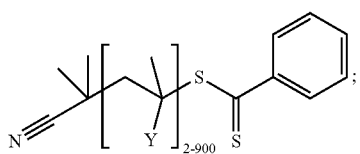

wherein each Y is independently selected from:
(i) hydrophilic side-chain, and
(ii) a side chain of the formula:

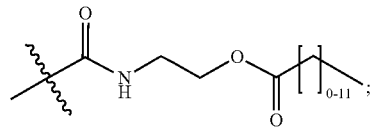

and wherein the polymers comprise at least one of each of (i) and (ii).

2. The system of claim 1, wherein the hydrophilic side-chain is of the formula:

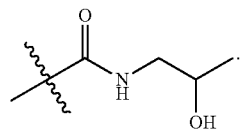 [SMILES: *C(=O)NCC(C)O]

3. The system of claim 1, wherein the polymers are random copolymers, wherein the side chains (i) and (ii) are randomly distibuted.

4. The system of claim 1, wherein the polymers are block copolymers having the structure:

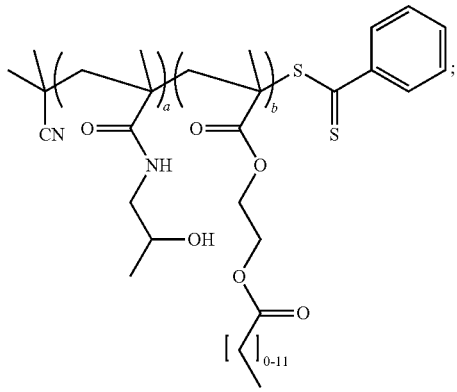

wherein a and b are collectively 2-900.

5. The system of claim 1, wherein the supramolecular assembly is a micelle or nanoparticle.

6. A pharmaceutical composition comprising a system of claim 1 and a pharmaceutically-acceptable carrier.

7. A food or nutraceutical composition comprising a system of claim 1 and a pharmaceutically-acceptable carrier.

* * * * *